(12) United States Patent
Harbison et al.

US007611838B2

(10) Patent No.: US 7,611,838 B2
(45) Date of Patent: Nov. 3, 2009

(54) BIOLOGICALLY-ACTIVE DNA-BINDING SITES AND RELATED METHODS

(75) Inventors: Christopher T. Harbison, Hamilton, NJ (US); Richard A. Young, Weston, MA (US); David B. Gordon, Somerville, MA (US); Ernest Fraenkel, Cambridge, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 10/591,271

(22) PCT Filed: Mar. 3, 2005

(86) PCT No.: PCT/US2005/007249

§ 371 (c)(1),
(2), (4) Date: Aug. 6, 2007

(87) PCT Pub. No.: WO2005/088306

PCT Pub. Date: Sep. 22, 2005

(65) Prior Publication Data

US 2008/0038720 A1  Feb. 14, 2008

Related U.S. Application Data

(60) Provisional application No. 60/604,470, filed on Aug. 25, 2004, provisional application No. 60/550,074, filed on Mar. 4, 2004.

(51) Int. Cl.
*C12Q 1/68* (2006.01)
*C07H 21/00* (2006.01)
*C07H 21/02* (2006.01)
*C07H 21/04* (2006.01)
*G01N 33/48* (2006.01)

(52) U.S. Cl. .................. 435/6; 536/22.1; 536/23.1; 536/24.3; 702/19

(58) Field of Classification Search ............ 435/6; 536/23.1, 24.3; 702/19
See application file for complete search history.

(56) References Cited

U.S. PATENT DOCUMENTS

| | | | |
|---|---|---|---|
| 5,424,188 A | | 6/1995 | Schneider et al. |
| 5,686,574 A | * | 11/1997 | Moore et al. ............... 530/350 |
| 5,989,810 A | * | 11/1999 | Flanagan et al. ............. 435/6 |
| 6,066,452 A | * | 5/2000 | Weissman et al. ............ 435/6 |
| 6,109,776 A | | 8/2000 | Haas |
| 6,410,233 B2 | | 6/2002 | Mercola et al. |
| 6,410,243 B1 | | 6/2002 | Wyrick et al. |
| 6,852,832 B1 | * | 2/2005 | Kowalczykowski et al. . 530/350 |
| 6,982,145 B1 | | 1/2006 | Mercola et al. |
| 2007/0003973 A1 | * | 1/2007 | Eberwine ..................... 435/6 |
| 2007/0059797 A1 | * | 3/2007 | Low et al. ................. 435/69.1 |

FOREIGN PATENT DOCUMENTS

| | | |
|---|---|---|
| WO | WO 01/16378 | 3/2001 |
| WO | WO0116378 A2 | 3/2001 |
| WO | WO 02/14550 | 2/2002 |
| WO | WO0214550 A2 | 2/2002 |
| WO | WO 2004/053106 | 6/2004 |
| WO | WO2004053106 A2 | 6/2004 |
| WO | WO 2004/087965 | 10/2004 |
| WO | WO2004087965 A2 | 10/2004 |
| WO | WO 2004/097577 | 11/2004 |
| WO | WO2004097577 A2 | 11/2004 |
| WO | WO 2005/054461 | 6/2005 |
| WO | WO2005054461 A2 | 6/2005 |

OTHER PUBLICATIONS

Blackwell et al., Differences and similarities in DNA-binding preferences of MyoD and E2A protein complexes revealed by binding site selection. Science 250 ( 4984) : 1104-1110 (1990).*
Blackwell T.K. Selection of protein binding sites from random nucleic acid sequences. Methods in Enzymol. 254, 604-618 (1995).*
Bussemaker et al., Building a dictionary for genomes: identification of presumptive regulatory sites by statistical analysis. PNAS 97 (18) : 10,096-10,100 (2000).*
Chittenden et al.The T/E1A-Binding Domain of the Retinoblastoma Product Can Interact Selectively with a Sequence-Specific DNA-Binding Protein. Cell 65 (6) : 1073-1082 (1991).*
Desjarlais et al. Toward rules relating zinc finger protein sequences and DNA binding site preferences. PNAS 89(16): 7345-7349 (1992).*
Gelfand et al., Prediction of transcription regulatory sites in Archaea by a comparative genomic approach. Nucleic Acids Research 28(3):695-705 (2000).*
van Heiden et al. Extracting regulatory sites from the upstream region of yeast genes by computational analysis of oligonucleotide frequencies. Journal of Molecular Biology 281 (5):. 827-842 (1998).*
Kellis et al. Sequencing and comparison of yeast species to identify genes and regulatory elements. Nature 423(6937):241-54 (May 2003).*
Kinsler et al. Whole genome PCR: application to the identification of sequences bound by gene regulatory proteins. Nucleic Acids Research 17 (10) : 3645-3653 (1989).*
Liu et al., An algorithm for finding protein-DNA binding sites with applications to chromatin-immunoprecipitation microarray experiments. Nature Biotechnology 20(8):835-839 (2002).*
Mavrothalassitis et al. Defining target sequences of DNA-binding proteins by random selection and PCR: determination of the GCN4 binding sequence repertoire. DNA and cell biology 9(10):783-788(1990).*

(Continued)

*Primary Examiner*—Ethan Whisenant
(74) *Attorney, Agent, or Firm*—James S. Keddie; Bozicevic, Field & Francis LLP

(57) ABSTRACT

The invention relates to the identification of biologically-active DNA-binding sites to which a protein of interest binds in a cell. The invention also relates to the identification of agents and conditions which alter the biologically-active DNA-binding sites to which a protein binds. One aspect of the invention also provides methods for identifying pathways that are regulated by transcriptional regulators and for modulating the activity of the pathways.

17 Claims, 12 Drawing Sheets

OTHER PUBLICATIONS

McCue et al. Phylogenetic footprinting of transcription factor binding sites in proteobacterial genomes. Nucleic Acids Research 29(3) : 774-782 (2001).*

McGuire et al. Conservation of DNA Regulatory Motifs and Discovery of New Motifs in Microbial Genomes. Genome Research 10: 744-757 (2000).*

Nørby et al. Determination of recognition-sequences for DNA-binding proteins by a polymerase chain reaction assisted binding site selection method (BSS) using nitrocellulose immobilized DNA binding protein. Nucleic Acids Research 20(23) : 6317-6321 (1992).*

Pritsker et al. Whole-genome discovery of transcription factor binding sites by network-level conservation. Genome Research 14: 99-108 (Dec 2003).*

Thiesen et al., Target Detection Assay (TDA): a versatile procedure to determine DNA blinding sites as demonstrated on SP1 protein. Nucleic Acids Research, 18(11) : 3203-3209 (1990).*

Wang et al. Combining phylogenetic data with co-regulated genes to identify regulatory motifs. Bioinformatics 19(18) : 2369-2380 (Dec. 2003).*

Aparicio et al., "Components and dynamics of DNA replication complexes in S. cerevisiae: redistribution of MCM proteins and Cdc45p during S phase," 1997, Cell, 91(3):59-69.

Barany, "The ligase chain reaction in a PCR world," 1991, PCR Methods Appl., 1(1):5-16.

Bar-Joseph et al., "Computational discovery of gene modules and regulatory networks", Nat. Biotechnol., 2003, 21 (11):1337-1342.

Bigler et al., "Isolation of a thyroid hormone-responsive gene by immunoprecipitation of thyroid hormone receptor- DNA complexes," 1994, Mol. Cell Biol., 14(11):7621-7632.

Bigler et al., "Novel location and function of a thyroid hormone response element," 1995, EMBO J., 14 (22):5710-5723.

Blat et al., "Cohesins bind to preferential sites along yeast chromosome III, with differential regulation along arms versus the centric region," 1999, Cell, 98(2)249-259.

Botquin et al., "New POU dimer configuration mediates antagonistic control of an osteopontin preimplantation enhancer by Oct-4 and Sox-2," 1998, Genes Dev., 12(13):2073-2090.

Cohen-Kaminsky et al., "Chromatin immunoselection defines a TAL-1 target gene," 1998, EMBO J., 17 (17):5151-5160.

De Risi et al., "Exploring the metabolic and genetic control of gene expression on a genomic scale," 1997, Science, 278(5338):680-686.

Deveaux et al., "p45 NF-E2 regulates expression of thromboxane synthase in megakaryocytes," 1997, EMBO J, 16 (18):5654-5661.

Gould et al., "Connectin, a target of homeotic gene control in Drosophila ," 1992, Development, 116(4):1163-1174.

Gould et al., "Targets of homeotic gene control in Drosophila," 1990, Nature, 348(6299):308-312.

Graba et al., "Drosophila Hox complex downstream targets and the function of homeotic genes," 1997, BioEssays, 19 (5):379-388.

Graba et al., "DWnt-4, a novel Drosophila Wnt gene acts downstream of homeotic complex genes in the visceral mesoderm," 1995, Development, 121(1):209-218.

Graba et al., "Homeotic control in Drosophila; the scabrous gene is an in vivo target of Ultrabithorax proteins," 1992, EMBO J.,11(9):3375-3384.

Grandori et al., "Myc-Max heterodimers activate a DEAD box gene and interact with multiple E box-related sites in vivo," 1996, EMBO J., 15(16):4344-4357.

Hallahan et al., "C-jun and Egr-1 participate in DNA synthesis and cell survival in response to ionizing radiation exposure," 1995, J. Biol. Chem. 270(51):30303-30309.

Hartemink et al., "Combining location and expression data for principled discovery of genetic regulatory network models," 2002, Pac Symp. Biocomput., 437-449.

Hecht et al., "Spreading of transcriptional repressor SIR3 from telomeric heterochromatin," 1996, Nature, 383 (6595):92-96.

Holstege et al., "Dissecting the regulatory circuitry of a eukaryotic genome," 1998, Cell, 95(5):717-728.

Kohwi-Shigematsu et al., "Identification of base-unpairing region-binding proteins and characterization of their in vivo binding sequences," 1998, Methods Cell Biol., 53:323-354.

Kumar et al., "Forkhead transcription factors, Fkh1p and Fkh2p, collaborate with Mcm1p to control transcription required for M-phase," 2000, Curr. Biol. 10(15):896-906.

Lee et al., "Transcriptional regulatory networks in Saccharomyces cerevisiae," 2002, Science, 298(5594):799-804.

Mukherjee et al., "Rapid analysis of the DNA-binding specificities of transcription factors with DNA microarrays ," 2004, Nat. Genet., 36(12):1331-1339.

Nickerson et al., "The nuclear matrix revealed by eluting chromatin from a cross-linked nucleus," 1997, Proc. Natl. Acad. Sci. USA, 94(9):4446-4450.

Odom et al., "Control of pancreas and liver gene expression by HNF transcription factors," 2004, Science, 303 (5662):1378-1381.

Orlando et al., "Analysis of chromatin structure by in vivo formaldehyde cross-linking," 1997, Methods,11(2):205-214.

Orlando et al., "Mapping Polycomb-repressed domains in the bithorax complex using in vivo formaldehyde cross-linked chromatin," 1993, Cell, 75(6):1187-1198.

Orlando, "Mapping chromosomal proteins in vivo by formaldehyde-crosslinked-chromatin immunoprecipitation," 2000, Trends Biochem. Sc., 25(3):99-104.

Pradel et al., "From selectors to realizator," 1998, Int. J. Dev. Biol. 42(3):417-421.

Reid et al., "Coordinate regulation of yeast ribosomal protein genes is associated with targeted recruitment of Esa1 histone acetylase," 2000, Mol. Cell, 6(6):1297-1307.

Ren et al., "Genome-wide location and function of DNA binding proteins," 2000, Science, 290(5500):2306-2309.

Schena et al., "Microarrays: biotechnology's discovery platform for functional genomics," 1998, Trends Biotechnol., 16(7):301-306.

Schouten, "Hybridization selection of covalent nucleic acid-protein complexes. 2. Cross-linking of proteins to specific *Escherichia coli* mRNAs and DNA sequences by formaldehyde treatment of intact cells," 1985, J. Biol. Chem., 260(17):9929-9935.

Solomon et al., "Formaldehyde-mediated DNA-protein crosslinking: a probe for in vivo chromatin structures," 1985, Proc. Natl. Acad. Sci. USA, 82(19):6470-6474.

Solomon et al., "Mapping protein-DNA interactions in vivo with formaldehyde: evidence that histone H4 is retained on a highly transcribed gene," 1988, Cell, 53(6):937-947.

Takahashi et al., "Application of the chromatin immunoprecipitation method to identify in vivo protein-DNA associations in fission yeast," 2000, Sci. STKE, 2000(56): PL1.

Tanaka et al., "Loading of an Mcm protein onto DNA replication origins is regulated by Cdc6p and CDKs," 1997, Cell, 90(4):649-660.

Tomotsune et al., "A mouse homologue of the Drosophila tumour-suppressor gene1(2)gl controlled by Hox-C8 in vivo," 1993, Nature, 365(6441):69-72.

Walter et al., "Measurement of in vivo DNA binding by sequence-specific transcription factors using UV cross-linking," 1997, Methods,11(2):215-224.

Weinmann et al., "Isolating human transcription factor targets by coupling chromatin immunoprecipitation and CpG island microarray analysis," 2002, Genes Dev., 16(2)235-244.

Wyrick et al., "Deciphering gene expression regulatory networks," 2002, Curr. Opin. Genet. Dev., 12(2):130-136.

Zhu et al., "Two yeast forkhead genes regulate the cell cycle and pseudohyphal growth," 2000, Nature, 406 (6791):90-94.

Bar et al., "Computational discovery of gene modules and regulatory networks," Nature Biotechnology, 21(11):1337-1342, (2003).

Hartemink et al., "Combining location and expression data for principled discovery of genetic regulatory network models," Proceedings of the Pacific Symposium on Biocomputing, pp. 437-449, (2002).

Lee et al., "Transcriptional Regulatory Networks in Saccharomyces cerevisiae," Science, 298:799-804, (2002).

Mukherjee et al., "Rapid analysis of the DNA binding specificities of transcription factors with DNA microarrays," Nature Genetics, 36(12):1331-1339, (2004).

Odom et al., "Control of Pancreas and Liver Gene Expression by HNF Transcription Factors," Science, 303(5662):1378-1381, (2004).

Weinmann et al., "Isolating human transcription factor targets by coupling chromatin immunoprecipitation and CpG island microarray analysis," Genes & Development, 16:235-244, (2002).

Wyrick et al., "Deciphering gene expression regulatory networks," Current Opinion in Genetics and Development, 12:130-136, (2002).

* cited by examiner

Fig. 1B

"Rediscovered" sequence specificities

Abf1 —TCAc—   ACg

Bas1 TaACTC

Pho4 CACgTG

Rpn4 tTtGCCACc

Ste12 TgAAAC

"Discovered" sequence specificities

Phd1 gC GC gG

Rds1 CgaCCg

Snt2 GgCgCTA c

Stb4 TCg  CGA

YDR026C ——TACCCGg

Single regulator

Repetitive motifs

Multiple regulators

Co-occurring regulators

BIOLOGICALLY-ACTIVE DNA-BINDING SITES AND RELATED METHODS

CROSS-REFERENCE TO RELATED APPLICATIONS

This application is a national stage filing under 35 U.S.C. 371 of International Application PCT/US2005/007249 filed Mar. 3, 2005 which claims the benefit of U.S. Application No. 60/604,470, filed Aug. 25, 2004, entitled "BIOLOGICALLY-ACTIVE DNA-BINDING SITES AND RELATED METHODS", and of U.S. Application No. 60/550,074 filed Mar. 4, 2004, entitled "TRANSCRIPTIONAL REGULATORY CODES OF EUKARYOTIC GENOMES AND METHODS THEREOF." The entire teachings of the referenced applications are incorporated by reference herein in their entirety. International Application PCT/US2005/007249 was published under PCT Article 21(2) in English.

STATEMENT REGARDING FEDERALLY-SPONSORED RESEARCH OR DEVELOPMENT

The invention described herein was supported, in whole or in part, by the National Institute of Health grant no. HG002668. The United States government has certain rights in the invention.

BACKGROUND OF THE INVENTION

Genome sequences contain information necessary to control gene expression programs and specify protein and other gene products. DNA-binding transcriptional regulators interpret the genome's regulatory code by binding to specific sequences to induce or repress gene expression (Jacob et al. *J Mol Biol* 3, 318-56 (1961), Kellis et al. *Nature* 423, 241-54 (2003), Cliften et al. *Science* 301, 71-6 (2003)). Substantial portions of genome sequence are believed to be regulatory (Pritsker et al. *Genome Res* 14, 99-108 (2004); Wang, et al. *Bioinformatics* 19, 2369-80 (2003); Blanchette et al. *Nucleic Acids Res* 31, 3840-2 (2003); Iyer et al. *Nature* 409, 533-8. (2001); Ren et al. *Science* 290, 2306-9. (2000)), but the DNA sequences that actually contribute to the regulatory code are ill-defined. In contrast, the triplet code used to translate nucleotide sequences into protein molecules is well known (Lee et al. *Science* 298, 799-804. (2002), Lieb et al. *Nat Genet.* 28, 327-34 (2001), Roth et al. *Nat Biotechnol* 16, 939-45. (1998)). Knowledge of the genome's transcriptional regulatory code could provide new insights into the principles that govern global gene regulation.

Comparative genomics has recently been used to identify functional sequence elements in the yeast genome (Pritsker et al. *Genome Res* 14, 99-108 (2004), Wang, et al. *Bioinformatics* 19, 2369-80 (2003), Liu et al. *Nat Biotechnol* 20, 835-9 (2002), Bailey et al. *Proc Int Conf Intell Syst Mol Biol* 3, 21-9 (1995)). Comparative analysis of the genome sequences of multiple yeast species revealed phylogenetically-conserved sequences, and these sequences were used to facilitate identification of genes and putative regulatory elements. Conserved sequence information alone does not reveal, however, the subset of sequences that are bound by transcriptional regulators, the identity of the binding regulators, or the conditions under which the regulators occupy their binding sites.

Therefore, there is a need to develop novel methods and algorithms for identifying the biologically-active DNA-binding site bound by transcriptional regulators in vivo.

BRIEF SUMMARY OF THE INVENTION

The invention provides novel methods relating to biologically-active DNA-binding sites for a protein of interest. One aspect of the invention provides methods for identifying the biologically-active DNA-binding sites for a protein of interest in the genome of a cell, such as a living cell. In embodiments of the invention, the protein of interest is a transcriptional regulator, a protein for mediating DNA recombination, a protein for mediating DNA repair, a protein for mediating DNA modification, or a protein for mediating DNA replication. One aspect of the invention also provides methods for identifying the DNA-sequence motif for a protein of interest.

The invention also provides methods of identifying agents, such as antisense agents, antibodies, polypeptides or small molecules, which alter the set of biologically-active DNA-binding sites to which a protein of interest binds in a cell. Such agents may be used therapeutically, particularly where binding, or lack of binding, of a protein, such as a transcriptional regulator, to the genome of a cell results in disease. The invention further provides methods of identifying conditions or cellular genotypes where the protein of interest differentially binds to the genome of a cell.

The invention further provides methods for identifying cellular pathways that are regulated by the protein of interest, including biochemical, regulatory, gene expression and signaling pathways. The invention further provides methods to identify a property of a protein of interest, such as a transcriptional regulator, which correlates with differential binding of the protein of interest to the genome of a cell.

BRIEF DESCRIPTION OF THE DRAWINGS

FIGS. 1A-1B show a general strategy for discovering binding site specificities for yeast transcriptional regulators. FIG. 1A: Cis-regulatory sequences that likely serve as recognition sites for transcriptional regulators were identified by combining information from genome-wide location data, phylogenetically conserved sequences, and previously published data, as described in the Examples. The compendium of regulatory sequence motifs can be found in Table 3. FIG. 1B: Selected sequence specificities that were "rediscovered" and were newly discovered are displayed. The total height of the column is proportional to the information content of the position, and the individual letters have height proportional to the product of their frequency and the information content (Schneider et al. *Nucleic Acids Res* 18, 6097-100 (1990).

FIG. 2A: Portions of chromosomes illustrating locations of genes (large rectangles) and conserved DNA sequences (small boxes) bound in vivo by transcriptional regulators. FIG. 2B: Combining binding data and sequence conservation data. The diagram depicts all sequences matching a motif from the compendium (top), all such conserved sequences (middle) and all such conserved sequences bound by a regulator (bottom). FIG. 2C: Regulator binding site distribution. The line labeled "actual" shows the distribution of distances from the start codon of open reading frames to binding sites in the adjacent upstream region. The line labeled "randomized" represents a randomized distribution.

DETAILED DESCRIPTION OF THE INVENTION

I. Overview

Figure 1A:
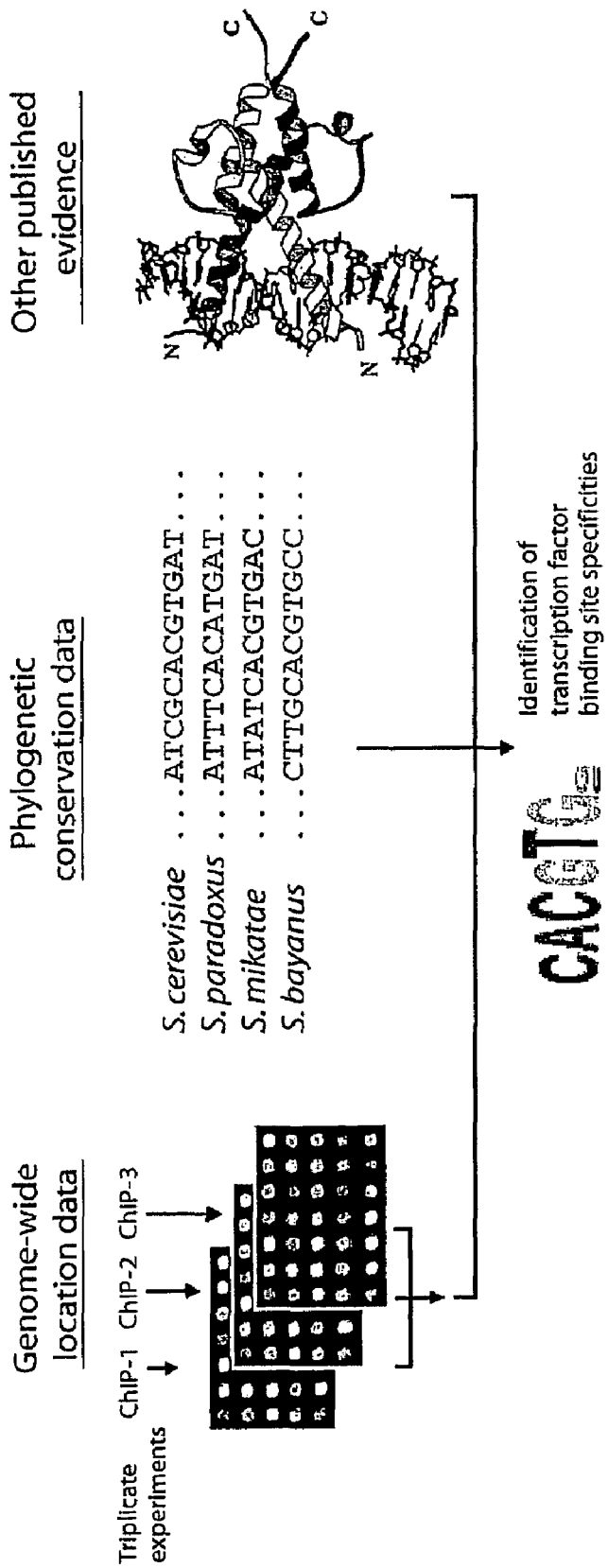

The invention provides, in part, novel methods relating to the biologically-active DNA-binding sites. One aspect of the invention provides a method of identifying a set of biologically-active DNA-binding sites for a protein of interest in the genome of a cell, the method comprising (i) identifying a set of regions of genomic DNA to which the protein of interest is bound in the cell; (ii) identifying candidate DNA-binding sites in the identified regions of genomic DNA, wherein a candidate DNA-binding site comprises a sequence corresponding to a DNA-sequence motif for the protein of interest; (iii) determining if the candidate DNA-binding sites are conserved in an equivalent genomic region in one or more different species from that of the cell, wherein a candidate DNA-binding site that is conserved in at least one species is said to be a biologically-active DNA-binding site. In one embodiment, step (i) further comprises identifying a DNA-sequence motif for the protein of interest from the set of regions of genomic DNA. In a specific embodiment, the DNA-sequence motif is enriched by a statistically-significant amount in the set of regions of genomic DNA relative to a suitable control. The term "statistically significant" as used herein means that the obtained results are not likely to be due to chance fluctuations at the specified level of probability. The two most commonly specified levels of significance are 0.05 (p=0.05) and 0.01 (p=0.01). The level of significance equal to 0.05 and 0.01 means that the probability of error is 5 out of 100 and 1 out of 100, respectively. However, higher levels of significance may be used in connection with the methods described herein, such as 0.005, 0.001, 0.0001, 0.00001, or intermediate values.

In one embodiment, the suitable control comprises a set of genomic regions which are not bound by the protein of interest in the cell. In another embodiment, the suitable control comprises a set of randomly selected genomic regions. In another embodiment, the suitable control comprises a set of randomly-generated sequences. In another embodiment, the suitable control comprises a set of genomic regions which are bound by a mutant form of the protein of interest in the cell.

In one embodiment, the candidate DNA-binding site is conserved if the equivalent genomic region in at least one different species comprises a nucleic acid sequence that matches the DNA-sequence motif for the protein of interest. In another embodiment, the DNA-sequence motif is identified using at least one algorithm. In another embodiment, the DNA-sequence motif is identified using a combination of algorithms. In one embodiment, the algorithm is selected from the group consisting of AlignACE, MEME, MDscan, the Kellis Method, Mogul, Verbumculus, YMF, BioProspector, Motif Sampler and SUPERPOSITION.

In one embodiment of the methods described herein for identifying a set of biologically-active DNA-binding sites, the regions of genomic DNA comprise promoter regions. In another embodiment, the regions of genomic DNA have a length from about between 50 bp to about 10 kb. In another embodiment, step (i) comprises performing genome-wide location analysis (GWLA) of the protein of interest. In a specific embodiment, the GWLA comprises ChIP-chip, however, any method for identifying binding sites for proteins of interest may be used. In another embodiment, the candidate DNA-binding site is less that 20 bp in length.

In one embodiment, the DNA-sequence motif is degenerate in at least one position. In another embodiment, one or more of the different species is classified in the same genus as the cell. In another embodiment, step (iii) comprises determining if the candidate DNA-binding sites are conserved in equivalent genomic regions in two or more different species. In another embodiment, the protein of interest is a transcriptional regulator. In a specific embodiment, the protein of interest comprises a DNA binding domain. In another embodiment, the protein of interest does not comprise a DNA-binding domain. In a specific embodiment, the DNA-binding domain is selected from the group consisting of zinc finger, winged-helix, leucine zipper, homeodomain and helix-loop-helix (HLH). In another embodiment, the protein of interest is a protein for mediating DNA recombination, a protein for mediating DNA repair, a protein for mediating DNA modification, or a protein for mediating DNA replication.

In one embodiment, the set of biologically-active DNA-binding sites comprises one or more biologically-active DNA-binding sites. In another embodiment, the set of biologically-active DNA-binding sites comprises 10 or more biologically-active binding sites. In another embodiment, two regions of genomic DNA are equivalent if they both comprise a sequence of at least one orthologous gene. In another embodiment, two regions of genomic DNA, each comprising an intergenic region which is flanked by a first and a second open reading frame (ORF) in their respective genomes, are said to be equivalent if (i) the first ORF in the two regions are orthologous ORFs and (ii) if the second ORFs in the two regions are orthologous ORFs.

In one embodiment, the cell is a eukaryotic cell, such as a mammalian cell, and more preferably, a human cell. In another embodiment, the cell is a primary cell, such as from a tissue biopsy. In a specific embodiment, the tissue biopsy is isolated from a subject afflicted with a disorder. In yet another embodiment, the cell is a single-cell organism, such as a yeast cell. In one embodiment, the cell is a stem cell. The term "stem cell" as used herein refers to a cell that gives rise to a lineage of cells, and that may be characterized as a cell that upon division, produces dissimilar daughters, one replacing the origin or partially differentiated stem cells. Stem cells include embryonic stem cells, umbilical cord blood stem cells, and adult/peripheral stem cells.

Another aspect of the invention provides a method of identifying an agent which alters the set of biologically-active DNA-binding sites for a protein of interest in the genome of a cell, the method comprising (i) contacting on experimental cell with a candidate agent; (ii) identifying a set of biologically-active DNA-binding sites for a protein of interest in the genome of the experimental cell of step using any of the methods described herein, thereby generating an experimental set of biologically-active DNA-binding sites; (iii) comparing (1) the experimental set of biologically-active DNA-binding sites to (2) a control set of biologically-active DNA-binding sites for the protein of interest; wherein a candidate agent is identified if the experimental set and the control set differ. In one embodiment, the control set is derived from a control cell that is not contacted with the candidate agent.

Yet another aspect of the invention provides a method of identifying a pathway that is transcriptionally regulated by a protein of interest in a cell, the method comprising (i) identifying a set of biologically-active DNA-binding sites for a protein of interest in the genome of the cell according to any of the methods described herein; and (ii) identifying at least two candidate genes likely to be regulated by binding of the protein of interest to the set of biologically-active DNA-binding sites identified in (i); wherein the pathway that is transcriptionally regulated by a protein of interest is identified if at least two candidate genes are members of the same pathway. In a specific embodiment, a pathway that is transcriptionally regulated by a protein of interest is identified if at least 2, 3, 4 or 5 candidate genes are members of the same pathway. In one embodiment, the pathway is a biochemical pathway. In another embodiment, the pathway is a gene expression pathway. In another embodiment, the pathway is a regulatory pathway. In another embodiment, the candidate gene is likely regulated by the protein of interest if the promoter for the candidate gene comprises at least one biologically-active DNA-binding site. In one embodiment, the promoter region of a candidate gene comprises from 3 kb 5' to 1 kb 3' of the transcription initiation site. In still another embodiment, the invention provides a method of modulating a pathway that is transcriptionally regulated by a protein of interest by exposing a cell to an agent or condition which alters the binding sites to which the protein of interest binds, as discussed further below.

Another aspect of the invention provides a method of identifying two sets of conditions in which a protein of interest differentially binds to the genome of a cell, the method comprising: (i) identifying a first set of biologically-active DNA-binding sites for the protein of interest in the genome of a cell according to any one of the methods described herein, wherein the cell is exposed to a first set of conditions; (ii) identifying a second set of biologically-active DNA-binding sites for the protein of interest in the genome of a cell according to any one of the methods described herein for identifying a set of biologically-active DNA-binding sites, wherein the cell is exposed to a second set of conditions; and (iii) comparing the first set of biologically-active DNA-binding sites to the second set of biologically-active DNA-binding sites and determining if the two sets differ.

Another aspect of the invention provides a method of identifying a property of a gene product of a gene of interest that correlates with the binding activity of a polypeptide encoded by the gene of interest to the genome of a cell, the method comprising (i) identifying two sets of conditions in which a protein of interest differentially binds to the genome of the cell; (ii) determining a property of a gene product of the gene of interest in (a) a cell exposed to a first set of conditions; and in (b) a cell exposed to a second set of conditions; and (iii) determining if at least one property of the gene product differs in the two cells of step (ii), thereby identifying a property that correlates with the binding activity of a gene of interest to the genome of a cell.

A related aspect of the invention provides a method of identifying a property of a gene product of a gene of interest that correlates with the binding activity of a polypeptide encoded by the gene of interest to the genome of a cell, the method comprising (i) identifying an agent which alters the set of biologically-active DNA-binding sites for a protein of interest in the genome of a cell; (ii) determining a property of a gene product of the gene of interest in (a) a cell contacted with the agent; and in (b) a cell not contacted with the agent; and (iii) determining if at least one property of the gene product differs in the two cells of step (ii), thereby identifying a property that correlates with the binding activity of a gene of interest to the genome of a cell.

In one embodiment, the property is selected from the group consisting of a protein modification, expression level, enzymatic activity and intracellular localization. In one embodiment, the expression product is an mRNA or a polypeptide. In another embodiment, the property comprises the expression level of the gene product.

In another embodiment, the property comprises the subcellular localization of the gene product. In another embodiment, the property comprises the phosphorylation state of gene product. In another embodiment, the property comprises the molecular weight of the gene product. In another embodiment, the property comprises the isoelectric point of the gene product. In another embodiment, the property comprises the nucleic acid sequence or the amino acid sequence of the gene product. In another embodiment, the property comprises the physical association of the protein of interest with another polypeptide.

Another aspect of the invention provides a method of identifying two cell genotypes in which a protein of interest differentially binds to the genome of a cell, the method comprising: (i) identifying a first set of biologically-active DNA-binding sites for the protein of interest in the genome of a cell of a first genotype; (ii) identifying a second set of biologically-active DNA-binding sites for the protein of interest in the genome of a cell of a second genotype; (iii) comparing the first set of biologically-active DNA-binding sites to the second set of biologically-active DNA-binding sites and determining if the two sets differ.

II. Definitions

For convenience, certain terms employed in the specification, examples, and appended claims, are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

A "patient" or "subject" to be treated by the method of the invention can mean either a human or non-human animal, preferably a mammal.

The term "encoding" comprises an RNA product resulting from transcription of a DNA molecule, a protein resulting from the translation of an RNA molecule, or a protein resulting from the transcription of a DNA molecule and the subsequent translation of the RNA product.

The term "promoter" is used herein to mean a DNA sequence that initiates the transcription of a gene. Promoters are typically found 5' to the gene and located proximal to the start codon. If a promoter is of the inducible type, then the rate of transcription increases in response to an inducer. Promoters may be operably linked to DNA binding elements that serve as binding sites for transcriptional regulators. The term "mammalian promoter" is used herein to mean promoters that are active in mammalian cells. Similarly, "prokaryotic promoter" refers to promoters active in prokaryotic cells.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, protein or both.

The term "recombinant" is used herein to mean any nucleic acid comprising sequences which are not adjacent in nature. A recombinant nucleic acid may be generated in vitro, for example by using the methods of molecular biology, or in vivo, for example by insertion of a nucleic acid at a novel chromosomal location by homologous or non-homologous recombination.

The term "transcriptional regulator" refers to a biochemical element that acts to prevent or inhibit the transcription of a promoter-driven DNA sequence under certain environmental conditions (e.g., a repressor or nuclear inhibitory protein), or to permit or stimulate the transcription of the promoter-driven DNA sequence under certain environmental conditions (e.g., an inducer or an enhancer).

The term "microarray" refers to an array of distinct polynucleotides or oligonucleotides synthesized on a substrate, such as paper, nylon or other type of membrane, filter, chip, glass slide, or any other suitable solid support.

The terms "disorders" and "diseases" are used inclusively and refer to any deviation from the normal structure or function of any part, organ or system of the body (or any combination thereof). A specific disease is manifested by characteristic symptoms and signs, including biological, chemical and physical changes, and is often associated with a variety of other factors including, but not limited to, demographic, environmental, employment, genetic and medically historical factors. Certain characteristic signs, symptoms, and related factors can be quantitated through a variety of methods to yield important diagnostic information.

The term "modulation" refers to upregulation (i.e., activation or stimulation), downregulation (i.e., inhibition or suppression) of a response, or the two in combination or apart. A "modulator" is a compound or molecule that modulates, and may be, e.g., an agonist, antagonist, activator, stimulator, suppressor, or inhibitor.

The term "agonist" refers to an agent that mimics or up-regulates (e.g., potentiates or supplements) the bioactivity of a protein, e.g., polypeptide X. An agonist may be a wild-type protein or derivative thereof having at least one bioactivity of the wild-type protein. An agonist may also be a compound that upregulates expression of a gene or which increases at least one bioactivity of a protein. An agonist may also be a compound which increases the interaction of a polypeptide with another molecule, e.g., a target peptide or nucleic acid.

The term "antagonist" refers to an agent that downregulates (e.g., suppresses or inhibits) at least one bioactivity of a protein. An antagonist may be a compound which inhibits or decreases the interaction between a protein and another molecule, e.g., a target peptide or enzyme substrate. An antagonist may also be a compound that downregulates expression of a gene or which reduces the amount of expressed protein present.

The term "intergenic region" as used herein refer to genomic DNA sequence which lie between adjacent open-reading frames (ORFs). Intergenic regions may comprise regulatory elements such as promoter, operators or enhancers, although regulatory sequences can also be located in coding regions.

III. Methods of Identifying Biologically-Active DNA-Binding Sites

One aspect of the invention provides methods of identifying a set of biologically-active DNA-binding sites for a protein of interest in the genome of a cell. One specific aspect method comprises (i) identifying a set of regions of genomic DNA to which the protein of interest is bound in the cell; (ii) identifying candidate DNA-binding sites in the identified regions of genomic DNA, wherein a candidate DNA-binding site comprises a sequence corresponding to a DNA-sequence motif for the protein of interest; (iii) determining if the candidate DNA-binding sites are conserved in an equivalent genomic region in one or more different species from that of the cell, wherein a candidate DNA-binding site that is conserved in at least one species is a biologically-active DNA-binding site.

The methods of the present invention are not limited to any particular type of cell. The cell may be, for example, a prokaryotic cell or an eukaryotic cell. In one preferred embodiment, the cell is a mammalian cell. Other preferred cells include primate, and rodent cells, such as human and mouse cells, and cells from model organisms such as yeast, zebrafish, C. elegans or Drosophila. The cells used in methods of the invention may be cells that have been passaged extensively in vitro, including immortalized cell lines such as cancer cell lines. Cell lines that may be used in the present invention also include stem cells, such as embryonic and adult stem cells.

In other embodiments, the cells are primary cells which have undergone minimal, if any, culturing in vitro. In one exemplary embodiment, the cells are derived from freshly isolated tissue, such as from a tissue biopsy. Such cells are preferred in some embodiments as the patterns of gene expression in such cells would be expected to most closely resemble the in vivo state. In some embodiments, the cells are derived from a subject afflicted with a disorder. Such cells may provide insights into the disease state and aid in the identification of therapeutics to treat or prevent the disorder.

In some embodiments, the cells are of a single cell type, while other embodiments may include cells of more than one cell type. For instance, one embodiment may use only hepatocytes, whereas other embodiments may use hepatocytes, neurons and pancreatic beta cells. In other embodiments, the cells may include cells from an entire organism or combination of organisms.

The protein of interest in the methods described herein may associate directly or indirectly with DNA. In some embodiments, the protein of interest comprises a DNA-binding domain which may allow direct binding to DNA molecules. Exemplary DNA-binding domains include zinc finger, winged-helix, leucine zipper, homeodomain or helix-loop-helix (HLH). In other embodiments, the protein of interest lacks a DNA-binding domain. In certain embodiments of the invention, the protein of interest comprises specific transcription factors, coactivators, corepressors or complexes thereof. Transcription factors bind to specific cognate DNA elements such as promoters, enhancers and silencer elements, and are responsible for regulating gene expression. Transcription factors may be activators of transcription, repressors of transcription or both, depending on the cellular context. In one embodiment, the protein of interest is any one of the transcriptional regulators listed in the TRANSFAC database (See E. Wingender, X. Chen, R. Hehl, H. Karas, I. Liebich, V. Matys, T. Meinhardt, M. Pr, I. Reuter, and F. Schacherer. TRANSFAC: an integrated system for gene expression regulation. Nucleic Acids Res., 28:316-319, 2000).

Transcription factors may belong to any class or type of known or identified transcription factor. Examples of known families or structurally-related transcription factors include helix-loop-helix, leucine zipper, zinc finger, ring finger, and hormone receptors. Transcription factors may also be selected based upon their known association with a disease or the regulation of one or more genes. For example, transcription factors such as c-myc, Rel/Nf-kB, neuroD, c-fos, c-jun, and E2F may be targeted. Antibodies directed to any transcriptional coactivator or corepressor may also be used according to the invention. Examples of specific coactivators include CBP, CTIIA, and SRA, while specific examples of corepressors include the mSin3 proteins, MITR, and LEUNIG. Furthermore, the genes regulated by proteins associated with transcriptional complexes, such as the histone acetylases (HATs) and histone deacetylases (HDACs), may also be de determined using the methods described herein.

In other embodiments of the methods described herein, the protein of interest is a basal transcription factor or a component of the basal transcription machinery. In specific embodiments, components of the basal transcription machinery comprise RNA polymerases, including polI, polII and polIII, TBP, NTF-1 and Sp1 and any other component of TFIID, including, for example, the TAFs (e.g. TAF250, TAF150, TAF135, TAF95, TAF80, TAF55, TAF31, TAF28, and TAF20), or any other component of a polymerase holoenzyme.

In some embodiments of the methods described herein, the protein of interest is native to the cell. By native it is meant that the protein of interest naturally occurs in the cell. In other embodiments, the protein of interest is not native to the cell and is instead introduced through manipulation of the cell, including microinjection of the protein, liposome-mediated delivery of the protein (Weiner et al., (1994) Immunomethods; 4(3):201-9), or fusion to a polypeptide which allows entry into the cell, such as fusion to a Tat polypeptide (Becker-Hapak et al., (2001) Methods. 24(3):247-56). In more preferred embodiments, the non-native protein is introduced into the cell through standard genetic engineering and recombinant DNA techniques.

In some embodiments, the protein of interest is native to a cell of a different species from that of the cell used in the instant methods. In some embodiments, the protein of interest is a viral protein. In such embodiments, a cell may be contacted with a virus under conditions which allow infection of the cell by the virus in order to allow expression of the viral protein in the cell. In some embodiments, the gene encoding the protein of interest carries missense mutations, nonsense mutations, deletions, insertions or inversions such that a mutant protein may be expressed in the cell. In some embodiments, the protein of interest is a fusion protein. In one specific embodiment, the fusion protein comprises a transcriptional regulator fused to a "tag" which allows visualization or purification of the protein. Preferred tags include GFP polypeptides, GST domains, myc tags, His tags, or any other tag which allows the immunoprecipitation of the protein of interest when complexed with chromatin. In other embodiments, the protein-of-interest comprise artificial transcriptional regulators (see WO02/31166).

In some embodiments of the methods described herein, the protein of interest has been causally implicated in a disease or disorder. Examples of diseases and transcriptional regulators which may cause them may be found in the scientific and medical literature, including in Medical Genetics, L. V. Jorde et al., Elsevier Science 2003, and Principles of Internal Medicine, 15th edition, ed by Braunwald et al., McGraw-Hill, 2001; American Medical Association Complete Medical Encyclopedia (Random House, Incorporated, 2003); and The Mosby Medical Encyclopedia, ed by Glanze (Plume, 1991). In some embodiments, the disorder is characterized by impaired function of at least one of the following organs or tissues: brain, spinal cord, heart, arteries, esophagus, stomach, small intestine, large intestine, liver, pancreas, lungs, kidney, urinary tract, ovaries, breasts, uterus, testis, penis, colon, prostate, bone, scalp, muscle, cartilage, thyroid gland, adrenal gland, pituitary, bone marrow, blood, thymus, spleen, lymph nodes, skin, eye, ear, nose, teeth or tongue.

Biologically-active DNA-binding sites include sites on the genomic DNA of the cell to which the protein of interest binds. One skilled in the art would appreciate that while many sequences in a genome may match a DNA-sequence motif for the protein of interest, many of these sites are not bound in vivo by the protein of interest, and thus would not be considered biologically-active DNA-binding sites.

In one embodiment, a biologically-active DNA-binding site comprises the minimal DNA sequence required for specific binding of the protein of interest to the DNA. In another embodiment, the biologically-active DNA-binding site comprises the stretch of DNA sequence that is physically contacted by the protein of interest when the protein of interest is bound to DNA under native or physiological conditions such as in a live cell. In another embodiment, the biologically-active DNA-binding site comprises the promoter region, or any other functionally defined regulatory region for a gene, to which a protein of interest is bound to under native conditions in a cell.

In some embodiments of the methods described herein, the set of biologically-active DNA-binding sites comprises one biologically-active DNA-binding site. In another embodiment, the set includes at least 2, 3, 4, 5, 6, 7, 8, 9, 10, 12, 15, 20, 25, 30, 40 or 50 biologically-active DNA-binding sites. In some embodiments, the set comprises the biologically-active DNA-binding site bound by a protein of interest when the cell is grown under one set of conditions, while in other embodiments the set may comprise more than one set of conditions. Accordingly, the set may be a "snapshot" of the sites bound by the protein of interest, or it may be a cumulative set of various snapshots, each taken under a different set of conditions. The set may comprise the sites bound by the protein of interest in one cell type or in more than one cell type. For example, the set may comprises the sites bound by E2F in hepatocytes, or it may comprise the sites bound in hepatocytes, adipocytes, neurons. In some embodiments, the set may comprise the binding sites for a protein of interest in an organism. For example, the set may comprise the sites for a transcription factor in *C. elegans*, such as the set that may be obtained when whole worms are used as starting materials. In another embodiment, the set comprises the binding sites located in promoter regions of at least 5%, 10%, 20%, 30%, 50%, 70%, 80%, 90%, 95%, 98% or 99% of the genes in the genome of the cell.

The identification of a set of regions of genomic DNA to which the protein of interest is bound in the cell may be achieved using any technique know in the art. In a preferred embodiments, the genomic regions are identified using genome-wide location analysis (GWLA). GWLA has been described in International PCT application Nos. WO01/16378 and WO02/059371, and U.S. Pat. No. 6,410,243. In a preferred embodiment, the identification of the set of regions of genomic DNA to which the protein of interest is bound in the cell comprises chromatin-immunoprecipitation (ChIP) and subsequent analysis on DNA microarray (ChIP-chip analysis) (see Buck and Lieb, (2004) Genomics 83:349-360; Ren et al. (2004) Methods Enzymol. 376:304-315; Urnov et al. (2003) *Journal of Cellular Biochemistry* 88:684-694; and Orlando, Valerio (2000) *TIBS* 25:99-103).

In a preferred embodiment, the regions of genomic DNA, i.e. chromatin fragments, bound by the protein of interest are isolated using chromatin immunoprecipitation (ChIP). Briefly, this technique involves the use of a specific antibody to immunoprecipitate chromatin complexes comprising the corresponding antigen i.e. the transcriptional regulator, and examination of the nucleotide sequences present in the immunoprecipitate. Immunoprecipitation of a particular sequence by the antibody is indicative of interaction of the antigen with that sequence. See, for example, O'Neill et al. in *Methods in Enzymology*, Vol. 274, Academic Press, San Diego, 1999, pp. 189-197; Kuo et al. (1999) *Method* 19:425-433; and Ausubel et al., supra, Chapter 21. Accordingly, in one embodiment, the DNA fragment bound the protein of interest is identified using an antibody which binds to the protein of interest.

In one embodiment of the methods described herein, the protein of interest is crosslinked to chromatin (Solomon, M. J. and Varshavsky, A., Proc. Natl. Sci. USA 82:6470-6474; Orlando, V., TIBS, 25:99-104). There are a variety of methods which can be used to link a DNA binding protein of the cell to the genome of the cell. For example, UV light can be used. In a particular embodiment, formaldehyde is used to crosslink DNA binding proteins to the genomic DNA of a cell. The chromatin may then be sheared, such as by sonication, to generate fragments of chromatin bound to the protein of interest.

In one embodiment, the chromatin immunoprecipitation technique is applied as follows. Cells which express the protein of interest, such as a native transcriptional regulator or a recombinant transcriptional regulator, are treated with an agent that crosslinks the transcriptional regulator to chromatin if that transcriptional regulator is stably bound to it. The transcriptional regulator can be crosslinked to chromatin by, for example, formaldehyde treatment or ultraviolet irradiation. Subsequent to crosslinking, cellular nucleic acid is isolated, fragmented and incubated in the presence of an antibody directed against the transcriptional regulator. Antibody-antigen complexes are precipitated, crosslinks are reversed (for example, formaldehyde-induced DNA-protein crosslinks can be reversed by heating) so that the sequence content of the immunoprecipitated DNA is tested for the presence of a specific sequence, for example, promoter regions. The antibody may bind directly to an epitope on the transcriptional regulator or it may bind to a tag on the regulator, such as a myc tag when used with an anti-Myc antibody (Santa Cruz Biotechnology, sc-764). In yet another embodiment, a non-antibody agent with affinity for the transcriptional regulator or for a tag used to it is used in place of the antibody. For example, if the transcriptional regulator comprises an affinity tag, such as a six-histidine tag, complexes may be isolated by affinity chromatography to nickel-containing sepharose. Additional variations on ChIP methods may be found in Kurdistani et al. Methods. 2003 31(1):90-5; O'Neill et al. Methods. 2003, 31(1):76-82; Spencer et al., Methods. 2003; 31(1):67-75; and Orlando et al. Methods 11: 205-214 (1997).

In one embodiment of the methods described herein, DNA fragments from a control immunoprecipitation reaction are used in place of the isolated chromatin as a control. For example, an antibody that does not react with a transcription factor being tested may be used in a chromatin IP procedure to isolate control chromatin, which can then be compared to the chromatin isolated using an antibody that does react with the transcriptional regulator. In preferred embodiments, the antibody that does not react with the transcription factor being tested also does not react with other transcriptional regulators or DNA binding proteins.

In one embodiment, labelled probes are generated from the chromatin fragments and optionally from control chromatin fragments. Labelled probes may be generated from template DNA using ligation-mediated polymerase chain reaction (LM-PCR), e.g., see Current Protocols in Molecular Biology, Ausubel, F. M. et al., eds. 1991 and U.S. Application No. 2003/0143599, the teachings of which are incorporated herein by reference) in their entirety. In specific embodiments, LM-PCR comprises fluorescently labeling amplified DNA by including fluorescently-tagged nucleotides in the LM-PCR reaction. Generally, whole genome-based amplification methods (e.g., substantially unbiased amplification methods) may be used such as Multiple Displacement Amplification (MDA) (Hosono et al, *Genome Res.* 2003; 13(5):954-64), DOP (Telenius, *Genomics* 1992; 13:718-725), primer extension preamplification or PEP (Zhang, et al., *Proc. Natl. Acad. Sci.* 1992; 89:5847-5851), inter-Alu PCR in conjunction with labelled primers and/or nucleotides. However, in still other aspects, probes are labelled without a prior amplification step.

In one embodiment of the methods described, labelled probes from control DNA fragments and the labelled probes are hybridized to a DNA microarray that includes experimental spots or features that represent all or a subset (e.g., a chromosome or chromosomes) of the genome. The fluorescent intensity of each experimental spot on the microarray from the amplified chromatin fragments relative to the amplified control chromatin indicates whether the protein of interest is bound to the DNA region located at that particular spot. Hence, the methods described herein may be applied to the detection of protein-DNA interactions across an entire genome.

In some embodiments of the methods described herein, the labelled probes are hybridized to a DNA microarray to identify the regions of genomic DNA that were bound by the protein of interest. Microarrays, also called "biochips" or "arrays" are miniaturized devices typically with dimensions in the micrometer to millimeter range for performing chemical and biochemical reactions and are particularly suited for embodiments of the invention. Arrays may be constructed via microelectronic and/or microfabrication using essentially any and all techniques known and available in the semiconductor industry and/or in the biochemistry industry, provided only that such techniques are amenable to and compatible with the deposition and screening of polynucleotide sequences. Microarrays are particularly desirable for their virtues of high sample throughput and low cost for generating profiles and other data.

DNA microarray and methods of analyzing data from microarrays are well-described in the art, including in DNA Microarrays: A Molecular Cloning Manual, Ed by Bowtel and Sambrook (Cold Spring Harbor Laboratory Press, 2002); Microarrays for an Integrative Genomics by Kohana (MIT Press, 2002); A Biologist's Guide to Analysis of DNA Microarray Data, by Knudsen (Wiley, John & Sons, Incorporated, 2002); and DNA Microarrays: A Practical Approach, Vol. 205 by Schema (Oxford University Press, 1999); and Methods of Microarray Data Analysis II, ed by Lin et al. (Kluwer Academic Publishers, 2002), hereby incorporated by reference in their entirety.

In some embodiments, DNA microarray for use in the present invention may be constructed with spots comprising nucleic acid with promoter sequences. In some embodiments of the methods described herein, the promoter region of a gene comprises from at least 700 bp upstream to at least 200 bp downstream of the transcriptional start site of the gene. In some embodiments, the promoter region comprises at least about 30, 40, 50, or 60 nucleotides in length. In specific embodiments, the promoter region of a gene as found on the spots of the microarray comprises a sequence of at least 30 nucleotides whose sequence is identical to a region stretching from 3 kb upstream to 1 kb downstream of the transcriptional start site of said gene. Smaller probes (e.g., about 30-200 nucleotides) spotted on the microarray have the advantage that smaller corresponding genomic regions to which the protein of interest is bound may be identified, but have the disadvantage that more probes must be spotted onto the microarray to obtain the same coverage as larger probes.

In some embodiments, the sequence of the region of genomic DNA to which the protein of interest is bound corresponds to the sequence of the nucleic acid on a spot on the microarray to which the transcription factor is found to be bound. In some embodiments where the spots on the microarray have overlapping sequences, the sequences of the genome regions to the which the protein of interest binds may be deduced to be shorter than the length of each of the spotted nucleic acids. For example, if a protein of interest was found to bind to probes having sequences C-D-E-F and E-F-G-H, wherein each letter represents stretches of for example 20-500 bp, and the protein of interest also failed to bind to probes having the sequences A-B-C-D and G-H-I-J, then it could be deduced that the region to which the protein of interest binds is E-F. Thus, in a preferred embodiment, the array comprises spotted nucleic acids whose sequences are tiled i.e. share overlapping regions.

In one embodiment of the methods described herein, identifying candidate DNA-binding sites in the identified genomic regions comprises scanning the sequence of the identified genomic regions to identify a sequence corresponding to the DNA-sequence motif for the protein of interest. In an illustrative example, if three genomic regions were identified, each of about 1 kb, and the DNA-sequence motif for the protein of interest was GCANTGC, then each of the three 1 kb sequences would be scanned for a sequence that matches this motif, i.e. for any of the subsequences GCAATGC, GCAGTGC, GCACTGC and GCATTGC. If such a subsequence was identified in a genomic region, then that subsequence would be determined to be a candidate DNA-binding site. Accordingly, a candidate DNA-binding site has a sequence identical to the DNA-sequence motif (i.e. it has an identical sequence to one of the subsequences of the DNA-sequence motif), and is present in an identified genomic region. An identified genomic region might contain no candidate binding sites, it may contain one, or it may contain more than one.

Identification of candidate binding sites, having a sequence defined by the DNA-sequence motif in the genomic regions to which the protein of interest binds may be carried out through manual examination of the genomic regions. More preferably however, software programs and algorithms known in the art are used to partially or fully automate the process. Programs that may be used in the present invention include, but are not limited to, the Ahb program (Rajewsky et al. (2002) *BMC Bioinformatics*, 3:30), the Clover program, (see Frith et al. (2004) *Nucleic Acids Res.*, 32, 1372-1381), and the MotifScaliner program (Thijs et al. (2001), Proceedings Recomb'2001, 305-312). In another embodiment, the Fuzznuc program is used to identify candidate binding sites in the set of genomic regions which correspond to the DNA-sequence motifs. Ffuzznuc is one program that is part of the EMBOSS suite of biological software tools distributed by the HGMP, UK (See Rice et al. (2000) EMBOSS: The European Molecular Biology Open Software Suite. *Trends in Genetics*, Vol 16, No 6. pp. 276-277). In yet another embodiment, the ROVER (Relative OVER-abundance of cis-elements) program is used to identify candidate binding sites (See Haverty et al. (2004) *Nucleic Acids Res.*, 32, 179-188). Additional approaches described in the literature may also be used (See Sharan et al. (2003). *Bioinformatics*, 19 (Suppl 1), I283-I291; and Elkon et al. (2003) *Genome Res.*, 13, 773-780.)

In some embodiments of the methods described herein, the DNA-sequence motif for a protein of interest is unknown or poorly defined. Accordingly, in some embodiments, the methods further comprises identifying a DNA-sequence motif for the protein of interest from the sequences of the identified genomic DNA. In one embodiment, identifying a DNA-sequence motif generally comprises identifying one or more DNA sequences that are enriched in the regions of genomic DNA to which the protein of interest is bound relative to a suitable control.

In a specific embodiment, the suitable control comprises a control set of genomic regions. The control set may comprise a set of genomic regions which are not bound by the protein of interest in the cell. In other embodiments, the control set comprises a set of randomly selected genomic regions. In yet another embodiment, the control set comprises randomized DNA sequences. In a preferred embodiment, the base composition of the randomized DNA sequences is substantially the same as base composition of either (i) the genome of the cell; (ii) the genomic regions to which the protein of interest binds; or (iii) the average of promoter or other regulatory regions. For instance, if 60% and 40% of the basepairs in the genomic regions that are bound by the protein of interest are A-T and G-C basepairs respectively, then the randomized might contain this same proportion of basepairs. Alternatively, the suitable control may comprise an estimate of the frequency with which a given motif is expected based on the frequency of base pairs in the motif, without the need to actually generate randomized sequences.

In another embodiment, the control set may comprise a set of genomic regions which is bound by a mutant form of the protein of interest, such as a mutant form having deletions or substitutions in its DNA binding domain, whereas in other embodiments the control set comprises the set of genomic regions bound by a second protein, such as a transcription factor, a component of the basal transcription machinery, or a histone.

Any algorithm or software program known to one skilled in the art to identify DNA-sequence motifs may be used to identify statistically-enriched sets of DNA-sequence motifs from the set of identified genomic regions. In some embodiments, the DNA sequence motif is identified using one or more of the following programs or algorithms: Gibbs Sampler (Rajewsky et al. (2002) BMC Bioinformatics, 3:30; Lawrence et al. (1993) *Science,* 262, 208-214.); R'MES programs (Schbath S, (1997) *J. Comp. Biol.,* 4, 189-192), the Verbumculus program (Apostolico et al., (2000) Journal of Computational Biology, vol. 7, no. 1/2; Apostolico et al. (2004) *Journal of Computer and Science Technology*, vol. 19, no. 1, pp. 22-41), the YMF program (Sinha et al., (2002) *Nucleic Acids Research*, vol. 30, no. 24, 5549-5560, and Sinha et al. (2000) *Eighth International Conference on Intelligent Systems for Molecular Biology*, San Diego, Calif., 344-354); the AlignACE (Aligns Nucleic Acid Conserved Elements) (Hughes et al (2000), Journal of Molecular Biology; 296(5):1205-14, and Roth et al, (1998) *Nature Biotechnology,* 16(10):939-45, 1998), the BioProspector program (Liu X et al (2001) *Pac. Symp. Biocomput.,* 127-38, the MEME program (Bailey et al (1994) *Proceedings of the Second International Conference on Intelligent Systems for Molecular Biology,* 28-36, AAAI Press); Motif Sampler (Thijs G (2001) et al. *Bioinformatic,* 17(12), 1113-1122, and Thijs G et al. Journal of Computational Biology (special issue Recomb'2001), 9(2), 447-464, 2002), and SUPERPOSITION (Shinozaki D et al., (2003) *Bioinformatics;* 19 Suppl 2:II206-II214).

In one specific embodiment, the Motif Discovery scan (MDscan) program is used to identify DNA-sequence motifs from the set of identified genomic regions (Liu X S et al. (2002) *Nat. Biotechnol.,* 20(8):835-9). In another specific embodiment, the Mogul program, which incorporates multiple algorithms, is used to identify the DNA-sequence motifs (Rust et al. *Int. Conf. on Systems Biology (ISMB*2003), 2003). Additional algorithms have also been described (see Bailey et al. (1994) *Proc. Int. Conf. Intell. Syst. Mol. Biol.,* 2, 28-36. In some embodiments, more than one algorithm is used to identify the DNA-sequence motif.

In another embodiment, the validity of the DNA-sequence motif that is identified is experimentally tested using such approaches as the one-hybrid system or in vitro DNA-binding site selection methods. (See Blackwell T K (1995) *Methods Enzymol.;* 254:604-18; Blackwell et al. (1990) *Science.* 250 (4984):1149-51; Blackwell et al. (1990) *Science.* 250(4984): 1104-10). Additional methods are disclosed in U.S. Patent Application No. 2004/0115794, hereby incorporated by reference in its entirety.

In another embodiment, at least one of the following motif-finding programs is used: AlignACE (Roth, F. P., Hughes, J. D., Estep, P. W. & Church, G. M. Finding DNA regulatory motifs within unaligned noncoding sequences clustered by whole-genome mRNA quantitation. *Nat Biotechnol* 16, 939-45 (1998)), MEME (Bailey, T. L. & Elkan, C. The value of prior knowledge in discovering motifs with MEME. *Proc Int Conf. Intell Syst Mol Biol* 3, 21-9 (1995)), MDscan (Liu, X. S., Brutlag, D. L. & Liu, J. S. An algorithm for finding protein-DNA-binding sites with applications to chromatin-immunoprecipitation microarray experiments. *Nat Biotechnol* 20, 835-9 (2002)), the conservation-based method described in Kellis et al. (Kellis et al. Sequencing and comparison of yeast species to identify genes and regulatory elements. *Nature* 423, 241-54 (2003)), herein referred to as the "Kellis Method", and a new conservation-based method called CONVERGE.

One embodiment of the methods described herein for identifying a set of biologically-active DNA-binding sites for a protein of interest comprises determining if candidate DNA-binding sites are conserved in one or more species different from that of the cell. In a specific embodiment, the method comprises determining if the candidate DNA-binding sites are conserved in the equivalent genomic regions in one or more species. In one embodiment, the different species are classified under the same phylogenetic class as the cell. In another embodiment, the different species are classified under the same order as the cell. In a preferred embodiment, the different species are classified under the same genus as the cell. In another embodiment, the percent sequence identity between the ribosomal RNA of the cell and that of the different species is at least 70%, 75%, 80%, 85%, 90%, 91%, 92%, 93%, 94%, 95%, 96%, 97%, 97.5%, 98%, 99%, 99.5%, 99.8% or 99.9%. In another embodiment, the percent sequence identity between the mtDNA of the cell and that of the different species is at least 70%, 75%, 80%, 85%, 90%, 91%, 92%, 93%, 94%, 95%, 96%, 97%, 97.5%, 98%, 99%, 99.5%, 99.8% or 99.9%. In another embodiment, the average percent sequence identity between the coding regions of the cell and that of the different species is at least 70%, 75%, 80%, 85%, 90%, 91%, 92%, 93%, 94%, 95%, 96%, 97%, 97.5%, 98%, 99%, 99.5%, 99.8% or 99.9%.

In one embodiment, the candidate DNA-binding site is said to be a biologically-active DNA-binding site if a sequence matching the DNA-binding motif is present in the equivalent genomic region. In a specific embodiment, the candidate DNA-binding site is said to be a biologically-active DNA-binding site if a sequence that matches the DNA-binding motif is present in the equivalent genomic region in at least one different species. In one embodiment, two regions of genomic DNA are said to be equivalent if they are orthologous sequences, such as those containing orthologous genes. The term "orthologous genes" refers to gene loci in different species that are sufficiently similar to each other in their nucleotide sequences to suggest that they originated from a common ancestral gene. Orthologous genes arise when a lineage splits into two species, rather than when a gene is duplicated within a genome. Proteins that are orthologs are encoded by genes of two different species, wherein the genes are said to be orthologous. In a related embodiment, two regions are said to be equivalent if they comprise orthologous gene sequences.

In one embodiment, the identification of equivalent, or orthologous, genomic regions may be performed using DNA-alignment programs to compare the identified genomic regions to genomic sequences from another species. In one embodiment, a sequence of at least 50, 100, 200, 400, 600, 800, 1000, 1500, 3000, 5000 or 10000 bases flanking the candidate binding site is used to search for an equivalent genomic regions in the genomic sequence of other species. Programs and algorithms for the alignment and comparison of DNA sequences are well known in the art. In one embodiment, the DNA Block Aligner (DBA) program, part of the GeneWise software set, is used to compare the identified genomic sequence to genomic DNA from another species (See Ewan et al. (2004) GeneWise and Genomewise. *Genome Research* 14: 988-995). Methods for identifying evolutionarily conserved sequences have been described in U.S. Patent Publication Nos. 2003/0017474 and 2003/0119015, the entire contents of which are herein incorporated by reference. Other programs that may be used include the Mauve program (Darling et al. (2004) *Genome Res;* 14(7):1394-403), the OrthoMCL program (Li et al. (2003) *Genome Res.;* 13(9): 2178-89). See also Thomas et al. (2003) *Nature* 14; 424 (6950):788-93.

Nucleic acid sequence homologies between genomic regions may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, Proc. Natl. Acad. Sci. USA 85(8):2444-2448; Altschul et al., 1990, J. Mol. Biol. 215(3): 403-410; Thompson et al., 1994, Nucleic Acids Res. 22(2): 4673-4680; Higgins et al., 1996, methods Enzymol. 266:383-402; Altschul et al., 1990, J. Mol. Biol. 215(3):403-410; Altschul et al., 1993, Nature Genetics 3:266-272). In a specific embodiment, nucleic acid sequence homologies are evaluated using the Basic Local Alignment Search Tool ("BLAST") which is well known in the art (see, e.g., Karlin and Altschul, 1990, Proc. Natl. Acad Sci. USA 87:2267-2268; Altschul et al., 1990, J. Mol. Biol. 215:403-410; Altschul et al., 1993, Nature Genetics 3:266-272; Altschul et al., 1997, Nuc. Acids Res. 25:3389-3402).

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. The scoring matrix used may be the BLOSUM62 matrix (Gonnet et al., 1992, *Science* 256:1443-1445; Henikoff and Henikoff, 1993, *Proteins* 17:49-61). The PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation). The BLAST programs evaluate the statistical significance of all high-scoring segment pairs identified, and preferably selects those segments which satisfy a user-specified threshold of significance, such as a user-specified percent homology. In one embodiment, the statistical significance of a high-scoring segment pair is evaluated using the statistical significance formula of Karlin (see, e.g., Karlin and Altschul, 1990, Proc. Natl. Acad. Sci. USA 87:2267-2268). The parameters used with the above algorithms may be adapted depending on the sequence length and degree of homology studied. In some embodiments, the parameters may be the default parameters used by the algorithms in the absence of instructions from the user.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In one preferred embodiment, the percent identity between two amino acid sequences is determined using the Needleman and Wunsch (J Mol. Biol. (48): 444-453 (1970)) algorithm which has been incorporated into the GAP program in the GCG software package (available at http://www.gcg.com), using either a Blossom 62 matrix or a PAM250 matrix. In yet another embodiment, the percent identity between two nucleotide sequences is determined using the GAP program in the GCG software package (Devereux, J., et al., Nucleic Acids Res. 12(1):387 (1984)) (available at http://www.gcg.com), using a NWSgapdna-CMP matrix. In another embodiment, the percent identity between two amino acid or nucleotide sequences is determined using the algorithm of E. Myers and W. Miller (CABIOS, 4:11-17 (1989)) which has been incorporated into the ALIGN program (version 2.0).

In a specific embodiment, a candidate DNA-binding site is a conserved DNA-binding site if a DNA-binding site corresponding to the DNA-sequence motif of the protein of interest is present within a genomic region in another species that is equivalent to a window of less than 2 kb, 1.5 kb, 1 kb, 800 bp, 600 bp, 500 bp, 400 bp, 300 bp, 200 bp, 150 bp, 100 bp, 80 bp, 60 bp or 50 bp flanking the candidate DNA-binding sites. For example, in an illustrative non-limiting example, in which a candidate DNA-binding site of sequence GGGACCC lies 550 bp upstream of the transcriptional start site of gene X in the cell, where the window is 300 bp and the DNA-sequence motif for the protein of interest is GGGNCCC, then the candidate DNA-binding site would be conserved if any of the sequences GGGACCC, GGGTCCC, GGGGCCC or GGG CCCC were found in the region of the other species equivalent to from 700-400 bp from the transcriptional start site of gene X, since they all match the DNA-sequence motif. Depending on the sequence identity between the two species in the region preceding the window and the transcriptional start site, the region in the second species that is equivalent to the 700-400 bp window from the cell may be shifted relative to the transcriptional start site, such that the equivalent positions may be from 690-390 bp if, for instance, the second species had a 10 bp deletion immediately preceding the transcriptional start site. One skilled in the art would be able to ascertain any such shifts based on the sequence alignments between the two regions.

In a specific embodiment, a candidate DNA-binding site is said to be a conserved DNA-binding site if a DNA-binding site corresponding to the DNA-sequence motif of the protein of interest is present within the promoter of the orthologous gene in another species. In a specific embodiment, a candidate DNA-binding site within the promoter of a gene is said to be a conserved DNA-binding site if a DNA-binding site corresponding to the DNA-sequence motif of the protein of interest is present in the promoter of the orthologous gene in another species, wherein the promoter region comprises from about 5 kb, 4 kb, 3 kb, 2.5 kb, 2 kb, 1.5 kb, 1 kb, 900 bp, 800 bp or 700 bp 5' to the transcriptional start site to about 50 bp, 100 bp, 150 bp, 200 bp, 250 bp, 300 bp, 400 bp, 500 bp, 600 bp, 800 bp or 1000 bp 3' to the transcriptional start site. In another embodiment, the promoter region consists of from about 5 kb, 4 kb, 3 kb, 2.5 kb, 2 kb, 1.5 kb, 1 kb, 900 bp, 800 bp or 700 bp 5' to the transcriptional start site to about 50 bp, 100 bp, 150 bp, 200 bp, 250 bp, 300 bp, 400 bp, 500 bp, 600 bp, 800 bp or 1000 bp 3' to the transcriptional start site. In another embodiment, some or all of the promoter regions may have been experimentally defined, and as a result, the size of the promoter regions between different genes may differ.

IV. Additional Methods

Another aspect of the invention provides methods of identifying agents which alter the set of biologically-active DNA-binding sites for a protein of interest in the genome of a cell. One specific aspect provides a method of identifying an agent which alters the set of biologically-active DNA-binding sites for a protein of interest in the genome of a cell, the method comprising (i) contacting an experimental cell with a candidate agent; (ii) identifying a set of biologically-active DNA-binding sites for a protein of interest in the genome of the cell of step (i) according to any of the methods described herein, thereby generating an experimental set of biologically-active DNA-binding sites; (iii) comparing (1) the experimental set of biologically-active DNA-binding sites to (2) a control set of biologically-active DNA-binding sites for the protein of interest; wherein a candidate agent is identified if the experimental set and the control set differ.

In one embodiment of the methods for identifying an agent, the control set of biologically-active DNA-binding sites to which the experimental set of biologically-active DNA-binding sites is a set of biologically-active DNA-binding sites for the protein of interest in a control cell that has not been contacted with an agent. In one embodiment, the control set of biologically-active DNA-binding sites is the set of biologically-active DNA-binding sites for the protein of interest in a control cell that (a) has been contacted with a different dosage of the agent; (b) has been contacted with a different agent; or (c) a combination thereof. Alternatively, the control set may be derived from the cell or a group of cells prior to contacting with the agent. In some embodiments, the methods comprise contacting a population of cells with the agent, rather than a single cell, with subsequent steps using the population of cells or a subpopulation.

In preferred embodiments, experimental conditions, other than contacting the experimental cell with the agent, are substantially the sane between the experimental cell and the control cell, such as the genotype of the cell, the growth conditions of the cell, conditions for the isolation of chromatin, immunoprecipitation conditions, etc. In one embodiment, the experimental cell is contacted with the agent in vitro, whereas in other embodiments the cell is contacted in vivo. A cell may be contacted in vivo with the agent, for example, by administering the agent to an organism which comprises the cell.

In some embodiments, a cell is contacted with an agent by genetically expressing the agent in the cell, such as by introducing a transgene in the experimental cell which encodes an agent, such as an RNA or a polypeptide agent. The transgene may encode any protein, such as a transcriptional regulator or a protein that regulates the activity of transcriptional regulators, such as a kinase and phosphatase. The transgene may also encode an inhibitory RNA, such as a hairpin RNA, so that the function of the gene to which the hairpin RNA is directed may be knocked down. In some embodiments, the transgene is associated with a disease state.

In some embodiments, the candidate agent is identified if the experimental set and the control set differ by at least one biologically-active DNA-binding site which is present in one set but not in the other. In other embodiments, the candidate agent is identified if at least 2, 3, 4, 5, 10, 20 or 30 of the biologically-active DNA-binding sites are differentially present in one set relative to the other. In another embodiment, the candidate agent is identified if at least 0.5%, 1%, 2%, 3%, 4% or 5% or 10% of the biologically-active DNA-binding sites are differentially present in one set relative to the other.

A related aspect of the invention provides methods of identifying conditions in which a protein of interest differentially binds to the genome of a cell. One specific aspect of the invention provides a method of identifying two sets of conditions in which a protein of interest differentially binds to the genome of a cell, the method comprising: (i) identifying a first set of biologically-active DNA-binding sites for the protein of interest in the genome of a cell according to any of the methods described herein, wherein the cell is exposed to a first set of conditions; (ii) identifying a second set of biologically-active DNA-binding sites for the protein of interest in the genome of a cell according to any of the methods described herein, wherein the cell is exposed to a second set of conditions; and (iii) comparing the first set of biologically-active DNA-binding sites to the second set of biologically-active DNA-binding sites and determining if the two sets differ.

In one embodiment, the set of conditions comprise a set of environmental conditions. The condition may be a physical condition of the environment in which the cell resides, a chemical condition of the environment, and/or a biological condition of the site. Exposure may be for any suitable time. The exposure may be continuous, transient, periodic, sporadic, etc. Physical conditions include any physical state of the sample in which the cell resides. The physical state may be the temperature or pressure of the sample, or an amount or quality of light (electromagnetic radiation) at the site. Alternatively, or in addition, the physical state may relate to an electric field, magnetic field, and/or particle radiation at the site, among others. Chemical conditions include any chemical aspect of the fluid in which the sample populations are disposed. The chemical aspect may relate to the pH, ionic strength, and/or fluid composition such as gas concentrations, among others. If the cell is in an organism, the set of conditions may include diet, physical activity, sexual activity, stress levels or awareness states such as awake vs. sleeping states, and a diseased state, among others.

In another embodiment, the set of conditions comprises a set of biological conditions. Biological conditions include any biological aspect of the shared fluid volume in which cell is disposed, such as nutrients. The biological conditions may also include the presence or absence of growth factors, chemokines or cytokines. The biological aspects may include the presence, absence, concentration, activity, or type of additional cells.

A related aspect of the invention also provides a method of identifying two cell genotypes in which a protein of interest differentially binds to the genome of a cell, the method comprising: (i) identifying a first set of biologically-active DNA-binding sites for the protein of interest in the genome of a cell of a first genotype; (ii) identifying a second set of biologically-active DNA-binding sites for the protein of interest in the genome of a cell of a second genotype; (iii) comparing the first set of biologically-active DNA-binding sites to the second set of biologically-active DNA-binding sites and determining if the two sets differ.

In one embodiment, the genotypes of the cells differs by the genotype of the gene encoding the protein of interest. In other embodiments, the cells differ in the genotypes of multiple genes, one of which may be the protein of interest.

Another aspect of the invention provides a method of identifying at least one pathway that is regulated by a protein of interest in a cell. One specific aspect of the invention provides a method of identifying a pathway that is transcriptionally regulated by a protein of interest in a cell, the method comprising (i) identifying a set of biologically-active DNA-binding sites for a protein of interest in the genome of the cell according to any of the methods described herein; and (ii) identifying at least two candidate genes likely to be regulated by binding of the protein of interest to the set of biologically-active DNA-binding sites identified in (i); wherein a pathway is identified if at least two candidate genes are members of the same pathway.

As used herein, the term "pathway" is intended to mean a set of system components involved in two or more sequential molecular interactions that result in the production of a product or activity. A pathway can produce a variety of products or activities that can include, for example, intermolecular interactions, changes in expression of a nucleic acid or polypeptide, the formation or dissociation of a complex between two or more molecules, accumulation or destruction of a metabolic product, activation or deactivation of an enzyme or binding activity. Thus, the term "pathway" includes a variety of pathway types, such as, for example, a biochemical pathway, a gene expression pathway and a regulatory pathway. Similarly, a pathway can include a combination of these exemplary pathway types.

In one embodiment, the pathway is a biochemical pathway. A biochemical pathway can include, for example, enzymatic pathways that result in conversion of one compound to another, such as in metabolism, and signal transduction pathways that result in alterations of enzyme activity, polypeptide structure, and polypeptide functional activity. Specific examples of biochemical pathways include the pathway by which galactose is converted into glucose-6-phosphate and the pathway by which a photon of light received by the photoreceptor rhodopsin results in the production of cyclic AMP. Numerous other biochemical pathways exist and are well known to those skilled in the art.

In some embodiments, the biochemical pathway is a carbohydrate metabolism pathway, which in a specific embodiment is selected from the group consisting of glycolysis/gluconeogenesis, citrate cycle (TCA cycle), pentose phosphate pathway, pentose and glucuronate interconversions, fructose and mannose metabolism, galactose metabolism, Ascorbate and aldarate metabolism, starch and sucrose metabolism, amino sugars metabolism, nucleotide sugars metabolism, pyruvate metabolism, glyoxylate and dicarboxylate metabolism, propionate metabolism, butanoate metabolism, $C_5$-branched dibasic acid metabolism, inositol metabolism and inositol phosphate metabolism.

In some embodiments, the biochemical pathway is an energy metabolism pathway, which in a specific embodiment is selected from the group consisting of oxidative phosphorylation, ATP synthesis, photosynthesis, carbon fixation, reductive carboxylate cycle ($CO_2$ fixation), methane metabolism, nitrogen metabolism and sulfur metabolism.

In some embodiments, the biochemical pathway is a lipid metabolism pathway, which in a specific embodiment is selected from the group consisting of fatty acid biosynthesis (path 1), fatty acid biosynthesis (path 2), fatty acid metabolism, synthesis and degradation of ketone bodies, biosynthesis of steroids, bile acid biosynthesis, C21-steroid hormone metabolism, androgen and estrogen metabolism, glycerolipid metabolism, phospholipid degradation, prostaglandin and leukotriene metabolism.

In some embodiments, the biochemical pathway is a nucleotide metabolism pathway, which in a specific embodiment is selected from the group consisting of purine metabolism and pyrimidine metabolism.

In some embodiments, the biochemical pathway is an amino acid metabolism pathway, which in a specific embodiment is selected from the group consisting of glutamate metabolism, alanine and aspartate metabolism, glycine, serine and threonine metabolism, methionine metabolism, cysteine metabolism, valine, leucine and isoleucine degradation, valine, leucine and isoleucine biosynthesis, lysine biosynthesis, lysine degradation, arginine and proline metabolism, histidine metabolism, tyrosine metabolism, phenylalanine metabolism, tryptophan metabolism, phenylalanine, tyrosine and tryptophan biosynthesis, urea cycle, beta-Alanine metabolism, taurine and hypotaurine metabolism, aminophosphonate metabolism, selenoamino acid metabolism, cyanoamino acid metabolism, D-glutamine and D-glutamate metabolism, D-arginine and D-ornithine metabolism, D-alanine metabolism and glutathione metabolism.

In some embodiments, the biochemical pathway is a glycan biosynthesis and metabolism pathway, which in a specific embodiment is selected from the group consisting of N-glycans biosynthesis, N-glycan degradation, O-glycans biosynthesis, chondroitin/heparan sulfate biosynthesis, keratan sulfate biosynthesis, glycosaminoglycan degradation, lipopolysaccharide biosynthesis, clycosylphosphatidylinositol(GPI)-anchor biosynthesis, peptidoglycan biosynthesis, glycosphingolipid metabolism, blood group glycolipid biosynthesis—lactoseries, blood group glycolipid biosynthesis—neo-lactoseries, globoside metabolism and ganglioside biosynthesis.

In some embodiments, the biochemical pathway is a biosynthesis of Polyketides and Nonribosomal Peptides pathway, which in a specific embodiment is selected from the group consisting of Type I polyketide structures, biosynthesis of 12-, 14- and 16-membered macrolides, biosynthesis of ansamycins, polyketide sugar unit biosynthesis, nonribosomal peptide structures, and siderophore group nonribosomal peptide biosynthesis.

In some embodiments, the biochemical pathway is a metabolism of cofactors and vitamins pathway, which in a specific embodiment is selected from the group consisting of Thiamine metabolism, Riboflavin metabolism, Vitamin B6 metabolism, Nicotinate and nicotinamide metabolism, Pantothenate and CoA biosynthesis, Biotin metabolism, Folate biosynthesis, One carbon pool by folate, Retinol metabolism, Porphyrin and chlorophyll metabolism and Ubiquinone biosynthesis.

In some embodiments, the biochemical pathway is a biosynthesis of secondary metabolites pathway, which in a specific embodiment is selected from the group consisting of terpenoid biosynthesis, diterpenoid biosynthesis, monoterpenoid biosynthesis, limonene and pinene degradation, indole and ipecac alkaloid biosynthesis, flavonoids, stilbene and lignin biosynthesis, alkaloid biosynthesis I, alkaloid biosynthesis II, penicillins and cephalosporins biosynthesis, beta-lactam resistance, streptomycin biosynthesis, tetracycline biosynthesis, clavulanic acid biosynthesis and puromycin biosynthesis.

In one embodiment, the pathway is a gene expression pathway. A gene expression pathway can include, for example, molecules which induce, enhance or repress expression of a particular gene. A gene expression pathway can therefore include polypeptides that function as repressors and transcription factors that bind to specific DNA sequences in a promoter or other regulatory region of the one or more regulated genes. An example of a gene expression pathway is the induction of cell cycle gene expression in response to a growth stimulus.

In one embodiment, the pathway is a regulatory pathway. A regulatory pathway can include, for example, a pathway that controls a cellular function under a specific condition. A regulatory pathway controls a cellular function by, for example, altering the activity of a system component or the activity of a biochemical, gene expression or other type of pathway. Alterations in activity include, for example, inducing a change in the expression, activity, or physical interactions of a pathway component under a specific condition. Specific examples of regulatory pathways include a pathway that activates a cellular function in response to an environmental stimulus of a biochemical system, such as the inhibition of cell differentiation in response to the presence of a cell growth signal and the activation of galactose import and catalysis in response to the presence of galactose and the absence of repressing sugars. The term "component" when used in reference to a network or pathway is intended to mean a molecular constituent of the biochemical system, network or pathway, such as, for example, a polypeptide, nucleic acid, other macromolecule or other biological molecule.

In one embodiment, the pathway is a signaling pathway. Signaling pathways include MAPK signaling pathways, Wnt signaling pathways, TGF-beta signaling pathways, toll-like receptor signaling pathways, Jak-STAT signaling pathways, second messenger signaling pathways and phosphatidylinositol signaling pathways.

One embodiment of the methods described herein for identifying pathways comprises identifying candidate genes likely to be regulated by the protein of interest. In one embodiment, a candidate gene is likely regulated by the protein of interest if the promoter for the candidate gene comprises at least one of the identified biologically-active DNA-binding sites for the protein of interest. In a specific embodiment, the promoter region of a candidate gene comprises from about 3 kb 5' to 1 kb 3' of the transcription initiation site. In another specific embodiment, the promoter region of a candidate gene comprises from about 2 kb 5' to 0.5 kb 3' of the transcription initiation site. In another embodiment, a candidate gene is likely regulated by the protein of interest if a regulatory element for the candidate gene comprises at least one of the identified biologically-active DNA-binding sites. In one embodiment, the regulatory element is selected from the group consisting of promoter and enhancer regions.

In one embodiment, a candidate gene is likely regulated by the protein of interest if at least one of the identified biologically-active DNA-binding sites is located within about 3 kb 5' to 1 kb 3' of the transcription initiation site for the gene. If a gene has more than one transcription initiation site, then in one embodiment the candidate gene is likely regulated by the protein of interest if at least one of the identified biologically-active DNA-binding sites is located within about 3 kb 5' to 1 kb 3' of at least one of the transcription initiation sites for the gene. In a specific embodiment, at least one of the identified biologically-active DNA-binding sites is located within about 2 kb 5' to 0.5 kb 3' of at least one of the transcription initiation sites for the gene.

In another embodiment, a candidate gene is likely regulated by the protein of interest if at least one of the identified biologically-active DNA-binding sites is located within about 4 kb 5' to 1 kb 3' of the initiator methionine codon for the gene of interest, or where multiple gene products exist which differ in the initiator methionine use, at least one of the identified biologically-active DNA-binding sites is located within about 4 kb 5' to 1 kb 3 or one of the initiator methionine.

Candidate genes may be assigned to pathways by one skilled in the art, for example, by consulting any of several databases which describe the function of genes and their classification into pathways and/or by consulting the literature (See also Biochemical Pathways: An Atlas of Biochemistry and Molecular Biology. Gerhard Michal (Editor) Wiley, John & Sons, Incorporated, (1998); Biochemistry of Signal Transduction and Regulation, Gerhard Krauss, Wiley, John & Sons, Incorporated, (2003); Signal Transduction. Bastien D. Gomperts, Academic Press, Incorporated (2003)). Databases which may be used include, but are not limited to, http://www.genome.jp/kegg/kegg4.html; Pubmed, OMIM and Entrez at http://www.ncbi.nih.gov; the Swiss-Prot database at http://www.expasy.org/.

In one preferred embodiment, a pathway to which a gene has been assigned is identified using the Biomolecular Interaction Network Database (BIND) at http://www.blueprint.org/bind/, and more preferably at http://www.blueprint.org/bind/search/bindsearch.html (See also Bader G D, Betel D, Hogue C W. (2003) BIND: the Biomolecular Interaction Network Database. *Nucleic Acids Res.* 31(1):248-50; and Bader G D, Hogue C W. (2003) An automated method for finding molecular complexes in large protein interaction networks. *BMC Bioinformatics.* 4(1)). One feature of the BIMD database lists the pathways to which a query gene has been assigned, thereby allowing the identification of the pathways to which a gene is assigned. Furthermore, U.S. Patent Publication No. 2003/0100996 describes methods for establishing a pathway database and performing pathway searches which may be used to facilitate the identification of pathways and the classification of genes into pathways.

Another aspect of the invention provides methods of identifying the mechanisms underlying gene regulation. The invention provides methods of identifying the biochemical changes for a protein of interest which correlate with its differential binding to the genome of a cell. One specific aspect of the invention provides a method of identifying a property of a gene product of a gene of interest that correlates with the binding activity of a polypeptide encoded by the gene of interest to the genome of a cell, the method comprising (i) identifying two sets of conditions in which a protein of interest differentially binds to the genome of the cell according to any of the methods described herein; (ii) determining a property of a gene product of the gene of interest in (a) a cell exposed to a first set of conditions; and in (b) a cell exposed to a second set of conditions; and (iii) determining if at least one property of the gene product differs in the two cells of step (ii), thereby identifying a property that correlates with the binding activity of a gene of interest to the genome of a cell.

Another aspect of the invention provides a method of identifying a property of a gene product of a gene of interest that correlates with the binding activity of a polypeptide encoded by the gene of interest to the genome of a cell, the method comprising (i) identifying an agent which alters the set of biologically-active DNA-binding sites for a protein of interest in the genome of a cell according to any of the methods described herein; (ii) determining a property of a gene product of the gene of interest in (a) a cell contacted with the agent; and in (b) a cell not contacted with the agent; and (iii) determining if at least one property of the gene product differs in the two cells of step (ii), thereby identifying a property that correlates with the binding activity of a gene of interest to the genome of a cell.

A related aspect of the invention provides a method of identifying a property of the gene product of a gene of interest that correlates with the binding activity of a polypeptide encoded by the gene of interest to the genome of a cell, the method comprising (i) identifying an agent which alters the set of biologically-active DNA-binding sites for a protein of interest in the genome of a cell according to any of the methods described herein; (ii) determining a property of a gene product of the gene of interest in (a) a cell contacted with dosage of the agent; and in (b) a cell contacted with a different dosage of the agent; and (iii) determining if at least one property of the gene product differs in the two cells of step (ii), thereby identifying a property that correlates with the binding activity of a gene of interest to the genome of a cell. A different dosage of the agent may comprise, for example, exposing the cell to a different concentration of the agent of for a different duration.

In one embodiment of the methods described herein for identifying a property of a gene product, the expression product is an mRNA. In another embodiment, the expression product is a polypeptide.

In one embodiment of the methods described herein for identifying a property of a gene product, the property of the gene product is selected from the group consisting of a post-translational modification of the gene product, expression level of the gene product, enzymatic activity of the gene product, oligomeric state and intracellular localization of the gene product. As used herein, "post-translational modification" refers to addition of a peptidic or non-peptidic moiety to a protein that cannot be considered as the elongation of the peptidic chain of the protein. Exemplary post-translational protein modification include phosphorylation, acetylation, methylation, ADP-ribosylation, ubiquitination, glycosylation, carbonylation, sumoylation, biotinylation or addition of a polypeptide side chain or of a hydrophobic group. In one specific embodiment, the phosphorylation to be assessed is phosphorylation on tyrosine, serine, threonine or histidine residue. In another specific embodiment, the addition of a polypeptide side chain to be assessed is the addition of ubiquitin. Ubiquitination involves the covalent attachment of ubiquitin, an evolutionary highly conserved 76-amino acid polypeptide which is abundantly present in all eukaryotic cells to the 1-amino group of one or more lysine side chains of target proteins. In still another specific embodiment, the addition of a hydrophobic group to be assessed is the addition of a fatty acid, e.g., myristate or palmitate, addition of an isoprenoid, e.g., farnesyl or genranylgenranyl, or addition of a glycosyl-phosphatidyl inositol anchor, e.g., a carbohydrate group comprises glycosyl.

Phosphorylation can include phosphorylation of a tyrosine, serine, threonine or histidine. Antibodies that can be used to detect these modifications can include phosphotyrosine-specific antibody, phosphoserine-specific antibody, phosphoserine-specific antibody, and phospho-threonine-proline antibody, for example. Antibodies that can be used to detect these modifications also include an antibody specific to a phosphorylated residue of a protein such as phosphorylated c-Jun at Ser 73. Acetylation can be detected by using an acetylated-lysine antibody. Methylation specific antibodies can be used to detect proteins having a methylation on one or more amino acids. ADP-ribosylation specific antibodies can be used to detect proteins having an ADP ribosylation modification. An example of addition of a polypeptide chain is ubiquitination. Detection of ubiquitination on a target protein can be made using an ubiquitin-specific antibody or poly-ubiquitin-specific antibody for example.

Any general method known to one skilled in the art may be applied to determine the expression level of a gene product, such as determining mRNA levels or protein levels. Levels of mRNA may be determined, for example, using such techniques as Northern Blots, reverse-transcriptase polymerase chain reaction (RT-PCR), RNA protection assays or a DNA microarray comprising probes capable of hybridizing to at least a portion of the mRNA. Likewise, protein levels may be quantitated using techniques well-known in the art, such as western blotting, immuno-sandwich assays, ELISA assays, or any other immunological technique. Techniques for quantitating nucleic acids and proteins may be found, for example, in Molecular Cloning: A Laboratory Manual, 3rd Ed., ed. by Sambrook and Russell (Cold Spring Harbor Laboratory Press: 2001); and in Current Protocols in Cell Biology, ed. by Bonifacino, Dasso, Lippincott-Schwartz, Harford, and Yamada, John Wiley and Sons, Inc., New York, 1999, hereby incorporated by reference in their entirety.

The intracellular localization of a protein may be determined by immunocytochemistry. Alternatively, organelles from the cells may be purified and the presence of the polypeptide in different organelle preparations determined. Alternatively, the protein of interest may be fused to a fluorescent protein to allow in vivo live imaging of the intracellular localization of the protein. Exemplary fluorescent proteins include the green fluorescent protein (GFP), DsRed, zFP538, mRFP1, BFP, CFP, YFP, mutants thereof, or functionally-active fragments thereof. GFP is described in U.S. Pat. No. 5,491,084, while zFP538 is described in Zagranichny et al. Biochemistry. 2004; 43(16):4764-72. Subcellular compartments include but are not limited to, nucleus, endoplasmic reticulum (ER), Golgi apparatus, coated pits, mitochondria, endosomes, and cytoplasm. The intracellular localization of an mRNA molecular may also be determined using in-situ hybridization techniques on fixed cell samples.

In one embodiment where the gene product is an enzyme, the enzymatic activity of the gene product is the property of the gene product. Enzymatic activity of a gene product may be determined using standard assays for that particular type of enzyme (see for example Enzymes: A Practical Introduction to Structure, Mechanism, and Data Analysis, by Robert Allen Copeland; Wiley, John & Sons, Incorporated, 2000; and Enzyme Kinetics: Behavior and Analysis of Rapid Equilibrium and Steady-State Enzyme Systems; by Irwin H. Segel; Wiley, John & Sons, Incorporated (1994)).

In one embodiment of the methods described herein for identifying a property of a gene product, the property of the gene product is the oligomeric state of the polypeptide gene product. Oligomeric state refers to whether the protein of interest exists as a monomer, dimer, trimer, hexamer or other type of multimeric state. The oligomeric state of a protein of interest may be determined, for example, using non-denaturing polyacrylamide gel electrophoresis (PAGE) or gel filtration chromatography to assess the size of a complex containing the proteins of interest.

In some embodiments of the methods described herein, determining if at least one property of the gene product differs in the two cells comprise determining if the property of the gene differs by a qualitative measure. In other embodiments, it comprises determining if it differs by a qualitative measure, such as by at least 10%, 20%, 40%, 50%, 75%, 100% or 200%.

In some embodiments, the property of a protein gene product comprises a physical property, such as its molecular weight, its isoelectric point, its amino acid composition, its amino acid sequence, its dimerization state e.g. monomer, dimmer, tetramer, etc., or its association with other polypeptides to form a complex. Any techniques known in the art, such as mass spectrometry, SDS-PAGE, isoelectric focusing, peptide sequencing, gel filtration and immunoprecipitation may be used to measure these properties.

In some embodiments of the ongoing methods, an increase in a property of the gene product correlates with an increase in the number of biologically-active DNA-binding sites bound by the protein of interest, while in other embodiments it correlates with a decrease in the number of biologically-active DNA-binding sites bound by the protein of interest. In other embodiments, a change in the property of the gene product correlates with a change in the biologically-active DNA-binding sites without altering the total number of sites.

In some preferred embodiments, the cells are tested in more than two conditions, or under more than two candidate agents, such that a correlation may be extended to additional conditions or candidate agents.

V. Candidate Agents

In some embodiments of the methods described herein, the candidate agent comprises a small molecule drug, an antisense nucleic acid, an antibody, a peptide, a ligand, a fatty acid, a hormone or a metabolite.

Exemplary compounds that may be used as candidate agents (e.g., a single compound, a combination of two or more compounds, a library of compounds) include nucleic acids, peptides, polypeptides, peptidomimetics, antibodies, antisense oligonucleotides, RNAi constructs (including siRNAs), ribozymes, chemical compounds, and small organic molecules. Compounds may be screened individually, in combination, or as a library of compounds. Without being bound by theory, the invention contemplates that the modulation of cellular phenotypes may involve the activation or inhibition of particular genes and signaling pathways which modulate proliferation, survival, or differentiation along a particular lineage, thereby modulating a cellular phenotype.

Candidate agents can be screened individually, in combination with one or more other compounds, or as a library of compounds. Compounds include nucleic acids, peptides, polypeptides, peptidomimetics, RNAi constructs, antisense oligonucleotides, ribozymes, antibodies, and small molecules.

Antisense oligonucleotides are relatively short nucleic acids that are complementary (or antisense) to the coding strand (sense strand) of the mRNA encoding a particular protein. Although antisense oligonucleotides are typically RNA based, they can also be DNA based. Additionally, antisense oligonucleotides are often modified to increase their stability.

Without being bound by theory, the binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding a specific protein. Accordingly, antisense oligonucleotides decrease the expression and/or activity of a particular protein.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or compounds facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. W088/09810, published Dec. 15, 1988) or the blood-brain barrier (see, e.g., PCT Publication No. W089/10134, published Apr. 25, 1988), hybridization-triggered cleavage agents (See, e.g., Krol et al., 1988, BioTechniques 6:958-976) or intercalating agents. (See, e.g., Zon, 1988, Pharm. Res. 5:539-549). To this end, the oligonucleotide may be conjugated to another molecule.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl)uracil, (acp3)w, and 2,6-diaminopurine.

The antisense oligonucleotide may also comprise at least one modified sugar moiety selected from the group including but not limited to arabinose, 2-fluoroarabinose, xylulose, and hexose. The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an -anomeric oligonucleotide. An -anomeric oligonucleotide forms specific double-stranded hybrids with complementary RNA in which, contrary to the usual-units, the strands run parallel to each other (Gautier et al., 1987, Nucl. Acids Res. 15:6625-6641). The oligonucleotide is a 2'-0-methylribonucleotide (Inoue et al., 1987, Nucl. Acids Res. 15:6131-6148), or a chimeric RNA-DNA analogue (Inoue et al., 1987, FEBS Lett. 215:327-330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451), etc.

The selection of an appropriate oligonucleotide can be readily performed by one of skill in the art. Given the nucleic acid sequence encoding a particular protein, one of skill in the art can design antisense oligonucleotides that bind to that protein, and test these oligonucleotides in an in vitro or in vivo system to confirm that they bind to and mediate the degradation of the mRNA encoding the particular protein. To design an antisense oligonucleotide that specifically binds to and mediates the degradation of a particular protein, it is important that the sequence recognized by the oligonucleotide is unique or substantially unique to that particular protein. For example, sequences that are frequently repeated across protein may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for a particular protein.

In another example, it may be desirable to design an antisense oligonucleotide that binds to and mediates the degradation of more than one message. In one example, the messages may encode related protein such as isoforms or functionally redundant protein. In such a case, one of skill in the art can align the nucleic acid sequences that encode these related proteins, and design an oligonucleotide that recognizes both messages.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense sufficient to suppress translation on endogenous mRNAs in certain instances. Therefore another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290: 304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al, 1982, Nature 296:39-42), etc. Any type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve mRNA degradation, however the biochemical mechanisms are currently an active area of research. Despite some mystery regarding the mechanism of action, RNAi provides a useful method of inhibiting gene expression in vitro or in vivo.

As used herein, the term "dsRNA" refers to siRNA molecules, or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

As used herein, the term "RNAi construct" is a generic term used throughout the specification to include small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmcokinetic properties. For example, the phosphodiester linkages of natural RNA may be modified to include at least one of an nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) Proc Natl Acad Sci USA, 98:9742-9747; Elbashir, et al. (2001) EMBO J, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the Drosophila in vitro system is used. In this embodiment, dsRNA is combined with a soluble extract derived from Drosophila embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain preferred embodiments, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In other embodiments, the RNAi construct is in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., *Genes Dev,* 2002, 16:948-58; McCaffrey et al., *Nature,* 2002, 418:38-9; McManus et al., *RNA,* 2002, 8:842-50; Yu et al., *Proc Natl Acad Sci USA,* 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an exemplary vector for bi-directional transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO01/68836 and WO01/75164.

Ribozyme molecules designed to catalytically cleave an mRNA transcript can also be used to prevent translation of mRNA (See, e.g., PCT International Publication WO90/11364, published Oct. 4, 1990; Sarver et al., 1990, Science 247:1222-1225 and U.S. Pat. No. 5,093,246). While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585-591.

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al., 1984, Science, 224:574-578; Zaug and Cech, 1986, Science, 231:470-475; Zaug, et al., 1986, Nature, 324:429-433; published International patent application No. WO88/04300 by University Patents Inc.; Been and Cech, 1986, Cell, 47:207-216). The Cech-type ribozymes have an eight base pair active site that hybridizes to a target RNA sequence whereafter cleavage of the target RNA takes place. The invention encompasses those Cech-type ribozymes that target eight base-pair active site sequences.

As in the antisense approach, the ribozymes can be composed of modified oligonucleotides (e.g., for improved stability, targeting, etc.) and can be delivered to cells in vitro or in vivo. A preferred method of delivery involves using a DNA construct "encoding" the ribozyme under the control of a strong constitutive pol III or pol II promoter, so that transfected cells will produce sufficient quantities of the ribozyme to destroy targeted messages and inhibit translation. Because ribozymes unlike antisense molecules, are catalytic, a lower intracellular concentration is required for efficiency.

Antibodies can be used as inhibitors of the activity of a particular protein. Antibodies can have extraordinary affinity and specificity for particular epitopes. Antibodies that bind to a particular protein in such a way that the binding of the antibody to the epitope on the protein can interfere with the function of that protein. For example, an antibody may inhibit the function of the protein by sterically hindering the proper protein-protein interactions or occupying active sites. Alternatively the binding of the antibody to an epitope on the particular protein may alter the conformation of that protein such that it is no longer able to properly function.

Monoclonal or polyclonal antibodies can be made using standard protocols (See, for example, Antibodies: A Laboratory Manual ed. by Harlow and Lane (Cold Spring Harbor Press: 1988)). A mammal, such as a mouse, a hamster, a rat, a goat, or a rabbit can be immunized with an immunogenic form of the peptide. Techniques for conferring immunogenicity on a protein or peptide include conjugation to carriers or other techniques well known in the art.

Following immunization of an animal with an antigenic preparation of a polypeptide, antisera can be obtained and, if desired, polyclonal antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies End Cancer Therapy, Alan R. Liss, Inc. pp. 77-96). Hybridoma cells can be screened immunochemically for production of antibodies specifically reactive with a particular polypeptide and monoclonal antibodies isolated from a culture comprising such hybridoma cells.

The term antibody as used herein is intended to include fragments thereof which are also specifically reactive with a particular polypeptide. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific and chimeric molecules having affinity for a particular protein conferred by at least one CDR region of the antibody.

Both monoclonal and polyclonal antibodies (Ab) directed against a particular polypeptides, and antibody fragments such as Fab, F(ab)$_2$, Fv and scfv can be used to block the action of a particular protein. Such antibodies can be used either in an experimental context to further understand the role of a particular protein in a biological process, or in a therapeutic context.

Peptides, polypeptides, variants polypeptides, and peptide fragments can be candidate agents. Exemplary polypeptides comprise an amino acid sequence at least 60%, 70%, 75%, 80%, 85%, 90%, 95%, 98%, 99%, or 100% identical to a particular polypeptide. Exemplary fragments include fragments of at least 5, 6, 7, 8, 9, 10, 15, 20, 25, 50, 75, 100, 125, 150, 200, 250, or greater than 250 amino acid residues of the full length polypeptide. Peptides and polypeptides can either agonize or antagonize the function of a particular protein, and thereby modulate the phenotype of a cell.

Small organic molecules can either agonize or antagonize the expression and/or activity of a particular protein, and thereby modulate the phenotype of a cell. By small organic molecule is meant a carbon contain molecule having a molecular weight less than 2500 amu, more preferably less than 1500 amu, and even more preferably less than 750 amu. In the context of the present invention, such small organic molecules would be able to promote the differentiation of a cell to a particular differentiated cell type.

Small molecules can be readily identified by screening libraries of organic molecules and/or chemical compounds to identify those compounds that have a desired function. Without being bound by theory, small organic molecules may influence a cellular phenotype in any of a number of ways. By way of example, small molecules may act at the cell surface to influence cell surface receptors. By way of further example, small molecules may act intracellularly to influence intracellular signaling along a particular signaling pathway. The methods of the present invention are unbiased and allow identification of small molecule compounds that modulate a cellular phenotype regardless of its mechanism of action.

In addition to compounds which are peptides or polypeptides, the invention contemplates nucleic acids comprising nucleotide sequences encoding peptides and polypeptides. The term nucleic acid as used herein is intended to include equivalents. The term equivalent is understood to include nucleotide sequences which are functionally equivalent to a particular nucleotide sequence. Equivalent nucleotide sequences will include sequences that differ by one or more nucleotide substitutions, additions or deletions, such as allelic variants, and variation due to degeneracy of the genetic code. Equivalent sequences may also include nucleotide sequences that hybridize under stringent conditions (i.e., equivalent to about 20-27° C. below the melting temperature ($T_m$) of the DNA duplex formed in about 1M salt) to a given nucleotide sequence. Further examples of stringent hybridization conditions include a wash step of 0.2×SSC at 65° C.

Nucleic acids having a sequence that differs from nucleotide sequences which encode a particular peptide or polypeptide candidate agent due to degeneracy in the genetic code are also within the scope of the invention. Such nucleic acids encode functionally equivalent peptides but differ in sequence from wildtype sequences known in the art due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence. However, it is expected that DNA sequence polymorphisms that do lead to changes in the amino acid sequences will also exist.

Biological conditions include any biological aspect of the shared fluid volume in which the cell populations are disposed. The biological aspects may include the presence, absence, concentration, activity, or type of cells, viruses, vesicles, organelles, biological extracts, and/or biological mixtures, among others. The assays described herein may screen a library of conditions to test the activity of each library member on a set of cell populations. A library generally comprises a collection of two or more different members. These members may be chemical modulators (or candidate modulators) in the form of molecules, ligands, compounds, transfection materials, receptors, antibodies, and/or cells (phages, viruses, whole cells, tissues, and/or cell extracts), among others, related by any suitable or desired common characteristic. This common characteristic may be "type." Thus, the library may comprise a collection of two or more compounds, two or more different cells, two or more different antibodies, two or more different nucleic acids, two or more different ligands, two or more different receptors, or two or more different phages or whole cell populations distinguished by expressing different proteins, among others. This common characteristic also may be "function." Thus, the library may comprise a collection of two or more binding partners (e.g., ligands and/or receptors), agonists, or antagonists, among others, independent of type.

Library members may be produced and/or otherwise generated or collected by any suitable mechanism, including chemical synthesis in vitro, enzymatic synthesis in vitro, and/or biosynthesis in a cell or organism. Chemically and/or enzymatically synthesized libraries may include libraries of compounds, such as synthetic oligonucleotides (DNA, RNA, peptide nucleic acids, and/or mixtures or modified derivatives thereof), small molecules (about 100 Da to 10 KDa), peptides, carbohydrates, lipids, and/or so on. Such chemically and/or enzymatically synthesized libraries may be formed by directed synthesis of individual library members, combinatorial synthesis of sets of library members, and/or random synthetic approaches. Library members produced by biosynthesis may include libraries of plasmids, complementary DNAs, genomic DNAs, RNAs, viruses, phages, cells, proteins, peptides, carbohydrates, lipids, extracellular matrices, cell lysates, cell mixtures, and/or materials secreted from cells, among others. Library members may be contact arrays of cell populations singly or as groups/pools of two or more members.

EXEMPLIFICATION

The invention now being generally described, it will be more readily understood by reference to the following examples, which are included merely for purposes of illustration of certain aspects and embodiments of the present invention, and are not intended to limit the invention, as one skilled in the art would recognize from the teachings herein-above and the following examples, that other DNA microarrays, transcriptional regulators, cell types, antibodies, ChIP conditions, or data analysis methods, all without limitation, can be employed, without departing from the scope of the invention as claimed. The practice of the present invention will employ, where appropriate and unless otherwise indicated, conventional techniques of cell biology, cell culture, molecular biology, transgenic biology, microbiology, virology, recombinant DNA, and immunology, which are within the skill of the art. Such techniques are described in the literature. See, for example, Molecular Cloning: A Laboratory Manual, 3rd Ed., ed. by Sambrook and Russell (Cold Spring Harbor Laboratory Press: 2001); the treatise, Methods In Enzymology (Academic Press, Inc., N.Y.); Using Antibodies, Second Edition by Harlow and Lane, Cold Spring Harbor Press, New York, 1999; Current Protocols in Cell Biology, ed. by Bonifacino, Dasso, Lippincott-Schwartz, Harford, and Yamada, John Wiley and Sons, Inc., New York, 1999; and PCR Protocols, ed. by Bartlett et al., Humana Press, 2003.

Various publications, patents, and patent publications are cited throughout this application, the contents of which are incorporated herein by reference in their entirety.

Experimental Procedures:

The following procedures were followed for the experimental examples.

Genetic Reagents

The 203 transcriptional regulators were identified by searching the YPD and MIPS databases for known and predicted transcription factors and nucleic acid binding proteins (Mewes, H. W., Albermann, K., Heumann, K., Liebl, S. & Pfeiffer, F. MIPS: a database for protein sequences, homology data and yeast genome information. *Nucleic Acids Res* 25, 28-30 (1997); Hodges, P. E., McKee, A. H., Davis, B. P., Payne, W. E. & Garrels, J. I. The Yeast Proteome Database (YPD): a model for the organization and presentation of genome-wide functional data. *Nucleic Acids Res* 27, 69-73 (1999); Costanzo, M. C. et al. YPD, PombePD and WormPD: model organism volumes of the BioKnowledge library, an integrated resource for protein information. *Nucleic Acids Res* 29, 75-9 (2001)). Yeast strains were created for each of the 203 regulators in which a repeated Myc epitope coding sequence was integrated into the endogenous gene encoding the regulator. PCR constructs containing the Myc epitope coding sequence and a selectable marker flanked by regions of homology to either the 5' or 3' end of the targeted gene were transformed into the W303 yeast strain Z1256. Genomic integration and expression of the epitope-tagged protein were confirmed by PCR and Western blotting, respectively.

Growth Conditions

Regulators were selected for profiling in a specific environment if they were essential for growth in that environment or if there was other evidence implicating them in regulation of gene expression in that environment.

A brief description of the environmental conditions used follows:

Rich media. Cells were grown in YPD (1% yeast extract/2% peptone/2% glucose) to an OD600 of ~0.8.

Highly hyperoxic. Cells were grown in YPD to an OD600 of ~0.5 followed by treatment with hydrogen peroxide (4 mM final) for 30 minutes.

Moderately hyperoxic. Cells were grown in YPD to an OD600 of ~0.5 followed by treatment with hydrogen peroxide (0.4 mM final) for 20 minutes.

Amino acid starvation. Cells were grown to an OD600 of ~0.6 in synthetic complete medium followed by treatment with the inhibitor of amino acid biosynthesis sulfometuron methyl (0.2 μg/ml final) for two hours.

Nutrient deprived. Cells were grown in YPD to an OD600 of ~0.8 followed by treatment with rapamycin (100 nM final) for 20 minutes.

Filamentation inducing. Cells were grown in YPD containing 1% butanol for either 90 minutes or 14 hours (corresponding to an OD600 of ~0.8).

Mating inducing. Cells were grown in YPD to an OD600 of ~0.8 followed by treatment with the alpha factor pheromone (5 μg/ml) for 30 minutes.

Elevated temperature. Cells were grown in YPD at 30° C. to an OD600 of ~0.5 followed by a temperature shift to 37° C. for 45 minutes.

Galactose medium. Cells were grown in YEP medium supplemented with galactose (2%) to an OD600 of ~0.8.

Raffinose medium. Cells were grown in YEP medium supplemented with raffinose (2%) to an OD600 of ~0.8.

Acidic medium. Cells were grown in YPD to an OD600 of ~0.5 followed by treatment for 30 minutes with succinic acid (0.05 M final) to reach a pH of 4.0.

Phosphate deprived medium. Cells were grown in synthetic complete medium lacking phosphate to a final OD600 of ~0.8.

Vitamin deprived medium. Cells were grown in synthetic complete medium lacking thiamine to a final OD600 of ~0.8.

Strain Information

For each of the 203 regulators, strains were generated in which a repeated Myc epitope coding sequence was integrated into the endogenous gene encoding the regulator. Polymerase chain reaction (PCR) constructs containing the Myc epitope coding sequence and a selectable marker flanked by regions of homology to either the 5' or 3' end of the targeted gene were transformed into the W303 yeast strain Z1256. Genomic integration and expression of the epitope-tagged protein were confirmed by PCR and Western blotting, respectively.

Genome-Wide Location Analysis

Genome-wide location analysis was performed as previously described (Orlando, V. Mapping chromosomal proteins in vivo by formaldehyde-crosslinked-chromatin immunoprecipitation. *Trends Biochem Sci* 25, 99-104 (2000); Tessier, D. et al. *A DNA Microarrays Fabrication Strategy for Research Laboratories*. (eds. Rehm, H. & Reed, G.) (Wiley-VCH, Weinheim, Germany, 2002)). Bound proteins were formaldehyde-crosslinked to DNA in vivo, followed by cell lysis and sonication to shear DNA. Crosslinked material was immunoprecipitated with an anti-myc antibody, followed by reversal of the crosslinks to separate DNA from protein. Immunoprecipitated DNA and DNA from an unenriched sample were amplified and differentially fluorescently labelled by ligation-mediated PCR. These samples were hybridized to a microarrray consisting of spotted PCR products representing the intergenic regions of the *S. cerevisiae* genome. Relative intensities of spots were used as the basis for an error model that assigns a probability score (P value) to binding interactions. All microarray data is available from ArrayExpress (accession number: E-WMIT-10) as well as from the authors' web site.

Growth Environments

Applicants profiled all 203 regulators in rich medium. In addition, Applicants profiled 84 regulators in at least one other environmental condition. The list of regulators is given in Table 1.

Microarray Design

Using the Yeast Intergenic Region Primer set (Research Genetics) Applicants PCR amplified and printed approximately 6000 DNA fragments, representing essentially all of the known intergenic regions in the yeast genome (Tessier, D. et al. *A DNA Microarrays Fabrication Strategy for Research Laboratories*. (eds. Rehm, H. & Reed, G.) (Wiley-VCH, Weinheim, Germany, 2002)). The average size of the spotted PCR products was 480 bp, and the sizes ranged from 60 bp to 1500 bp.

Raw Data Analysis

The microarrays were scanned using an Axon200B scanner, and the images were analyzed with Genepix 5.0. Columns corresponding to the background subtracted intensities and standard deviation of the background were extracted for further analysis. The intensities for the two channels, representing the immunoprecipitated (test) and unenriched (control) samples, were normalized by using the median of each channel to calculate a normalization factor, normalizing all datasets to a single median intensity. The log ratio of the intensity in the test channel to the control channel was calculated. To account for biases in the immunoprecipitation reaction, these log ratios were normalized for each spot by subtracting the average log ratio of each spot across all arrays. The intensities in the test channel were then adjusted to yield this normalized ratio. Finally, an error model (Hughes et al. (2000) *Cell* 102, 109-26) was used to calculate significance of enrichment on each chip and to combine data for replicates to obtain a final average ratio and significance of enrichment for each intergenic region. Each intergenic region was assigned to the genes it is most likely to regulate, as described on the author's website.

Applicants have included new refinements in our analysis relative to that used in Lee et al. *Science* 298, 799-804. (2002). Notably, Applicants have excluded artefactual spots from analysis, selected more reliable probes for normalization and assigned quality metrics to individual arrays to identify low quality experiments.

Error Estimates

Applicants previously estimated a false positive rate of 6-10% for genome-wide binding data that meets a $P \leq 0.001$ threshold. The present study is focused on DNA regions that are both bound ($P \leq 0.001$) and contain a conserved match to a binding site specificity. Of 47 sites that were used by Lee et al. Science 298, 799-804. (2002), to determine the error rate and that met our criteria for binding sites, 45 were confirmed by independent gene-specific ChIP experiments. Thus, the frequency of false positives in this dataset is likely to be approximately 4%.

The false negative rate is more difficult to estimate, but it is likely to be approximately 24% in the present genome location dataset. This estimate was derived by determining the number of binding interactions reported in the literature for cell cycle regulators that were not identified in the genome-wide location data at $P \leq 0.001$ and associated with conserved binding sites (12/50). Applicants selected the cell cycle literature for analysis because of the extensive study of this group of regulators and their targets.

Regulator Binding Specificity

Figure 6:
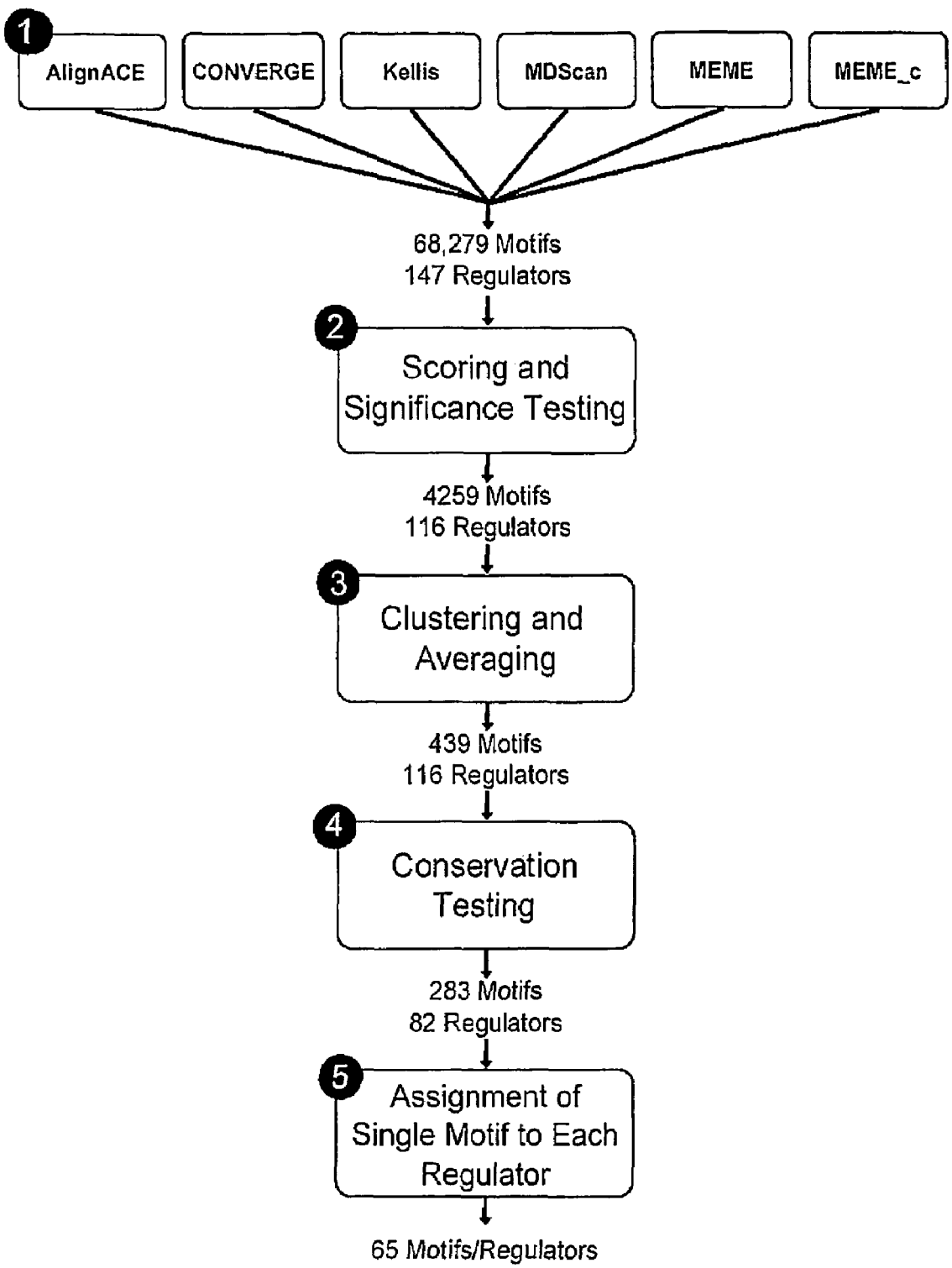
FIG. 6 shows an overview of motif discovery and assignment. Motifs were identified by applying a suite of motif discovery programs to the intergenic sequences identified by the binding data. The resulting specificity predictions were filtered for significance and then clustered to yield representative motifs. Conservation-based metrics were used to identify the highest-confidence subset of these motifs. For cases in which multiple significant binding motifs were found for a factor, Applicants used statistical scores or information from specificity databases to choose a single motif for each regulator. A complete description of the method can be found in experimental procedures.

The putative specificities of regulators were identified by applying a suite of motif discovery programs to the intergenic sequences identified by the binding data. The resulting specificity predictions were filtered for significance using uniform metrics and then clustered to yield representative motifs (FIG. 6). Applicants used six methods to identify the specific sequences bound by regulators: AlignACE11, MEME13, MDscan12, the method of Kellis et al. and two additional new methods that incorporate conservation data: MEME_c and CONVERGE. MEME_c uses the existing MEME program without change, but applies it to a modified set of sequences in which bases that are not conserved in the sensu stricto *Saccharomyces* species were replaced with the letter "N". CONVERGE is a novel expectation-maximization (EM)-based algorithm for discovering specificities using sequence information from multiple genomes. Rather than searching for sites that are identical across the sensu stricto species, as is the case for MEME_c, CONVERGE searches for loci where all aligned sequences are consistent with the same specificity model.

Each of the programs Applicants used attempts to measure the significance of its results with one or more statistical scores. However, Applicants observed that these programs report results with high scores even when applied to random selections of intergenic regions. To distinguish the true motifs, Applicants chose a set of statistical measures as described in the experimental procedures, and Applicants converted these scores into the empirical probability that a motif with a similar score could be found by the same program in randomly selected sequences. To estimate these P values, Applicants ran each program 50 times on randomly selected sets of sequences of various sizes. Applicants accepted only those motifs that were judged to be significant by these scores ($P \leq 0.001$).

Significant motifs from all programs were pooled together and clustered using a k-medoids algorithm. Aligned motifs within each cluster were averaged together to produce consensus motifs and filtered according to their conservation. This procedure typically produced several distinct consensus motifs for each regulator. To choose a single specificity for each regulator, Applicants compared the results with information in the TRANSFAC27, YPD28, and SCPD29 databases. When no prior information was available, Applicants chose the specificity with the most significant statistical score.

Motif Discovery Overview

Binding motifs were identified in a five-step process described in detail below and summarized in FIG. 6. First, motifs were discovered by applying a suite of motif discovery programs to the intergenic sequences identified by the binding data. The resulting specificity predictions were filtered for significance using uniform metrics and then clustered to yield representative motifs. Conservation-based metrics were used to identify the highest-confidence subset of these motifs. For cases in which multiple significant binding motifs were found for a factor, Applicants used statistical scores or information from the Transfac (Matys, V. et al. TRANSFAC: transcriptional regulation, from patterns to profiles. *Nucleic Acids Res* 31, 374-8 (2003)), YPD (Csank, C. et al. Three yeast proteome databases: YPD, PombePD, and CalPD (MycoPathPD). *Methods Enzymol* 350, 347-73 (2002)), and SCPD (Zhu, J. & Zhang, M. Q. SCPD: a promoter database of the yeast *Saccharomyces cerevisiae*. *Bioinformatics* 15, 607-11 (1999)) databases to choose a single motif for each regulator.

Sequence input files, intermediate motif discovery output, and matrix representations of the finalized motifs are available on the authors' website.

Step 1: Initial Motif Discovery

Motif Discovery Programs have different strengths with respect to finding specificities. To gain as comprehensive an analysis as possible, Applicants applied five different motif-finding programs to the binding data: AlignACE (Roth, F. P., Hughes, J. D., Estep, P. W. & Church, G. M. Finding DNA regulatory motifs within unaligned noncoding sequences clustered by whole-genome mRNA quantitation. *Nat Biotechnol* 16, 939-45 (1998)), MEME (Bailey, T. L. & Elkan, C. The value of prior knowledge in discovering motifs with MEME. *Proc Int Conf Intell Syst Mol Biol* 3, 21-9 (1995)), MDscan (Liu, X. S., Brutlag, D. L. & Liu, J. S. An algorithm for finding protein-DNA-binding sites with applications to chromatin-immunoprecipitation microarray experiments. *Nat Biotechnol* 20, 835-9 (2002)), the conservation-based method described in Kellis et al. (Kellis, M., Patterson, N., Endrizzi, M., Birren, B. & Lander, E. S. Sequencing and comparison of yeast species to identify genes and regulatory elements. *Nature* 423, 241-54 (2003)), and a new conservation-based method called CONVERGE (described below). The MEME program was also used to analyze a modified input that incorporated conservation information (see "Probe Sequences").

To make the search more thorough, each of these programs was run multiple times with different parameters. AlignACE was run using the default settings ten times with different random number seeds, in order to increase the motif space it sampled. The results from the AlignACE runs were grouped together for analysis. MEME was run using the supplied $5^{th}$-order Markov background model, the "ZOOPS" motif model, and the "-minsites 20-DNA-revcomp" options. MEME runs were repeated using motif width ranges of 7 to 11 and 12 to 18. To run MDscan, sequences were ranked according the P-value of binding, and the program was mn with the "-s 30-r 5-t 10" options. To compensate for the fact that MDscan searches only for motifs of fixed width, the program was run repeatedly, once with each width in the range 8 to 15 bases. The method of Kellis et al. was applied to the data as described (Kellis, M., Patterson, N., Endrizzi, M., Birren, B. & Lander, E. S. Sequencing and comparison of yeast species to identify genes and regulatory elements. *Nature* 423, 241-54 (2003)). CONVERGE was run twice using motif widths of 8 and 15.

MEME_c

Applicants tested whether Applicants could improve the performance of AlignACE, MEME and MDscan by modifying the input sequences to convey the conservation of each base in the sensu stricto *Saccharomyces* species. Using ClustalW (Thompson, J. D., Higgins, D. G. & Gibson, T. J. CLUSTAL W: improving the sensitivity of progressive multiple sequence alignment through sequence weighting, position-specific gap penalties and weight matrix choice. *Nucleic Acids Res* 22, 4673-80 (1994)) alignments for the sensu stricto species (Kellis, M., Patterson, N., Endrizzi, M., Birren, B. & Lander, E. S. Sequencing and comparison of yeast species to identify genes and regulatory elements. *Nature* 423, 241-54 (2003)), Applicants replaced a base in the *Saccharomyces* genome with the letter "N" if it was not conserved in ⅔ or ¾ of the other genomes. Of the programs tested, only MEME was able to use the modified sequences.

Converge

Applicants designed CONVERGE to identify motifs that are both over-represented in a set of input sequences and conserved across multiple genomes. CONVERGE input sequences consists of an ungapped DNA sequence corresponding to the primary genome, as well as one or more optional aligned sequences, which may contain gaps. The algorithm is based on the ZOOPS model of MEME and uses a $5^{th}$-order Markov background model. However, whereas MEME searches for matches to a motif model across a set of input sequences, CONVERGE searches across the multiple-sequence alignments for each sequence. Specifically, CONVERGE treats the probability of a motif occurring at a site in the alignment as the product of the probabilities of the motif occurring at the same site in each of the aligned sequences. Thus, CONVERGE defines a site as conserved in a flexible manner that depends on the motif being discovered. Full details will be presented elsewhere.

Probe Sequences

Motif discovery programs were applied to the sequences of probes bound with a P-value≦0.001. Applicants found that some intergenic regions were highly homologous over their entire length, and consequently skew the results of motif discovery since all subsequences are overrepresented. To remove this bias, BLAST (Altschul, S. F., Gish, W., Miller, W., Myers, E. W. & Lipman, D. J. Basic local alignment search tool. *J Mol Biol* 215, 403-10 (1990)) was used to identify pairs of probes with high sequence similarity over 50% of their lengths. For each pair, the shorter intergenic region was omitted from motif discovery computations. This process removed up to nine regions for some experiments, but less than one on average.

To determine the sequences present on the microarrays, Applicants computed the expected products of the PCR used to construct the arrays. Research Genetics primer sequences were obtained from http://www.resgen.com/products/YeIRP.php3 and the March 2002 revision of the yeast genome was obtained from SGD (Dwight, S. S. et al. *Nucleic Acids Res* 30, 69-72 (2002)). Probes that were predicted to amplify more than two different genomic sequences were omitted from the calculations. Twenty five probe sequences neighboring repetitive, non-transcribed features (e.g. telomeric repeats, X elements and Y' elements) were also omitted.

PSSM Representation

Motifs from all programs were converted to a standard position-specific scoring matrix (PSSM) for subsequent analysis. AlignACE and MDscan produce alignments of binding sites, and these were first converted into matrices representing the frequency of each base (A, C, G, T) at each position of the alignments. The method of Kellis et al. represents motifs as text strings containing ambiguity codes, which were also converted to matrices of frequencies. (For example, if a motif contained the letter "S" at a particular position, a value of 0.5 would be assigned to both "C" and "G.") The matrices of base frequencies were converted to probabilities and then were adjusted with 0.001 pseudo-counts in proportion to the $0^{th}$-order background probabilities ($3.1 \times 10^4$ pseudocounts for A and T, $1.9 \times 10^{-4}$ pseudocounts for G and C). Log-likelihood scores were computed by dividing the estimated probabilities by the background probability for each letter and computing the base-2 logarithm. CONVERGE and MEME both provide probability matrices, which were used directly.

Step 2: Motif Scoring and Significance Testing

Applicants tested the significance of each motif by comparing how often it was found in the bound and unbound probes. To encapsulate different approaches to measuring motif over-representation, Applicants employed three different metrics: Enrichment, ROC AUC, and for motifs discovered by the method described in Kellis et al., the "CC4" score. The enrichment score is a direct measure of the occurrence of a motif among bound probes compared to all possible gene targets, but does not distinguish between the number of motifs occurrences within each intergenic region. The ROC AUC metric is more sensitive to cases in which the number of motif occurrences is a distinguishing factor. Finally, the CC4 metric provides a way to account for the importance of the conservation of the motif among bound probes. These scores were compared to significance thresholds obtained from calculations on randomized selections of intergenic regions as described below in "Significance Thresholds"

Enrichment Score

To obtain the enrichment score, the hypergeometric distribution was used to compare the frequency of the motif in the bound probes to that which would be expected if the intergenic regions were selected at random from the genome. A sequence was considered to contain a motif if it contained at least one or more sites scoring at least 70% of the maximum possible score of the matrix. A P-value for the enrichment was computed according to the formula:

$$p = \sum_{i=b}^{\min(B,g)} \frac{\binom{B}{i}\binom{G-B}{g-i}}{\binom{G}{g}} \quad (5)$$

where B is the number of bound intergenic regions and G is the total number of intergenic regions represented on the microarray (or the genome). The quantities b and g represent the number of intergenic regions of B and G matching the motif. The quantity $-\log_{10}(p)$ is referred to as the enrichment score.

ROC AUC (Receiver Operating Characteristic Area Under Curve)

The ROC AUC refers to the area under a receiver operating characteristic curve which is assembled by ranking the sets of bound and unbound probes according to the number of motif matches they contain, and plotting the fractional rankings against each other. Applicants used the method and code described by Clarke and Granek (Clarke, N. D. & Granek, J. A. Rank order metrics for quantifying the association of sequence features with gene regulation. *Bioinformatics* 19, 212-8 (2003)).

Conservation CC4

Motifs discovered using the method of Kellis et al. (Kellis, M., Patterson, N., Endrizzi, M., Birren, B. & Lander, E. S. Sequencing and comparison of yeast species to identify genes and regulatory elements. *Nature* 423, 241-54 (2003)) were judged according to the CC4 metric, in which the occurrence of a conserved motif among the bound probes is compared to the expected ratio observed among all 3-gap-3 motifs in among the same set of bound probes. The binomial probability of the observed ratio was computed, and is reported in terms of the equivalent z-score.

Significance Thresholds

Applicants observed that motif discovery programs produce motifs with high over-representation metrics (such as "Enrichment" and "ROC AUC") even when applied to random selections of intergenic regions. To identify the true motifs, Applicants converted the scores from each metric into the empirical probability that a motif with a similar score could be found by the same program in randomly selected sequences. Applicants accepted only those motifs with a P-value≦0.001. Applicants selected this stringent threshold to minimize false positives, and because Applicants observed empirically that it identified the correct motifs for many regulators with known specificity. To estimate these thresholds, Applicants ran each program 50 times on randomly selected sequences on sets of 10, 20, 30, 40, 50, 60, 70, 80, 100, 120, 140, and 160 probes.

The observed scores from these random runs were parameterized by a normal distribution. The critical values equivalent to a P-value of 0.001 are provided in Table 8 for each program and each metric. If the empirical distribution was not normal (by the Shapiro-Wilk test), the corresponding metric was not used to evaluate motifs generated by the relevant program for regulators with a similar number of bound probes.

For a particular experiment, Applicants employed the threshold derived from the randomization set that had the size closest to the number of bound probe sequences. For example, suppose a motif found by performing ten runs of AlignACE on 32 intergenic sequences had an enrichment score of 25. The relevant score distribution has been obtained by performing ten runs of AlignACE on each of 50 randomly selected sets of 30 intergenic sequences. The resulting distribution of enrichment scores has a mean of 14.1 and standard deviation of 2.1, and the enrichment that corresponds to significance of P≦0.001 is thus 20.43. Since the score of the candidate motif is higher, it is considered significant.

Step 3: Motif Clustering and Averaging

K-Medoids Clustering

The set of significant motifs for each experiment was then clustered via k-medoids clustering (Hastie et al. *The elements of statistical Learning; Data mining, inference and prediction* (Springer-Verlag, New York, 2001)) using the distance metric described below. The k-medoids algorithm was performed 500 times to find a clustering with a minimal sum of intercluster distances. To find the optimal number of clusters, this process was first performed with 10 clusters, and then repeated with incrementally fewer clusters until all average distances between members of a cluster and medoids of other clusters were sufficiently large (greater or equal to 0.18).

Inter-Motif Distance

Applicants constructed a distance metric to aid in the comparison of motifs. The distance D between two aligned motifs "a" and "b" is defined as, $$D(a,b) = \frac{1}{w}\sum_{i=1}^{w} \frac{1}{\sqrt{2}} \sum_{L \in \{ACGT\}} (a_{i,L} - b_{i,L})^2 \quad (1)$$

where w is the motif width, and $a_{i,L}$ and $b_{i,L}$ are the estimated probabilities of observing base L at position i of motifs a and b, respectively. The normalizations by w and $\sqrt{2}$ facilitate the interpretation as a fractional distance. For example, a distance of 0.20 indicates that the two motifs differ by about 20%.

In practice, the optimal alignment of motifs is not known. Applicants therefore use the minimum distance between motifs among all alignments in which the motifs overlap by at least seven bases, or when the motifs are shorter, by 2 bases fewer than the shortest motif length. Alignments to the reverse complements of the motifs are included.

Motif Averaging

A single motif representing each cluster was computed by averaging the probabilities at each matrix position of the aligned motifs comprising the cluster. Low-information positions on the flanks of the averaged motifs were removed.

Step 4: Conservation Testing for Averaged Motifs

Applicants tested the conservation of averaged motifs, and focused subsequent analysis on the motifs that met two conservation criteria: First, Applicants required that the frequency of conserved instances of the motif compared to all instances of the motif be at least as high within bound intergenic regions as among all intergenic regions. Second, Applicants required that discovered motifs have at least three conserved instances that are bound.

Applicants considered a sequence a match to a motif if it had a score of at least 60% of the motif maximum. Applicants defined a "conserved instance" to mean that the aligned sequence of at least two other sensu stricto species also matched the motif. In cases where fewer than two aligned sequences were available, a site was treated as "not conserved."

Step 5: Assignment a Single Motif to Each Regulator

Often, the motif discovery process produced several significant, distinct averaged motifs (3 on average.). These motifs could represent the desired binding specificity of the protein, or they might arise from the specificity of binding partners or have other biological significance. To identify those motifs representing the binding specificity of the profiled transcription factor, Applicants compared the specificities to binding data in the Transfac (Matys, V. et al. TRANSFAC: transcriptional regulation, from patterns to profiles. *Nucleic Acids Res* 31, 374-8 (2003)), YPD (Csank, C. et al. Three yeast proteome databases: YPD, PombePD, and CalPD (MycoPathPD). *Methods Enzymol* 350, 347-73 (2002)), and SCPD (Zhu, J. & Zhang, M. Q. SCPD: a promoter database of the yeast *Saccharomyces cerevisiae*. *Bioinformatics* 15, 607-11 (1999)) databases, when available, using the same inter-motif distance metric used for clustering (see above.) There were 21 regulators for which no such data were available. In these cases Applicants chose the motif with the best enrichment score.

Specificity data from these databases is sometimes available in the forms of raw sequences, ambiguity codes, and matrices. For regulators without matrices, Applicants assembled a single consensus sequence to represent the body of experimentally determined specificity information and converted it to a PSSM as described above. Since there is no way to independently assess the quality of the motifs assembled from the databases, Applicants used a permissive threshold to detect similarity between the discovered motifs and the database motifs. Motifs scoring below 0.24 were accepted as matches, while motifs with scores less than 0.35 were examined manually. The scores for the motifs that were used in the Regulatory Code Map are provided in Table 2.

Motifs Derived from the Literature

Applicants used a motif derived from the databases for the remaining regulators for which either: (1) Too few intergenic regions (<10) were bound for effective motif discovery, (2) discovered motifs similar to the literature were eliminated by the conservation in Step 4, or (3) none of the discovered motifs matched the literature in Step 5. These motifs were only included if they had at least one conserved instance that was bound. The resulting compendium of 102 motifs (Table 3) was used in all subsequent analysis.

Regulatory Code Map

Binding motifs for 102 regulators (Table 3) were fused with location analysis data and conservation data to produce a map of active binding sites in intergenic regions. The entire map is available at http://web.wi.mit.edu/fraenkel/regulatory_map/. The map was constructed by finding all conserved occurrences of each motif within intergenic regions bound by the corresponding factor.

Applicants used a binding P-value threshold of $P \leq 0.001$ and the definition of conservation as described in the "Conservation Test" section above. Variants of the map constructed with different binding and conservation thresholds are also available online.

Distributions of distances from the start codon (ATG) of open reading frames to binding sites in the adjacent upstream region were derived from the above data. These were compared to a distribution calculated on ten thousand "randomized" genomes in which the binding sites in each intergenic region were redistributed randomly and independently between the adjacent genes. The region from −100 to −500 (grey area in FIG. 2C) contains many more binding sites than expected.

Promoter Classification

Promoters were classified based on the aggregate binding data from all experiments. A promoter was defined as having multiple regulator architecture if more than one regulator bound in the aggregate data, regardless of the number of regulators that bound in any particular condition. Similarly, a promoter was assigned to the single regulator architecture if it was bound by exactly one regulator in the aggregate data.

Regulators that had a tendency to use the repetitive motif architecture were identified by chi-square analysis. For each regulator, Applicants calculated the number of promoters containing a single site and the number containing multiple sites. These values were then compared to the expected values based on the average for all factors.

Co-occurring regulatory motifs were determined based on P values representing the probability, based on the hypergeometric distribution, of finding the observed number of intergenic regions (or more) bound by both regulators under the null hypothesis that binding for the two regulators is independent.

Regulator Behavior Classification

The binding of each regulator was compared in pair-wise fashion for every environmental condition in which that regulator was studied. Only regions bound at $P \leq 0.001$ and containing conserved matches to the corresponding motif were included in this analysis. Some regulators fall into multiple categories depending on exactly which conditions are compared. For the "condition invariant" category the ratio of the overlap of bound probes for a regulator was greater than 0.66, and the ratio of the number of bound probes was between 0.66 and 1.5. For the "condition enabled" category the regulator bound to no probes in one environment. For the "condition expanded" category the ratio of the overlap of bound probes for a regulator was greater than 0.66, and the ratio of the number of bound probes was less than 0.66 or greater than 1.5. For the "condition altered" category the regulator bound at least one probe in both environments and the ratio of the overlap of bound probes was less than 0.66.

Experimental Confirmation of Predicted Specificity

Applicants compared the discovered motifs to those in the literature using an automated method, and selected the regulator for which the discrepancy was the greatest, Cin5 (Table 2). The discovered motif, TTAcrTAA, contains a one base insertion compared to the previously reported site (Fernandes, L., Rodrigues-Pousada, C. & Struhl, K. Yap, a novel family of eight bZIP proteins in *Saccharomyces cerevisiae* with distinct biological functions. *Mol Cell Biol* 17, 6982-93 (1997)), TTACTAA. The previously known site is poorly enriched in the probes bound by Cin5 ($P \leq 0.02$), while the discovered motif is very strongly enriched ($P \leq 10^{-38.4}$).

Figure 7:
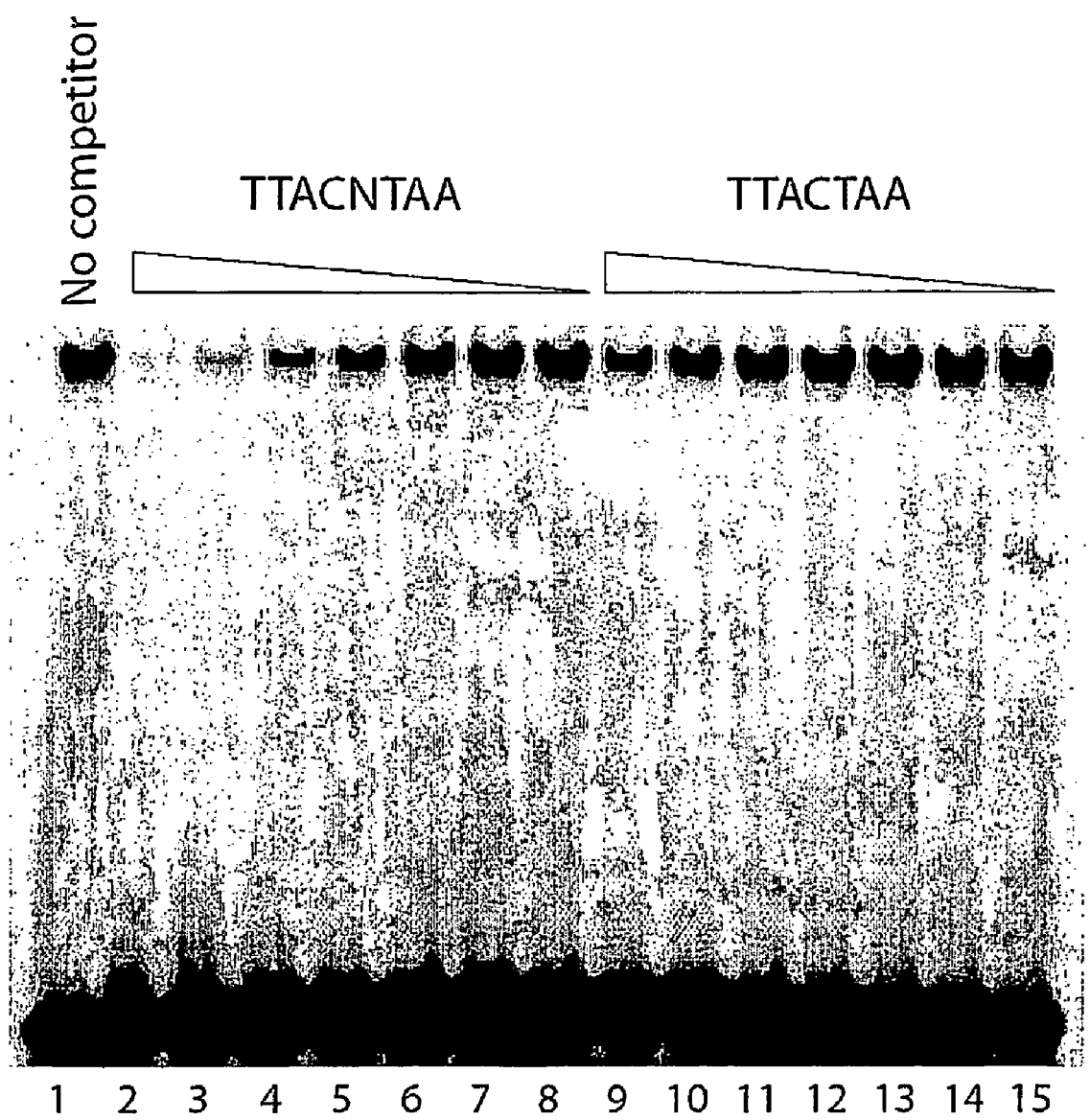
FIG. 7 shows a comparison of Cin5 binding to two sequences. Recombinant Cin5 was purified from bacteria and incubated with a Cy5-labeled oligonucleotide containing the sequence (gcgacaTTACCTAAgggc) and challenged with one of two unlabeled competitors: the same sequence (lanes 2-8) or the previously published binding site (gcgacaTTAC-TAAagggc; lanes 9-15). The concentration of each competitor was varied in 3-fold steps. The probe based on our discovered motif was approximately 27-fold better in competing away the shifted band compared to the probe based on the previously published specificity. Similar results were obtained for a probe containing a core sequence of TTACG-TAA.

Applicants used a gel-shift assay to test whether the specificity for Cin5 that Applicants inferred from our in viva data also represented the in vitro properties for this regulator (FIG. 7). The DNA-binding domain of Cin5 was cloned into a derivative of the pET-32 vector (Novagen) fused to thioredoxin and a poly-histidine peptide, expressed in *E. coli*, and purified by affinity chromatography. Protein was incubated with a Cy5-labeled oligonucleotide containing the sequence gcgacaTTACCTAAgggc and challenged with unlabeled competitor containing either the same sequence or the previously published binding site (gcgacaTTACTAAggggc) (Fernandes et al. *Mol Cell Biol* 17, 6982-93 (1997)). The reactions were analyzed on 10% acrylamide gels run in 0.5× TBE. Similar results were obtained for a probe containing the core sequence of TTACGTAA.

Regulatory Code

Potential binding sites were included in the map of the regulatory code if they satisfied two criteria. First, a locus had to match the specificity model for a regulator in the *Saccharomyces cerevisiae* genome and at least two other sensu stricto cerevisiae genomes with a score ≥60% of the maximum possible. Second, the locus had to lie in an intergenic region that also contained a probe bound by the corresponding regulator in any condition ($P \leq 0.001$). All analyses of promoter architecture and environment-specific binding were based on this map, and is described further below. More detailed information concerning all the methods described in the example below can be found in at http://web.wi.mit.edu/young/regulatory_code.

Example 1

Identification of Biologically-Active DNA-Binding Sites

Figure 5:
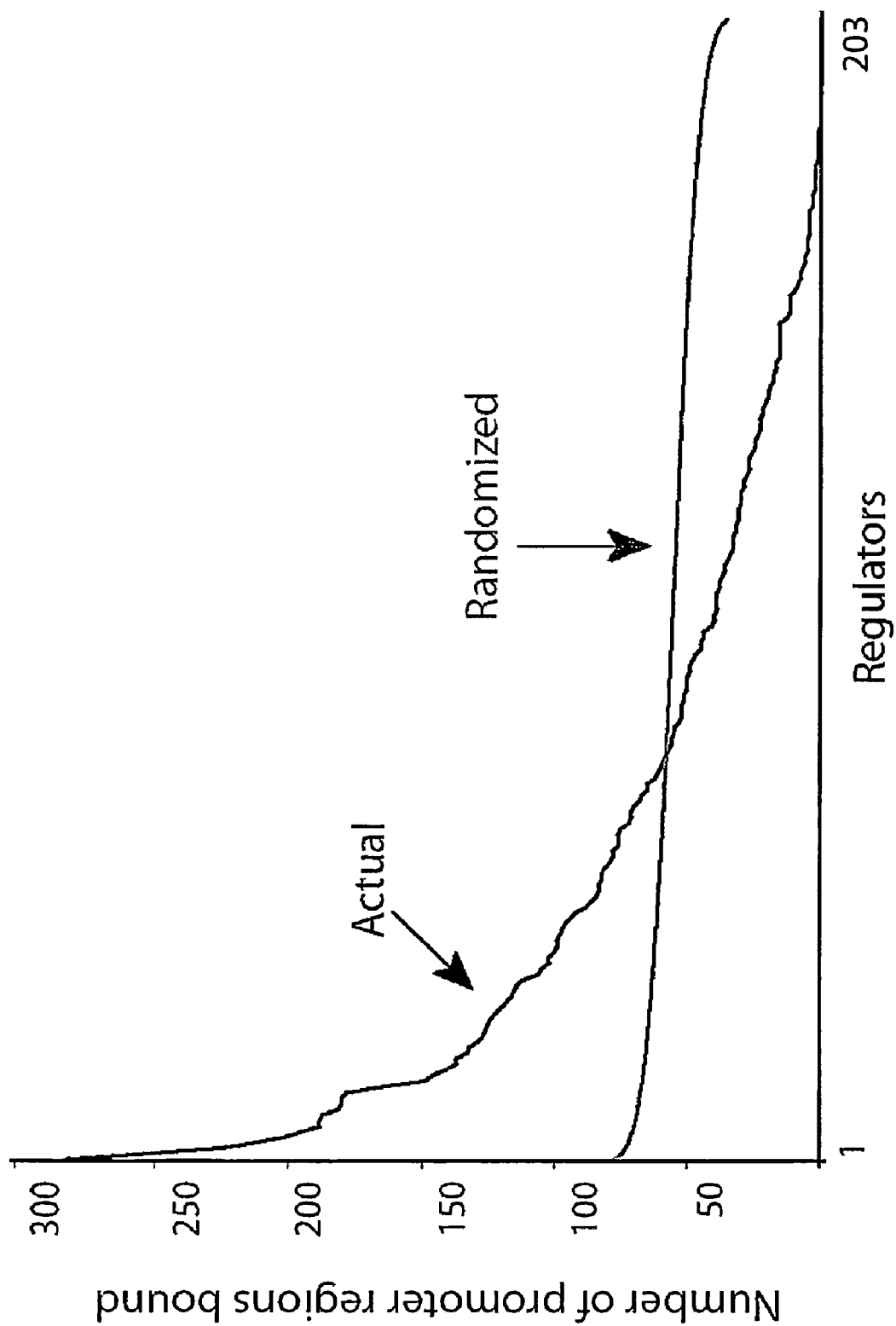
FIG. 5 shows the distribution of the number of promoter regions bound per regulator as a line labelled "actual". For regulators profiled under multiple conditions, the union of promoter regions bound under all conditions is reported. An average of randomized distributions for the same set of P values randomly assigned among regulators and promoter regions is shown as a line labeled "randomized".

Applicants used genome-wide location analysis (Iyer et al. *Nature* 409, 533-8. (2001), Ren et al. *Science* 290, 2306-9. (2000), Lee et al. *Science* 298, 799-804. (2002), Lieb et al. *Nat Genet* 28, 327-34 (2001)) to determine the genomic occupancy of 203 DNA-binding transcriptional regulators in rich media conditions and, for 84 of these regulators, in at least one of twelve other environmental conditions (Table 1, FIG. 5, http://web.wi.mit.edu/young/regulatory_code). These 203 proteins are likely to include nearly all of the DNA-binding transcriptional regulators encoded in the yeast genome. Regulators were selected for profiling in an additional environment if they were essential for growth in that environment or if there was other evidence implicating them in regulation of gene expression in that environment. The genome-wide location data identified 11,000 unique interactions between regulators and promoter regions at high confidence ($P \leq 0.001$).

To identify the cis-regulatory sequences that likely serve as recognition sites for transcriptional regulators, Applicants merged information from genome-wide location data, phylogenetically conserved sequences, and prior knowledge (FIG. 1A). Applicants used six motif discovery methods 11-13 to discover 68,279 DNA sequence motifs for the 147 regulators that bound more than ten probes (see experimental procedures; FIG. 6). From these motifs Applicants derived the most likely specificity for each regulator through clustering and stringent statistical tests. This motif discovery process identified highly significant ($P \leq 0.001$) motifs for each of 116 regulators. Applicants determined a single high-confidence motif for 65 of these regulators using additional criteria including the requirement for conservation across three of four related yeast species. Examples of novel and "re-discovered" motifs are depicted in FIG. 1B, and comparisons of the discovered motifs to those described previously are shown in Table 2. The discovered motifs provide significantly more information than was previously available; for 21 of the regulators there was no prior specificity information in the literature, and detailed probability matrices had previously been determined for only 17 regulators for which Applicants report motifs (Knuppel et al. *J Comput Biol* 1, 191-8 (1994)). In the case of Cin5, which showed the largest difference between the computationally derived motif (TTACRTAA) and the previously reported site (TTACTAA; Table 2), Applicants found that the motif that Applicants report is also the preferred in vitro target (FIG. 7). Applicants supplemented the discovered motifs with additional motifs from the literature that also passed conservation tests, and Applicants used this compendium of sequence motifs for 102 regulators (Table 3) in all subsequent analysis.

Example 2

Constructions of Transcriptional Regulatory Code

Figure 2A:
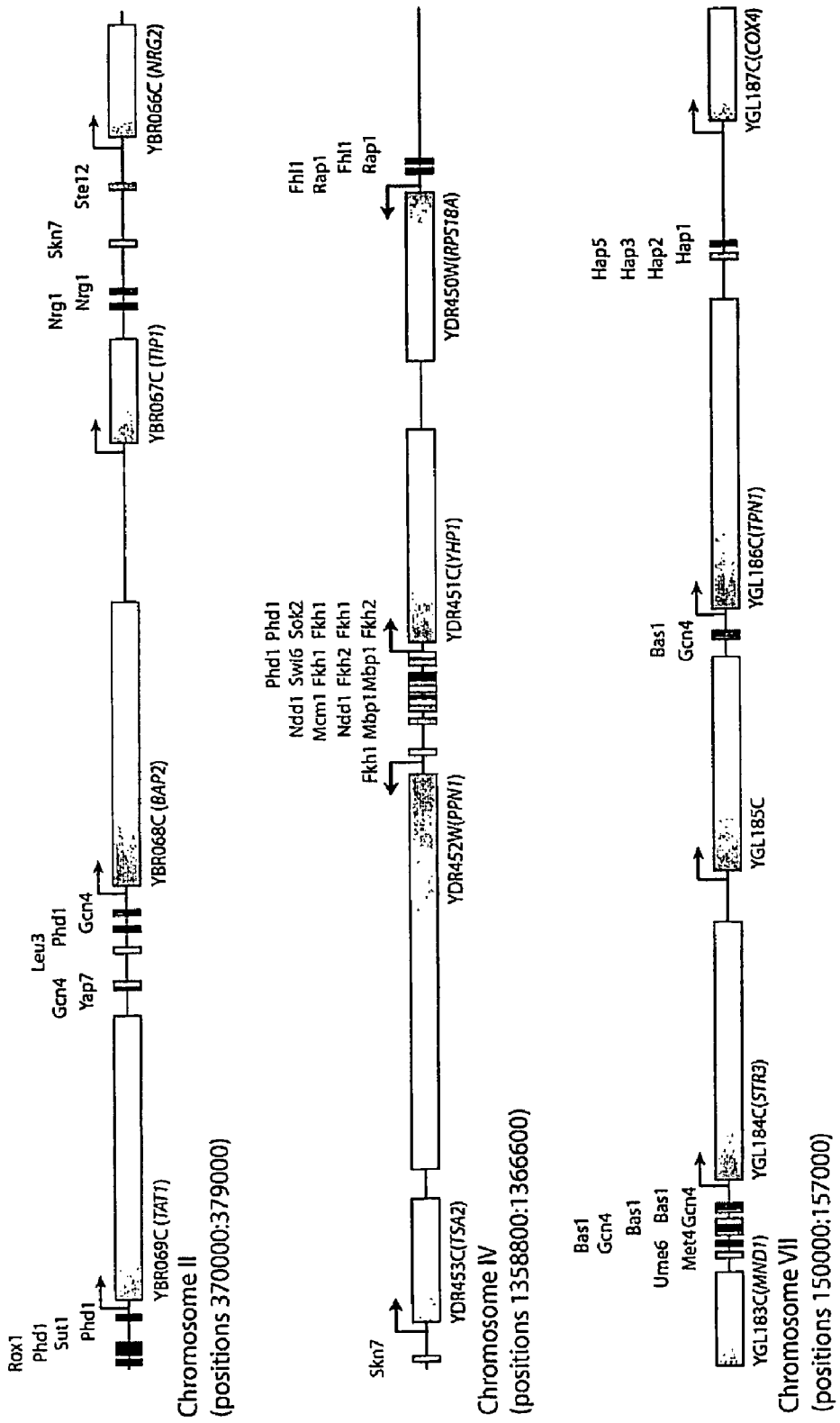
FIGS. 2A-2C show the drafting of the yeast transcriptional regulatory map.

Applicants constructed an initial version of the transcriptional regulatory code by mapping on the yeast genome sequence the motifs that are bound by regulators at high confidence ($P \leq 0.001$) and that are conserved among sensu stricto *Saccharomyces* species (FIG. 2; http://web.wi.mit.edu/fraenkel/regulatory_map). This map includes 3,353 interactions within 1,296 promoter regions. Maps of regulatory sites encompassing larger numbers of promoters, constructed with lower confidence information, can also be viewed on the authors' website. Because the information used to construct the map includes binding data from multiple growth environments, the map describes transcriptional regulatory potential within the genome. During growth in any one environment, only subsets of the binding sites identified in the map are occupied by transcriptional regulators, as Applicants describe in more detail below.

Where the functions of specific transcriptional regulators were established previously, the functions of the genes they bind in the regulatory map are highly consistent with this prior information. For example, the amino acid biosynthetic regulators Gcn4 and Leu3 bind to sites in the promoter of BAP2 (chromosome II), which encodes an amino acid transporter (FIG. 2A). Six well-studied cell cycle transcriptional regulators bind to the promoter for YHP1 (chromosome IV), which has been implicated in regulation of the G1 phase of the cell cycle. The regulator of respiration Hap5, binds upstream of COX4 (chromosome VII), which encodes a component of the respiratory electron transport chain. Where regulators with established functions bind to genes of unknown function, these target genes are newly implicated in such functional processes.

Figure 2B:
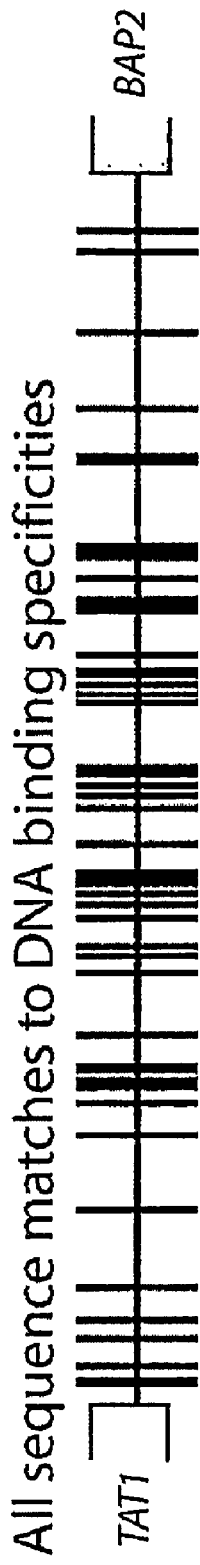
Figure 2B:
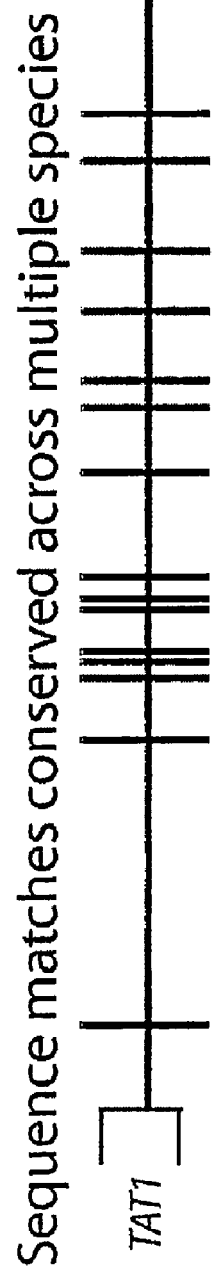
Figure 2B:
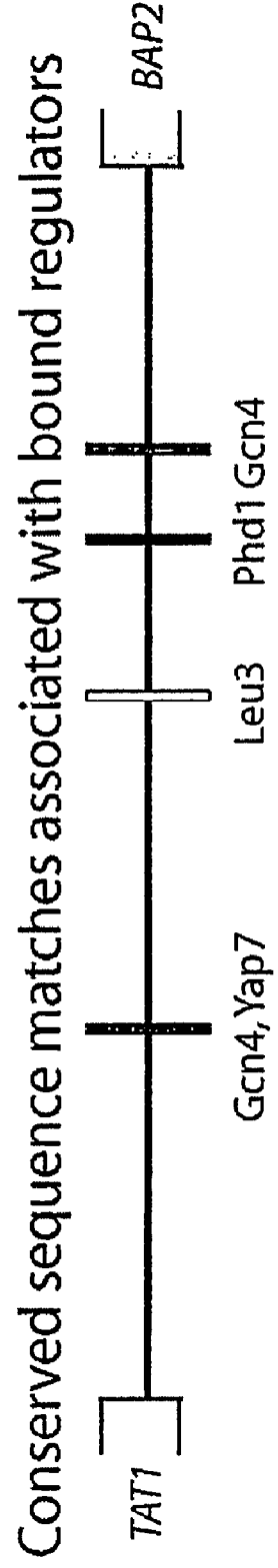

The utility of combining regulator binding data and sequence conservation data is illustrated in FIG. 2B. All sequences matching the regulator DNA binding specificities described in this study (Table 2) that occur within the 884 base-pair intergenic region upstream of the gene BAP2 are shown in the upper panel. The subset of these sequences that have been conserved in multiple yeast species, and are thus likely candidates for regulator interactions, are shown in the middle panel. The presence of these conserved regulatory sites indicates the potential for regulation via this sequence, but does not indicate whether the site is actually bound by a regulator under some growth condition. The incorporation of binding information (bottom panel) identifies those conserved sequences that are utilized by regulators in cells grown under the conditions examined.

Figure 2C:
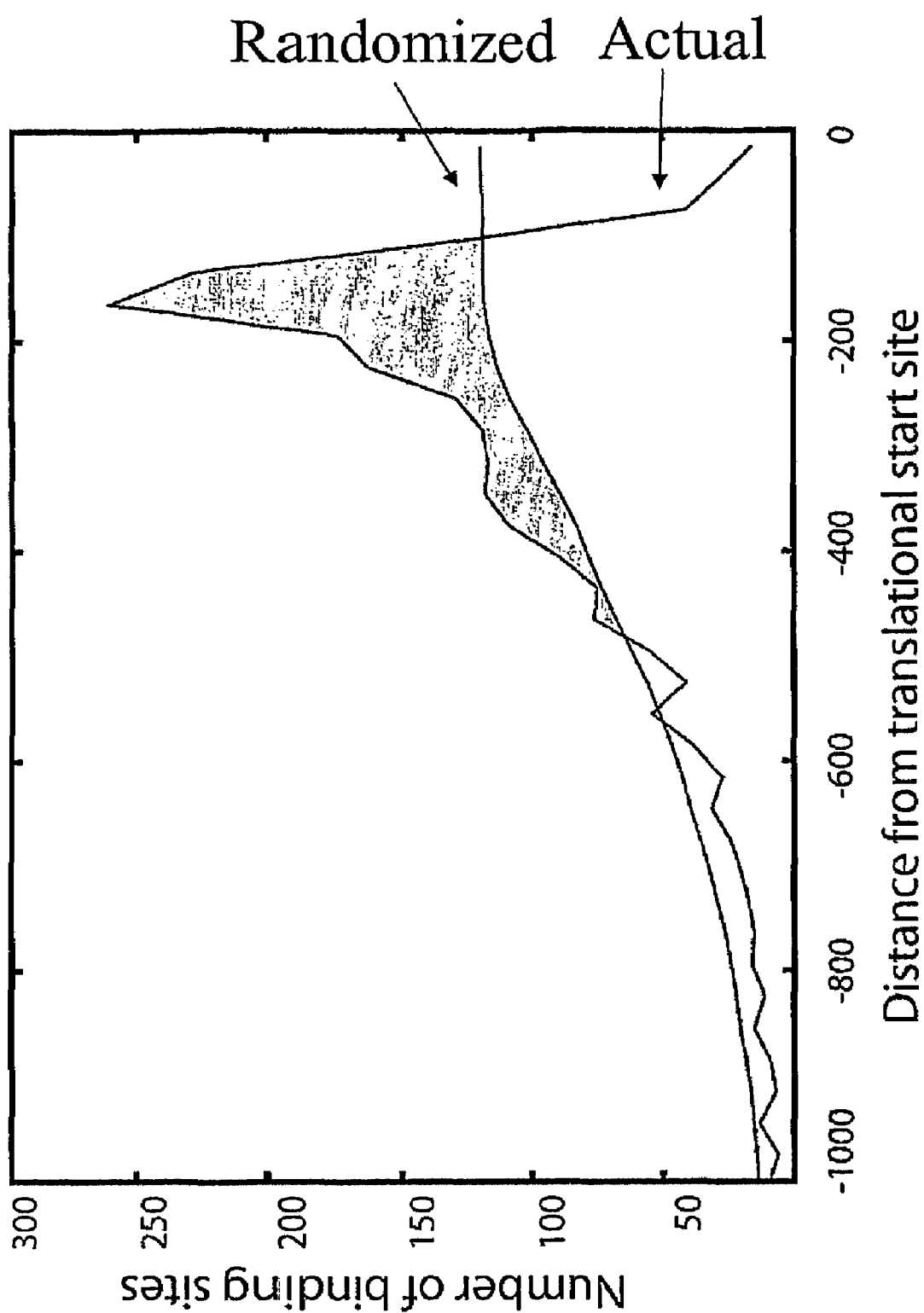

The distribution of binding sites for transcriptional regulators reveals there are constraints on the organization of these sites in yeast promoters (FIG. 2C). Binding sites are not uniformly distributed over the promoter regions, but rather show a sharply peaked distribution. Very few sites are located in the region 100 base pairs (bp) upstream of protein coding sequences. This region typically includes the transcription start site and is bound by the transcription initiation apparatus. The vast majority (74%) of the transcriptional regulator binding sites lie between 100 and 500 bp upstream of the protein coding sequence, far more than would be expected at random (53%). Regions further than 500 bp contain fewer binding sites than would be expected at random. It appears that yeast transcriptional regulators function at short distances along the linear DNA, a property that reduces the potential for inappropriate activation of nearby genes.

Figure 3:
FIG. 3 shows yeast promoter architectures. Single regulator architecture: promoter regions that contain one or more copies of the binding site sequence for a single regulator. Repetitive motif architecture: promoter regions that contain multiple copies of a binding site sequence of a regulator. Multiple regulator architecture: promoter regions that contain one or more copies of the binding site sequences for more than one regulator. Co-occurring regulator architecture: promoters that contain binding site sequences for recurrent pairs of regulators. For the purposes of illustration, not all sites are shown and scale is approximate. Additional information can be found in Tables 4-6.
Figure 3:
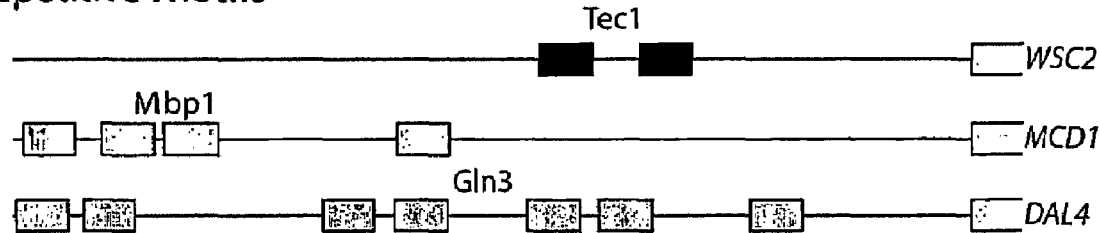
Figure 3:
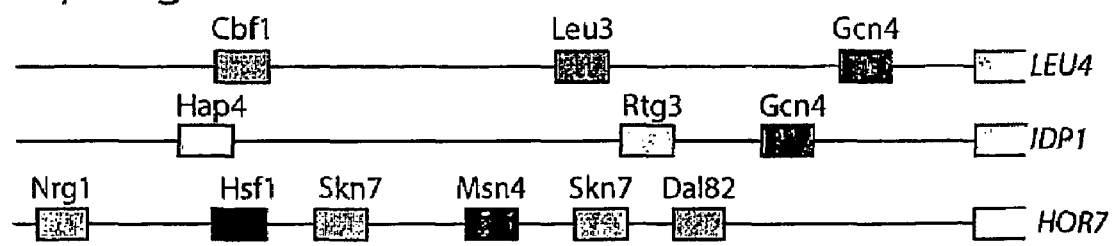
Figure 3:
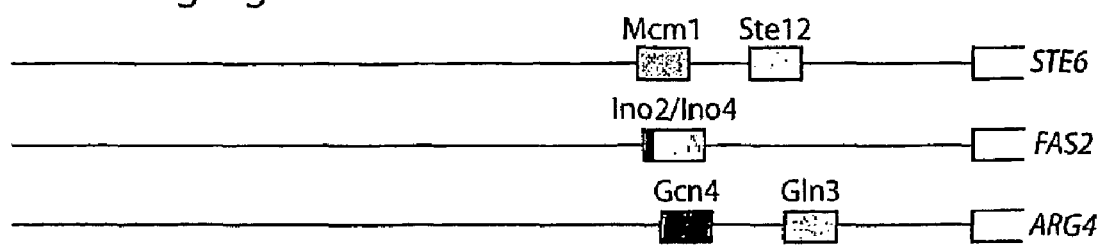

Applicants note that specific arrangements of DNA-binding site sequences occur within promoters, and suggest that these promoter architectures provide clues to regulatory mechanisms (FIG. 3). For example, the presence of a DNA-binding site for a single regulator is the simplest promoter architecture and, as might be expected, Applicants found that sets of genes with this feature are often involved in a common biological function (Table 4). A second type of promoter architecture consists of repeats of a particular binding site sequence. Repeated binding sites have been shown to be necessary for stable binding by the regulator Dal80 (Cunningham et al. *J Bacteriol* 175, 5851-61 (1993)). This repetitive promoter architecture can also allow for a graded transcriptional response, as has been observed for the HIS4 gene (Donahue et al. *Cell* 32, 89-98 (1983)). A number of regulators, including Dig1, Mbp1, and Swi6 show a statistically significant preference for repetitive motifs (Table 5). A third class of promoter contains binding sites for multiple different regulators. This promoter arrangement implies that the gene may be subject to combinatorial regulation, and Applicants expect that in many cases the various regulators can be used to execute differential responses to varied growth conditions. Indeed, Applicants note that many of the genes in this category encode products that are required for multiple metabolic pathways and are regulated in an environment-specific fashion. In the fourth type of promoter architecture Applicants discuss here, binding sites for specific pairs of regulators occur more frequently within the same promoter regions than would be expected by chance (Table 6). This "co-occurring" motif architecture implies that the two regulators physically interact or have shared functions at multiple genes.

Example 3

Figure 4:
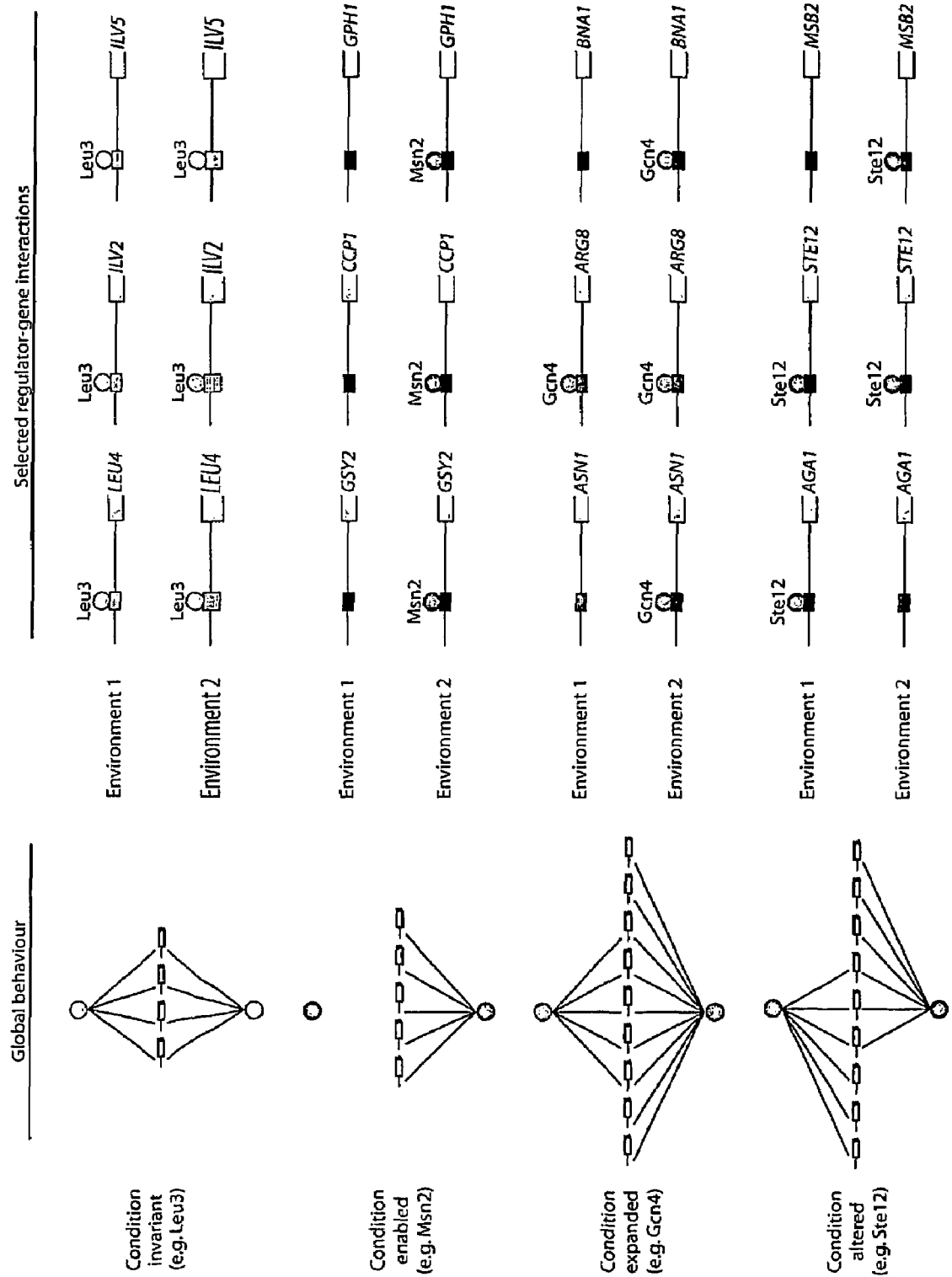
FIG. 4 shows environment-specific utilization of the transcriptional regulatory code. Four patterns of genome-wide binding behavior are depicted in a graphic representation on the left, where transcriptional regulators are represented by circles and are placed above and below a set of target genes/promoters. The lines between the regulators and the target genes/promoters represent binding events. Specific examples of the environment-dependent behaviors are depicted on the right. Circles represent regulators and boxes represent their DNA binding sequences within specific promoter regions. Applicants note that regulators may exhibit different behaviors when different pairs of conditions are compared.
Figure 8:
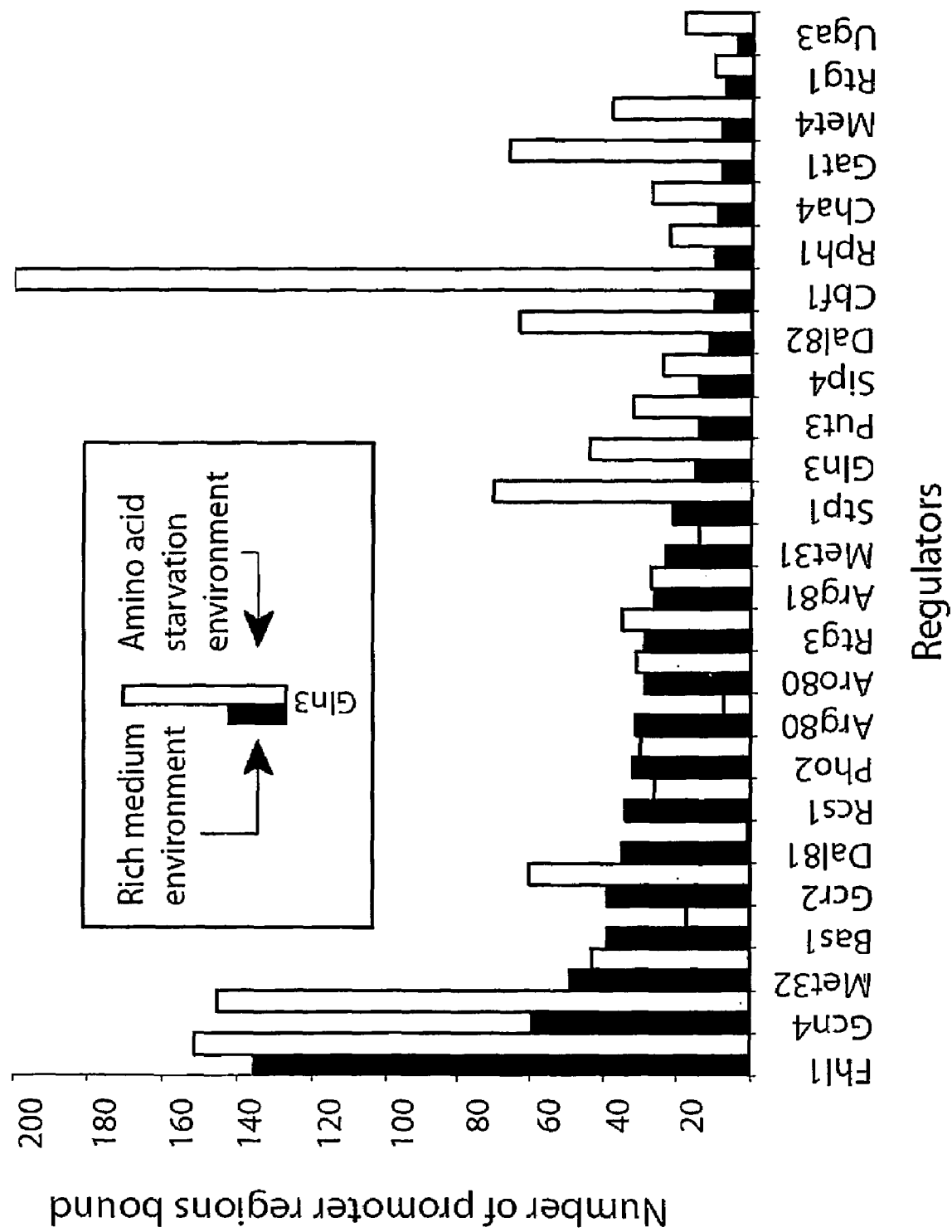
FIG. 8 shows a pairwise comparison of the number of promoter regions bound under two different conditions for 25 regulators (based solely on genome-wide location data with P<0.001). Dark bars represent the number of promoter regions bound under growth in rich medium; light bars represent the number of promoter regions bound under growth in amino acid starvation medium.

Identification of Conditions which Alter the Distribution of Biologically-Active DNA-Binding Sites By conducting genome-wide binding experiments for some regulators under multiple cell growth conditions, Applicants learned that regulator binding to a subset of the regulatory sequences is highly dependent on the environmental conditions of the cell (FIG. 8). Applicants observed four common patterns of regulator binding behavior (FIG. 4, Table 7). Prior information about the regulatory mechanisms employed by well-studied regulators in each of the four groups suggests hypotheses to account for the environment-dependent binding behavior of the other regulators.

"Condition invariant" regulators bind essentially the same set of promoters (within the limitations of noise) in two different growth environments (FIG. 4). Leu3, which is known to regulate genes involved in amino acid biosynthesis, is among the best studied of the regulators in this group. Binding of Leu3 in vivo has been shown to be necessary, but not sufficient for activation of Leu3-regulated genes (Kirkpatrick et al. *Mol Cell Biol* 15, 4021-30 (1995)). Rather, regulatory control of these genes requires association of a leucine metabolic precursor with Leu3 to convert it from a negative to positive regulator. Applicants note that other zinc cluster type regulators that show "condition invariant" behavior are known to be regulated in a similar manner (Axelrod et al. *Mol Cell Biol* 11, 564-7 (1991), Ma et al. *Cell* 50, 137-42 (1987)). Thus, it is reasonable to propose that the activation or repression functions of some of the other regulators in this class will be independent of DNA binding.

"Condition enabled" regulators do not bind the genome detectably under one condition, but bind a substantial number of promoters with a change in environment. Msn2 is among the best-studied regulators in this class, and the mechanisms involved in Msn2-dependent transcription provide clues to how the other regulators in that class may operate. Msn2 is known to be excluded from the nucleus when cells grow in the absence of stresses, but accumulates rapidly in the nucleus when cells are subjected to stress (Beck et al. *Nature* 402, 689-92 (1999), Chi et al. *Genes Dev* 15, 1078-92. (2001)). This condition-enabled behavior was also observed for the thiamine biosynthetic regulator Thi2, the nitrogen regulator Gat 1, and the developmental regulator Rim101. Applicants suggest that many of these transcriptional regulators are regulated by nuclear exclusion or by another mechanism that would cause this extreme version of condition-specific binding.

Figure 9:
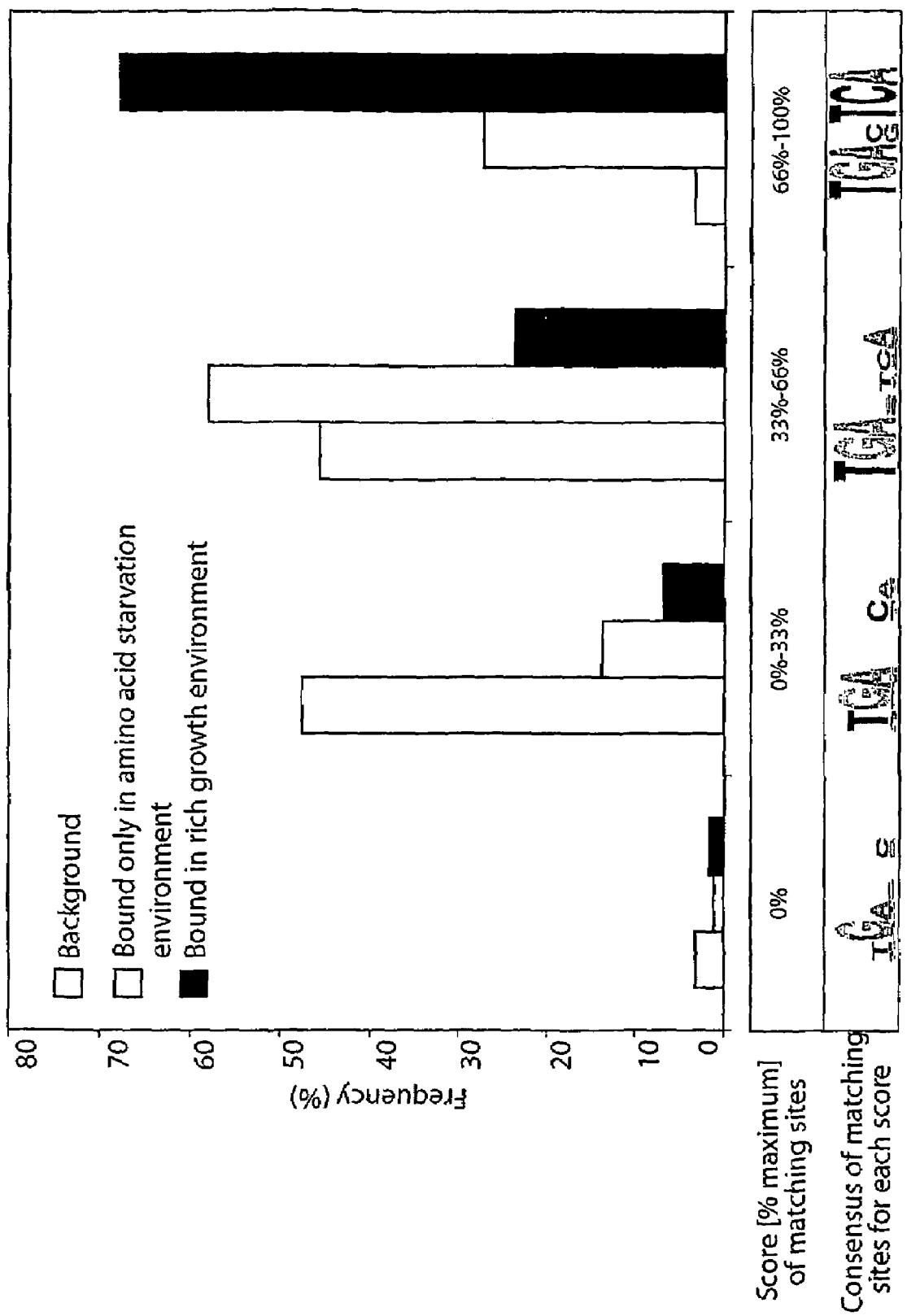
FIG. 9 shows the quality of Gcn4 binding sites among intergenic regions bound under different conditions. Each intergenic region was scored based on the quality of the best matching subsequence to the Gcn4 binding specificity (TGASTCA). In rich media conditions 68% of the intergenic regions contain high-quality matches to the Gcn4 specificity. Under starvation conditions the levels of Gcn4 protein rise, and the set of bound intergenic regions expands. Of the newly bound regions, only 27% contain high-quality matches. By contrast, only 3% of all intergenic regions contain matches of this quality.

"Condition expanded" regulators bind to a core set of target promoters under one condition, but bind an expanded set of promoters under another condition. Gcn4 is the best-studied of the regulators that fall into this "expanded" class. The levels of Gcn4 are reported to increase 6-fold when yeast are introduced into media with limiting nutrients (Albrecht et al. *J Biol Chem* 273, 12696-702. (1998)), due largely to increased nuclear protein stability (Chi et al. *Genes Dev* 15, 1078-92. (2001), Kornitzer et al. *EMBO J* 13, 6021-30. (1994)), and under this condition Applicants find Gcn4 binds to an expanded set of genes. Interestingly, the probes bound when Gcn4 levels are low contain better matches to the known Gcn4 binding site than probes that are bound exclusively at higher protein concentrations, consistent with a simple model for specificity based on intrinsic protein affinity and protein concentration (FIG. 9). The expansion of binding sites by many of the regulators in this class may reflect increased levels of the regulator available for DNA binding.

"Condition altered" regulators exhibit altered preference for the set of promoters bound in two different conditions. Step 12 is the best studied of the regulators whose binding behavior falls into this "altered" class. Depending on the interactions with other regulators, the specificity of Step 12 can change and alter its cellular function (Zeitlinger, et al. *Cell* 113, 395-404 (2003). For example, under filamentous growth conditions, Step 12 interacts with Tec1, which has its own DNA-binding specificity (Baur et al. *Mol Cell Biol* 17, 4330-7 (1997)). This condition-altered behavior was also observed for the transcriptional regulators Aft2, Skn7, and Ume6. Applicants propose that the binding specificity of many of the transcriptional regulators may be altered through interactions with other regulators or through modifications (e.g., chemical) that are environment-dependent.

Substantial portions of eukaryotic genome sequence are believed to be regulatory (Kellis et al. *Nature* 423, 241-54 (2003), Cliften et al. *Science* 301, 71-6 (2003), Waterston et al. *Nature* 420, 520-62 (2002)), but the DNA sequences that actually contribute to regulation of genome expression have been ill-defined. By mapping the DNA sequences bound by specific regulators in various environments, Applicants identify the regulatory potential embedded in the genome and provide a framework for modeling the mechanisms that contribute to global gene expression. Applicants anticipate that the approaches used here to map regulatory sequences in yeast can also be used to map the sequences that control genome expression in higher eukaryotes.

TABLE 1

List of regulators and environmental conditions examined*

A1
Abf1
Abt1
Aca1
Ace2
Adr1[3,7]
Aft2[1,2]
Arg80[3]
Arg81[3]
Aro80[3]
Arr1[1]
Ash1[5]
Ask10
Azf1
Bas1[3]
Bye1
Cad1[1,3]
Cbf1[3]
Cha4[3]
Cin5[1,2]
Crz1
Cst6
Cup9
Dal80[4]
Dal81[3,4]
Dal82[3,4]
Dat1
Dig1[5,6]
Dot6
Ecm22
Eds1
Fap7
Fhl1[1,3,4]
Fkh1
Fkh2[1,2]
Fzf1
Gal3
Gal4[8,9]
Gal80
Gat1[3,4,7]
Gat3
Gcn4[3,4]
Gcr1
Gcr2[3]
Gln3[3,4]
Gts1
Gzf3[1,4]
Haa1
Hac1
Hal9
Hap1
Hap2[4]
Hap3

TABLE 1-continued

List of regulators and environmental conditions examined*

Hap4[2,3]
Hap5[3]
Hir1
Hir2
Hir3
Hms1
Hms2
Hog1
Hsf1[1,2,7]
Ifh1
Ime1[1]
Ime4[1]
Ino2
Ino4
Ixr1
Kre33
Kss1[5,6]
Leu3[3]
Mac1[1]
Mal13
Mal33[1,2]
Mbf1
Mbp1[1,2]
Mcm1[5,6]
Mds3
Met18
Met28[3]
Met31[3]
Met32[3]
Met4[3]
Mga1[1]
Mig1[8]
Mig2[1]
Mig3
Mot3[1,2,3]
Msn1
Msn2[1,2,4,7,10]
Msn4[1,2,4,10]
Mss11[5]
Mth1[8]
Ndd1
Ndt80
Nnf2
Nrg1[1,2]
Oaf1
Opi1
Pdc2
Pdr1[2]
Pdr3
Phd1[5]
Pho2[1,2,3,11]
Pho4[11]
Pip2
Ppr1
Put3[2,3]
Rap1[3]
Rco1
Rcs1[1,2,3]
Rdr1
Rds1[1]
Reb1[1,2]
Rfx1
Rgm1
Rgt1[8]
Rim101[1,2]
Rlm1[5]
Rlr1
Rme1
Rox1[1,2]
Rph1[1,2,3]
Rpi1
Rpn4[1,2]
Rtg1[3,4]
Rtg3[1,2,3,4]
Rts2
Sfl1
Sfp1[1,2,3]

TABLE 1-continued

List of regulators and environmental conditions examined*

Sig1[1]
Sip3
Sip4[3]
Skn7[1,2,7]
Sko1
Smk1
Smp1
Snf1
Snt2
Sok2[5]
Spt10
Spt2
Spt23
Srd1
Stb1
Stb2
Stb4
Stb5
Stb6
Ste12[5,6]
Stp1[3]
Stp2
Stp4
Sum1
Sut1
Sut2
Swi4
Swi5
Swi6
Tbs1
Tec1[5,6]
Thi2[12]
Tos8
Tye7
Uga3[3,4]
Ume6[1]
Upc2
Usv1
War1
Wtm1
Wtm2
Xbp1[2,7]
Yap1[1,2,7]
Yap3[1]
Yap5[1]
Yap6[1,2]
Yap7[1,2]
YBL054W
YBR239C
YBR267W
YDR026C
YDR049W
YDR266C
YDR520C
YER051W
YER130C
YER184C
YFL044C
YFL052W
YGR067C
Yhp1
YJL206C[1,2]
YKL222C
YKR064W
YLR278C
YML081W
YNR063W
Yox1
YPR022C
YPR196W
Yrr1
Zap1
Zms1

[1]Highly hyperoxic
[2]Mildly hyperoxic
[3]Amino acid starved
[4]Nutrient deprived
[5]Filamentation
[6]Mating
[7]Heat
[8]Galactose
[9]Raffinose
[10]Acidic
[11]Phosphate deprived
[12]Vitamin deprived

*All regulators were profiled in rich medium. A subset of these were profiled in at least one other environmental condition, as indicated. A complete description of the conditions can be found at the authors' website.

TABLE 2

Similarity of discovered specificities to literature

| Regulator | Distance[1] | Discovered | Literature |
|---|---|---|---|
| Abf1 | 0.143 | rTCAytnnnnAcg | rTCAyTnnnnACGw |
| Ace2 | 0.18 | tGCTGGT | GCTGGT |
| Aft2 | 0.15 | rCACCC | ATCTTCAAAAGTGCA-CCCATTTGCAGGTGC |
| Azf1 | 0.203 | YwTTkcKkTyyckgykky | TTTTTCTT |
| Bas1 | 0.045 | TGACTC | TGACTC |
| Cad1 | 0.089 | mTTAsTmAkC | TTACTAA |
| Cbf1 | 0.105 | tCACGTG | rTCACrTGA |
| Cin5 | 0.324 | TTAcrTAA | TTACTAA |
| Fkh1 | 0.123 | gtAAAcAA | GGTAAACAA |
| Fkh2 | 0.212 | GTAAACA | GGTAAACAA |
| Gal4 | 0.11 | CGGnnnnnnnnnnnnncCg | CGGnnnnnnnnnnnCCG |
| Gat1 | 0.004 | aGATAAG | GATAA |
| Gcn4 | 0.123 | TGAsTCa | ArTGACTCw |
| Gln3 | 0.148 | GATAAGa | GATAAGATAAG |
| Hap1 | 0.191 | GGnnaTAnCGs | CGGnnnTAnCGG |
| Hap4 | 0.146 | gnCcAAtcA | YCNNCCAATNANM |
| Hsf1 | 0.198 | TTCynnnnnnnTTC | TTCTAGAAnnTTCT |
| Ino2 | 0.236 | CAcaTGc | ATTTCACATC |
| Ino4 | 0.163 | CATGTGaa | CATGTGAAAT |
| Leu3 | 0.131 | cCGgtacCGG | yGCCGGTACCGGyk |
| Mbp1 | 0.073 | ACGCGt | ACGCGT |
| Mcm1 | 0.181 | CCnrAtnngg | wTTCCyAAwnnGGTAA |
| Msn2 | 0.308 | mAGGGGsgg | mAGGGG |
| Nrg1 | 0.042 | GGaCCCT | CCCT |
| Pdr1 | 0.301 | ccGCCgRAwr | CCGCGG |
| Pho4 | 0.096 | CACGTGs | cacgtkng |
| Rap1 | 0.181 | cayCCrtrCa | wrmACCCATACAyy |
| Rcs1 | 0.184 | ggGTGcant | AAmTGGGTGCAkT |
| Reb1 | 0.055 | TTACCCG | TTACCCGG |
| Rpn4 | 0.049 | GGTGGCAAA | GGTGGCAAA |
| Sip4 | 0.184 | CGGnynAATGGrr | yCGGAyrrAwGG |
| Skn7 | 0.228 | GnCnnGsCs | ATTTGGCyGGsCC |
| Stb5 | 0.058 | CGGnstTAta | CGG |
| Ste12 | 0.087 | tgAAAC | ATGAAAC |
| Sum1 | 0.221 | gyGwCAswaaw | AGyGwCACAAAAk |
| Sut1 | 0.295 | gcsGsgnnsG | CGCG |
| Swi4 | 0.122 | CgCsAAA | CnCGAAA |
| Swi6 | 0.214 | CGCgaaa | CnCGAAA |
| Tec1 | 0.064 | CATTCyy | CATTCy |
| Tye7 | 0.193 | tCACGTGa | CAnnTG |
| Ume6 | 0.16 | taGCCGCCsa | wGCCGCCGw |
| Yap1 | 0.124 | TTaGTmAGc | TTAsTmA |
| Yap7 | 0.15 | mTkAsTmA | TTACTAA |
| Zap1 | 0.085 | ACCCTmAAGGTyrT | AGCCTAAAGGT |

[1]Distance from known specificity was computed using the distance metric described in the experimental procedures.

TABLE 3

Regulator specificities

| Regulator | Discovered specificity[1] | Known specificity[1,2] | Programs[3] |
|---|---|---|---|
| Abf1 | rTCAytnnnnAcg | rTCAyTnnnnACGw | A, C, D, K, M, N |
| Ace2 | tGCTGGT | GCTGGT | K |
| Adr1 | | GGrGk | |
| Aft2 | rCACCC | . . . AAAGTGCACCCATT . . . | A, C, D, M, N |
| Arr1 | | TTACTAA | |
| Ash1 | | yTGACT | |
| Azf1 | YwTTkcKkTyyckgykky | TTTTTCTT | N |
| Bas1 | TGACTC | TGACTC | A, K, M, N |
| Cad1 | mTTAsTmAkC | TTACTAA | A, C, D, M, N |
| Cbf1 | tCACGTG | rTCACrTGA | A, C, D, K, M, N |
| Cin5 | TTAcrTAA | TTACTAA | A, C, D |
| Dal80 | | GATAA | |
| Dal81 | | AAAAGCCGCGGGCGGGATT | |
| Dal82 | GATAAG | | D, K |
| Dig1 | TgAAAca | | A, C, D, K, M, N |
| Fhl1 | TGTayGGrtg | | A, C, D, K, M, N |
| Fkh1 | gtAAAcAA | GGTAAACAA | A, C, D, K, M, N |
| Fkh2 | GTAAACA | GGTAAACAA | A, C, D, K, M, N |
| Gal4 | CGGnnnnnnnnnncCg | CGGnnnnnnnnnnCCG | A, K |
| Gal80 | | CGGnnnnnnnnnnCCG | |
| Gat1 | aGATAAG | GATAA | K |
| Gcn4 | TGAsTCa | ArTGACTCw | A, C, D, K, M, N |
| Gcr1 | | GGCTTCCwC | |
| Gln3 | GATAAGa | GATAAGATAAG | C, D, K |
| Gzf3 | | GATAAG | |
| Hac1 | | kGmCAGCGTGTC | |
| Hap1 | GGnnaTAnCGs | CGGnnnTAnCGG | C, M |
| Hap2 | | CCAAT | |
| Hap3 | | CCAAT | |
| Hap4 | gnCcAAtcA | YCNNCCAATNANM | A, C, D, M, N |
| Hap5 | | CCAAT | |
| Hsf1 | TTCynnnnnnnTTC | TTCTAGAAnnTTCT | A, C, D, K, M, N |
| Ime1 | AAkGAAAnkwA | | A |
| Ino2 | CAcaTGc | ATTTCACATC | C, D, M, N |
| Ino4 | CATGTGaa | CATGTGAAAT | A, C, D, K, M, N |
| Leu3 | cCGgtacCGG | yGCCGGTACCGGyk | A, D, K, M |
| Mac1 | | GAGCAAA | |
| Mbp1 | ACGCGt | ACGCGT | A, C, D, K, M, N |
| Mcm1 | CCnrAtnngg | wTTCCyAAwnnGGTAA | A, C, D, M, N |
| Met31 | | AAACTGTGG | |
| Met32 | | AAACTGTGG | |
| Met4 | RMmAwsTGKSgyGsc | | C |
| Mot3 | | yAGGyA | |
| Msn2 | mAGGGGsgg | mAGGGG | M |
| Msn4 | | mAGGGG | |
| Ndd1 | CCnrAwnnGG | | A, D |
| Nrg1 | GGaCCCT | CCCT | A, C, D, M, N |
| Opi1 | | TCGAAyC | |
| Pdr1 | ccGCCgRAwr | CCGCGG | M |
| Pdr3 | | TCCGCGGA | |
| Phd1 | scnGCngg | | A, D, N |
| Pho2 | SGTGCGsygyG | | N |
| Pho4 | CACGTGs | cacgtkng | D, K, N |
| Put3 | | CGGnnnnnnnnnnCCG | |
| Rap1 | cayCCrtrCa | wrmACCCATACAyy | A, C, D, M, N |
| Rcs1 | ggGTGcant | AAmTGGGTGCAkT | C, D, M, N |
| Rds1 | kCGGCCGa | | D, N |
| Reb1 | TTACCCG | TTACCCGG | A, C, D, K, M, N |
| Rfx1 | TTgccATggCAAC | | D |
| Rgt1 | | CGGAnnA | |
| Rim101 | | TGCCAAG | |
| Rlm1 | | CTAwwwwTAG | |
| Rlr1 | ATTTTCnnCwTt | | N |
| Rox1 | | ysyATTGTT | |
| Rph1 | | CCCCTTAAGG | |
| Rpn4 | GGTGGCAAA | GGTGGCAAA | A, C, D, K, M, N |
| Rtg3 | | GGTCAC | |
| Sfp1 | ayCcrtACay | | A, C, D, M, N |
| Sig1 | ArGmAwCrAmAA | | M |
| Sip4 | CGGnynAATGGrr | yCGGAyrrAwGG | D |
| Skn7 | GnCnnGsCs | ATTTGGCyGGsCC | A, C, D, M, N |
| Sko1 | | ACGTCA | |
| Smp1 | | ACTACTAwwwwTAG | |
| Snt2 | yGGCGCTAyca | | A, C, D, M, N |

TABLE 3-continued

Regulator specificities

| Regulator | Discovered specificity[1] | Known specificity[1,2] | Programs[3] |
|---|---|---|---|
| Sok2 | tGGAgnna | | A |
| Spt2 | ymtGTmTytAw | | M |
| Spt23 | rAAATsaA | | C |
| Stb1 | rracGCsAa | | C, D, K, M, N |
| Stb4 | TCGnnCGA | | K |
| Stb5 | CGGnstTAta | CGG | D, N |
| Ste12 | tgAAAC | ATGAAAC | A, C, D, K, M, N |
| Stp1 | | rCGGCnnnrCGGC | |
| Sum1 | gyGwCAswaaw | AGyGwCACAAAAk | A, C, D, M, N |
| Sut1 | gcsGsgnnsG | CGCG | A, D, M |
| Swi4 | CgCsAAA | CnCGAAA | A, C, D, K, M, N |
| Swi5 | | kGCTGr | |
| Swi6 | CGCgaaa | CnCGAAA | A, C, D, M, N |
| Tec1 | CATTCyy | CATTCy | C |
| Thi2 | gmAAcyntwAgA | | C, D |
| Tye7 | tCACGTGa | CAnnTG | A, C, D, M |
| Uga3 | | CCGnnnnCGG | |
| Ume6 | taGCCGCCsa | wGCCGCCGw | A, C, D, K, M, N |
| Xbp1 | | CTTCGAG | |
| Yap1 | TTaGTmAGc | TTAsTmA | A, C, D, M |
| Yap3 | | TTACTAA | |
| Yap5 | | TTACTAA | |
| Yap6 | | TTACTAA | |
| Yap7 | mTkAsTmA | TTACTAA | A, C, D, M, N |
| YDR026C | tTACCCGGm | | C, D, M, N |
| Yhp1 | | TAATTG | |
| Yox1 | | YAATA | |
| Zap1 | ACCCTmAAGGTyrT | ACCCTAAAGGT | N |

[1]Text representation of the probability matrices. Lowercase letters indicate a weaker preference (less information content at that position of the probability matrix). Ambiguity Codes: S = C or G, W = A or T, R = A or G, Y = C or T, K = G or T, M = A or C, n = A, C, G or T.
[2]Known specificities are taken from the YPD, SCPD, and TRANSFAC databases.
[3]Program Codes: A = AlignACE, C = CONVERGE, D = MDscan, K = Kellis et al., M = MEME, N = MEME_c.

TABLE 4

Overrepresented MIPS categories among single-regulator architecture binding targets

| Regulator | P value[1] | Enriched MIPS category[2] |
|---|---|---|
| Bas1 | 6.10e−09 | nucleotide metabolism* |
| Fhl1 | 1.73e−15 | ribosome biogenesis |
| Gal4 | 2.18e−04 | C-compound and carbohydrate metabolism* |
| Gat1 | 4.92e−05 | nitrogen and sulfur metabolism* |
| Gat1 | 2.63e−02 | mRNA transcription* |
| Gat1 | 4.38e−02 | amino acid metabolism |
| Gcn4 | 8.72e−12 | amino acid metabolism* |
| Gzf3 | 2.21e−02 | transport mechanism |
| Hap3 | 6.03e−03 | lipid, fatty-acid and isoprenoid metabolism |
| Hap3 | 1.61e−02 | allantoin and allantoate transporters |
| Hap3 | 2.50e−02 | other energy generation activities |
| Hap4 | 3.33e−10 | respiration |
| Hap4 | 1.78e−05 | mitochondrial transport |
| Hap4 | 1.03e−02 | transport mechanism |
| Hap4 | 2.12e−02 | assembly of protein complexes |
| Hsf1 | 6.58e−06 | stress response* |
| Ino4 | 5.31e−03 | lipid, fatty-acid and isoprenoid metabolism* |
| Mbp1 | 1.04e−04 | DNA processing |
| Met32 | 1.13e−04 | amino acid metabolism* |
| Met32 | 1.21e−03 | nitrogen and sulfur metabolism* |
| Met32 | 4.64e−02 | amino-acid transporters |
| Mot3 | 3.89e−02 | DNA processing |
| Msn2 | 4.40e−02 | metabolism of energy reserves (glycogen, trehalose) |
| Put3 | 3.45e−02 | other transport facilitators |
| Reb1 | 2.09e−05 | vesicular transport (Golgi network, etc.) |
| Rfx1 | 3.57e−02 | other protein-synthesis activities |
| Rox1 | 3.43e−02 | cell death |
| Rpn4 | 2.49e−13 | proteolytic degradation* |
| Rtg3 | 8.50e−03 | other transcription activities |
| Sig1 | 2.97e−02 | cell cycle |
| Sip4 | 2.69e−03 | glyoxylate cycle |
| Sip4 | 1.57e−02 | glycolysis and gluconeogenesis |
| Stb4 | 4.02e−02 | allantoin and allantoate transporters electron transport and membrane-associated energy |
| Stb5 | 2.42e−02 | conservation |
| Ste12 | 5.56e−03 | cell differentiation* |
| Sut1 | 5.37e−03 | glyoxylate cycle |
| Swi6 | 7.96e−03 | nitrogen and sulfur metabolism |
| Thi2 | 1.15e−02 | mRNA transcription* |
| Thi2 | 2.45e−02 | metabolism of vitamins, cofactors, and prosthetic groups |

[1]P values represent the probability, based on the hypergeometric distribution, of finding the observed number of genes (or more) with the specified MIPS Level 2 category under the null hypothesis that the genes were selected at random. The values have been corrected for testing multiple categories using Bonferroni correction.
[2]An asterisk (*) indicates that the category is also associated with the regulator itself.

TABLE 5

Regulators with a preference for repetitive motifs

| Regulator | P value[1] | Non-repetitive | Repetitive |
|---|---|---|---|
| Dig1 | 1.43e−08 | O: 25 E: 45 | O: 38 E: 17 |
| Mbp1 | 2.99e−08 | O: 34 E: 56 | O: 44 E: 21 |
| Swi6 | 7.36e−06 | O: 34 E: 50 | O: 37 E: 20 |
| Sok2 | 1.34e−05 | O: 13 E: 24 | O: 21 E: 9 |
| Bas1 | 2.84e−04 | O: 6 E: 12 | O: 12 E: 5 |
| Ste12 | 5.57e−04 | O: 48 E: 62 | O: 39 E: 24 |
| Swi4 | 7.29e−04 | O: 27 E: 38 | O: 26 E: 14 |
| Phd1 | 7.89e−03 | O: 15 E: 21 | O: 15 E: 8 |
| Aft2 | 9.73e−03 | O: 22 E: 29 | O: 19 E: 11 |
| Swi5 | 1.05e−02 | O: 11 E: 16 | O: 12 E: 6 |
| Sfp1 | 3.03e−02 | O: 7 E: 10 | O: 8 E: 4 |
| Ino2 | 4.77e−02 | O: 11 E: 15 | O: 10 E: 5 |

[1]P values represent the one-tailed probability, based on the chi-square distribution, of finding the observed number of non-repetitive and repetitive motif architecture promoters under the null hypothesis that the distribution for each regulator is the same as the average distribution for all regulators. O = observed number of occurrences; E = expected number of occurrences.

TABLE 6

Co-occurring regulator pairs[1]

Ace2, Fkh2
Ace2, Swi5
Aft2, Rcs1
Arr1, Yap3
Azf1, Gzf3
Bas1, Met4
Cad1, Yap1
Cad1, Yap7
Cbf1, Met31
Cbf1, Met32
Cbf1, Met4
Cbf1, Pho4
Cbf1, Tye7
Cin5, Phd1
Cin5, Skn7
Cin5, Sok2
Cin5, Sut1
Cin5, Xbp1
Cin5, Yap6
Dal82, Gat1
Dal82, Gln3
Dal82, Hap2
Dig1, Mcm1
Dig1, Ste12
Dig1, Swi4
Dig1, Swi6
Dig1, Tec1
Fhl1, Rap1
Fhl1, Sfp1
Fkh1, Fkh2
Fkh2, Mcm1
Fkh2, Ndd1
Fkh2, Swi6
Gat1, Spt23
Gcn4, Gln3
Gcn4, Leu3
Gcr1, Tye7
Gln3, Hap2
Gzf3, Pdr1
Hap2, Hap3
Hap2, Hap4
Hap2, Hap5
Hap3, Hap5
Hap4, Hap5
Hsf1, Msn4
Ino2, Ino4
Ino4, Sko1
Mac1, Rcs1
Mbp1, Stb1
Mbp1, Swi4
Mbp1, Swi6
Mcm1, Ndd1
Mcm1, Ste12
Mcm1, Swi4
Mcm1, Swi6
Mcm1, Tec1
Met31, Met32
Met31, Met4
Met32, Met4
Mot3, Rox1
Mot3, Skn7
Msn2, Msn4
Msn4, Nrg1
Nrg1, Rlm1
Nrg1, Skn7
Phd1, Rox1
Phd1, Skn7
Phd1, Sok2
Phd1, Sut1
Phd1, Swi6
Rap1, Sfp1
Rim101, Yox1
Rlm1, Sko1
Rox1, Sut1
Sip4, Stp1
Skn7, Sok2
Skn7, Sut1
Skn7, Swi6
Skn7, Xbp1
Sko1, Sok2
Sok2, Sut1
Sok2, Swi6
Spt23, Yox1
Stb1, Swi4
Stb1, Swi6
Stb1, Tec1
Ste12, Swi4
Ste12, Swi6
Ste12, Tec1
Swi4, Swi6
Swi4, Tec1
Swi6, Tec1
Yap1, Yap7
Yap6, Yap7

[1]Shown are co-occurring regulator pairs ($P \leq 0.005$). P values represent the probability, based on the hypergeometric distribution, of finding the observed number of intergenic regions (or more) bound by both regulators under the null hypothesis that binding for the two regulators is independent.

TABLE 7

Behavior classifications of regulators[1]

| Invariant[2] | Enabled[3] | Expanded[4] | Altered[5] |
|---|---|---|---|
| Fhl1 | Adr1 | Bas1 | Adr1 |
| Gal4 | Arr1 | Cad1 | Aft2 |
| Gcn4 | Ash1 | Cbf1 | Cad1 |
| Hsf1 | Dal81 | Cin5 | Cin5 |
| Leu3 | Fhl1 | Dal82 | Dal80 |
| Put3 | Gat1 | Fkh2 | Dal82 |
| Ste12 | Hap4 | Gal4 | Dig1 |
| Ume1 | Hsf1 | Gcn4 | Fkh2 |

TABLE 7-continued

Behavior classifications of regulators[1]

| Invariant[2] | Enabled[3] | Expanded[4] | Altered[5] |
|---|---|---|---|
| Yap7 | Mot3 | Gln3 | Gat1 |
| | Msn2 | Hap2 | Gln3 |
| | Pdr1 | Mac1 | Gzf3 |
| | Phd1 | Mbp1 | Hap4 |
| | Pho2 | Mcm1 | Hap5 |
| | Put3 | Met31 | Mbp1 |
| | Rap1 | Met32 | Mot3 |
| | Rgt1 | Met4 | Msn2 |
| | Rim101 | Nrg1 | Msn4 |
| | Rlm1 | Rcs1 | Phd1 |
| | Rph1 | Rds1 | Pho4 |
| | Rpn4 | Reb1 | Reb1 |
| | Rtg3 | Rox1 | Rox1 |
| | Sfp1 | Rpn4 | Rtg3 |
| | Sig1 | Rtg3 | Skn7 |
| | Sip4 | Skn7 | Ste12 |
| | Sok2 | Ste12 | Tec1 |
| | Stp1 | | Ume6 |
| | Thi2 | | Yap1 |
| | Uga3 | | Yap6 |
| | Xbp1 | | |
| | Yap1 | | |
| | Yap7 | | |

[1]The binding of each regulator was compared in pairwise fashion for every environmental condition in which that regulator was profiled. Some regulators fall into multiple categories depending on exactly which conditions are compared.
[2]The ratio of the overlap of bound probes for a regulator (P ≦ 0.001) was greater than 0.66 and the ratio of the number of bound probes was between 0.66 and 1.5.
[3]Regulator bound to no probes in one environment.
[4]The ratio of the overlap of bound probes for a regulator was greater than 0.66 and the ratio of the number of bound probes was less than 0.66 or greater than 1.5.
[5]Regulator bound at least one probe in both environments and the ratio of the overlap of bound probes was less than 0.66.

TABLE 8

Motif score significance cutoffs (P ≦ 0.001)

| Number of sequences | Converge | AlignACE | MDscan | MEME | MEME_c |
|---|---|---|---|---|---|
| | | Enrichment Score[1] | | | |
| 10 | 12.70 | 20.32 | 11.78 | 13.54 | n/a |
| 20 | 11.96 | 21.14 | 12.95 | 12.89 | 9.81 |
| 30 | 11.43 | 20.43 | 13.30 | 12.57 | n/a |
| 40 | 11.34 | 20.62 | 14.04 | 11.64 | 7.53 |
| 50 | 10.74 | 19.94 | 12.23 | 12.81 | 7.43 |
| 60 | 10.50 | 19.71 | 10.95 | 12.37 | n/a |
| 70 | 10.34 | 18.30 | 13.25 | 11.34 | n/a |
| 80 | 10.20 | 19.40 | 12.84 | 11.93 | n/a |
| 100 | 9.36 | 20.31 | 11.56 | 10.58 | 2.91 |
| 120 | n/a | 18.59 | 13.14 | 10.94 | n/a |
| 140 | 8.14 | 18.52 | 11.26 | 10.87 | n/a |
| 160 | n/a | 20.04 | 11.38 | 9.77 | n/a |
| | | ROC a.u.c.[1] | | | |
| 10 | n/a | n/a | n/a | n/a | n/a |
| 20 | 0.812 | 0.842 | 0.857 | 0.925 | n/a |
| 30 | 0.758 | 0.773 | 0.793 | 0.831 | 0.785 |
| 40 | 0.720 | 0.713 | 0.758 | 0.764 | 0.737 |
| 50 | 0.687 | 0.674 | 0.719 | 0.737 | 0.711 |
| 60 | 0.670 | 0.662 | 0.688 | 0.706 | 0.654 |
| 70 | 0.663 | 0.641 | 0.686 | 0.684 | 0.664 |
| 80 | 0.643 | 0.626 | 0.670 | 0.675 | 0.648 |
| 100 | 0.634 | 0.615 | 0.664 | 0.633 | 0.606 |
| 120 | 0.624 | 0.604 | 0.629 | 0.624 | 0.602 |
| 140 | 0.608 | n/a | 0.634 | n/a | 0.590 |
| 160 | 0.594 | 0.580 | 0.613 | 0.593 | 0.588 |

[1]Motif score significance P ≦ 0.001 thresholds for "Enrichment" and "ROC a.u.c." specificity metrics obtained from calculations on randomized selections of intergenic regions as described in Methods. Entries containing "n/a" denote that the empirical distribution was not normal. The threshold for the CC4 metric (4.95) is not dependent on the number of sequences.

The invention claimed is:

1. A method of identifying a set of biologically-active DNA-binding sites for a protein of interest in the genome of a cell, the method comprising
   (i) identifying a set of regions of genomic DNA to which the protein of interest is bound in the cell;
   (ii) identifying candidate DNA-binding sites in the identified regions of genomic DNA, wherein a candidate DNA-binding site comprises a sequence corresponding to a DNA-sequence motif for the protein of interest, and wherein said DNA sequence motif is enriched in said identified regions by a statistically significant amount relative to a set of genomic regions which are bound by a mutant form of the protein of interest in the cell;
   (iii) determining if the candidate DNA-binding sites are conserved in an equivalent genomic region in one or more species different from the species from which the cell is obtained, wherein a candidate DNA-binding site that is conserved in at least one of the different species is a biologically-active DNA-binding site.

2. The method of claim 1, wherein the regions of genomic DNA comprise promoter regions.

3. The method of claim 1, wherein a candidate DNA-binding site is conserved if the equivalent genomic region in at least one different species comprises a nucleic acid sequence that matches the DNA-sequence motif for the protein of interest.

4. The method of claim 1, wherein the candidate DNA-binding site is less than 20 bp in length.

5. The method of claim 1, wherein the DNA-sequence motif is degenerate in at least one position.

6. The method of claim 1, wherein step (iii) comprises determining if the candidate DNA-binding sites are conserved in equivalent genomic regions in two or more different species.

7. The method of claim 1, wherein the set of biologically-active DNA-binding sites comprises one or more biologically-active DNA-binding sites.

8. The method of claim 1, wherein two regions of genomic DNA are equivalent if they both comprise a sequence of at least one orthologous gene.

9. The method of claim 1, wherein the cell is an eukaryotic cell.

10. A method of identifying an agent which alters the set of biologically-active DNA-binding sites for a protein of interest in the genome of a cell, the method comprising
- (i) contacting an experimental cell with a candidate agent;
- (ii) identifying a set of biologically-active DNA-binding sites for a protein of interest in the genome of the cell of step (i) by:
  - (a) identifying a set of regions of genomic DNA to which the protein of interest is bound in the cell;
  - (b) identifying candidate DNA-binding sites in the identified regions of genomic DNA, wherein a candidate DNA-binding site comprises a sequence corresponding to a DNA-sequence motif for the protein of interest, wherein the DNA sequence motif is enriched by a statistically significant amount relative to a suitable control;
  - (c) determining if the candidate DNA-binding sites are conserved in an equivalent genomic region in one or more species different from the species from which the cell is obtained, wherein a candidate DNA-binding site that is conserved in at least one of the different species is a biologically-active DNA-binding site;
  - thereby generating an experimental set of biologically-active DNA-binding sites;
- (iii) comparing
  - (1) the experimental set of biologically-active DNA-binding sites to
  - (2) a control set of biologically-active DNA-binding sites for the protein of interest;
  - wherein a candidate agent is identified if the experimental set and the control set differ.

11. A method of identifying a pathway that is transcriptionally regulated by a protein of interest in a cell, the method comprising
- (i) identifying a set of biologically-active DNA-binding sites for a protein of interest in the genome of the cell according to the method of claim 1; and
- (ii) identifying at least two candidate genes likely to be regulated by binding of the protein of interest to the set of biologically-active DNA-binding sites identified in (i); wherein a pathway that is transcriptionally regulated by the protein of interest is identified if at least two candidate genes are members of the same pathway.

12. The method of claim 11, wherein the pathway is a gene expression pathway.

13. A method of identifying two sets of conditions in which a protein of interest differentially binds to the genome of a cell, the method comprising:
- (i) identifying, according to the method of claim 1,
  - (1) a first set of biologically-active DNA-binding sites for the protein of interest in the genome of a cell, wherein the cell is exposed to a first set of conditions; and
  - (2) identifying a second set of biologically-active DNA-binding sites for the protein of interest in the genome of a cell, wherein the cell is exposed to a second set of conditions; and
- (ii) identifying a difference in the first set of biologically-active DNA-binding sites relative to the second set of biologically-active DNA-binding sites, thereby identifying two sets of conditions in which a protein of interest differentially binds to the genome of a cell.

14. A method of identifying a property of a gene product of a gene of interest that correlates with the binding activity of a polypeptide encoded by the gene of interest to the genome of a cell, the method comprising
- (i) identifying two sets of conditions in which a protein of interest differentially binds to the genome of the cell according to the method of claim 13;
- (ii) determining a property of a gene product of the gene of interest in (a) a cell exposed to the first set of conditions; and in (b) a cell exposed to the second set of conditions; and
- (iii) determining if at least one property of the gene product differs in the two cells of step (ii),
- thereby identifying a property of said gene product that correlates with the binding activity of a said polypeptide to the genome of a cell.

15. A method of identifying a property of a gene product of a gene of interest that correlates with the binding activity of a polypeptide encoded by the gene of interest to the genome of a cell, the method comprising
- (i) identifying an agent which alters the set of biologically-active DNA-binding sites for a protein of interest in the genome of a cell according to the method of claim 10;
- (ii) determining a property of a gene product of the gene of interest in (a) a cell contacted with the agent; and in (b) a cell not contacted with the agent; and
- (iii) determining if at least one property of the gene product differs in the two cells of step (ii),
- thereby identifying a property that correlates with the binding activity of a gene of interest to the genome of a cell.

16. The method of claim 14, wherein the property is selected from the group consisting of a protein modification, expression level, enzymatic activity and intracellular localization.

17. A method of identifying two cell genotypes in which a protein of interest differentially binds to the genome, the method comprising:
- (i) identifying a first set of biologically-active DNA-binding sites for the protein of interest in the genome of a cell of a first genotype;
- (ii) identifying a second set of biologically-active DNA-binding sites for the protein of interest in the genome of a cell of a second genotype;
- (iii) comparing the first set of biologically-active DNA-binding sites to the second set of biologically-active DNA-binding sites and determining if the two sets differ, thereby identifying two cell genotypes in which said protein of interest differentially binds to the genome.

* * * * *

```
                         SEQUENCE LISTING

<160> NUMBER OF SEQ ID NOS: 59

<210> SEQ ID NO 1
<211> LENGTH: 12
<212> TYPE: DNA
<213> ORGANISM: S. cerevisae

<400> SEQUENCE: 1
atcgcacgtg at                                                          12

<210> SEQ ID NO 2
<211> LENGTH: 12
<212> TYPE: DNA
<213> ORGANISM: S. paradoxus

<400> SEQUENCE: 2
atttcacatg at                                                          12

<210> SEQ ID NO 3
<211> LENGTH: 12
<212> TYPE: DNA
<213> ORGANISM: S. mikatae

<400> SEQUENCE: 3
```

```
atactacgtg ac                                                              12
```

```
<210> SEQ ID NO 4
<211> LENGTH: 12
<212> TYPE: DNA
<213> ORGANISM: S. bayanus

<400> SEQUENCE: 4
cttgcacgtg cc                                                              12

<210> SEQ ID NO 5
<211> LENGTH: 10
<212> TYPE: DNA
<213> ORGANISM: Artificial Sequence
<220> FEATURE:
<223> OTHER INFORMATION: Recognition sequence for YDR026C

<400> SEQUENCE: 5 tttacccggm                                                                 10

<210> SEQ ID NO 6
<211> LENGTH: 18
<212> TYPE: DNA
<213> ORGANISM: Artificial Sequence
<220> FEATURE:
<223> OTHER INFORMATION: Unlabeled competitor for Cin5 binding

<400> SEQUENCE: 6
gcgacattac ctaagggc                                                        18

<210> SEQ ID NO 7
<211> LENGTH: 18
<212> TYPE: DNA
<213> ORGANISM: Artificial Sequence
<220> FEATURE:
<223> OTHER INFORMATION: Unlabeled competitor for Cin5 binding

<400> SEQUENCE: 7
gcgacattac taaagggc                                                        18

<210> SEQ ID NO 8
<211> LENGTH: 13
<212> TYPE: DNA
<213> ORGANISM: Artificial Sequence
<220> FEATURE:
<223> OTHER INFORMATION: Discovered binding site for Abf1
<220> FEATURE:
<221> NAME/KEY: misc_feature
<222> LOCATION: 7, 8, 9, 10
<223> OTHER INFORMATION: n = A,T,C or G

<400> SEQUENCE: 8
rtcaytnnnn acg                                                             13

<210> SEQ ID NO 9
<211> LENGTH: 14
<212> TYPE: DNA
<213> ORGANISM: Artificial Sequence
<220> FEATURE:
<223> OTHER INFORMATION: Known binding site for Abf1
<220> FEATURE:
<221> NAME/KEY: misc_feature
<222> LOCATION: 7, 8, 9, 10
<223> OTHER INFORMATION: n = A,T,C or G

<400> SEQUENCE: 9
rtcaytnnnn acgw                                                            14
```

<210> SEQ ID NO 10
<211> LENGTH: 14
<212> TYPE: DNA
<213> ORGANISM: Artificial Sequence
<220> FEATURE:
<223> OTHER INFORMATION: Known binding site for Abf2

<400> SEQUENCE: 10
aaagtgcacc catt                                                    14

<210> SEQ ID NO 11
<211> LENGTH: 18
<212> TYPE: DNA
<213> ORGANISM: Artificial Sequence
<220> FEATURE:
<223> OTHER INFORMATION: Discovered binding site for Azf1

<400> SEQUENCE: 11
ywttkckkty yckgykky                                                18

<210> SEQ ID NO 12
<211> LENGTH: 10
<212> TYPE: DNA
<213> ORGANISM: Artificial Sequence
<220> FEATURE:
<223> OTHER INFORMATION: Discovered binding site for Cad1

<400> SEQUENCE: 12 mttastmakc                                                         10

<210> SEQ ID NO 13
<211> LENGTH: 19
<212> TYPE: DNA
<213> ORGANISM: Artificial Sequence
<220> FEATURE:
<223> OTHER INFORMATION: Known binding site for Dal81

<400> SEQUENCE: 13
aaaagccgcg ggcgggatt                                               19

<210> SEQ ID NO 14
<211> LENGTH: 17
<212> TYPE: DNA
<213> ORGANISM: Artificial Sequence
<220> FEATURE:
<223> OTHER INFORMATION: Discovered binding site for Gal4
<220> FEATURE:
<221> NAME/KEY: misc_feature
<222> LOCATION: 4, 5, 6, 7, 8, 9, 10, 11, 12, 13, 14
<223> OTHER INFORMATION: n = A,T,C or G

<400> SEQUENCE: 14
cggnnnnnnn nnnnccg                                                 17

<210> SEQ ID NO 15
<211> LENGTH: 17
<212> TYPE: DNA
<213> ORGANISM: Artificial Sequence
<220> FEATURE:
<223> OTHER INFORMATION: Known binding site for Gal4
<220> FEATURE:
<221> NAME/KEY: misc_feature
<222> LOCATION: 4, 5, 6, 7, 8, 9, 10, 11, 12, 13, 14
<223> OTHER INFORMATION: n = A,T,C or G

<400> SEQUENCE: 15

```
cggnnnnnnn nnnnccg                                                    17
```

<210> SEQ ID NO 16
<211> LENGTH: 17
<212> TYPE: DNA
<213> ORGANISM: Artificial Sequence
<220> FEATURE:
<223> OTHER INFORMATION: Known binding site for Gal80
<220> FEATURE:
<221> NAME/KEY: misc_feature
<222> LOCATION: 4, 5, 6, 7, 8, 9, 10, 11, 12, 13, 14
<223> OTHER INFORMATION: n = A,T,C or G

<400> SEQUENCE: 16

```
cggnnnnnnn nnnnccg                                                    17
```

<210> SEQ ID NO 17
<211> LENGTH: 11
<212> TYPE: DNA
<213> ORGANISM: Artificial Sequence
<220> FEATURE:
<223> OTHER INFORMATION: Known binding site for Gln3

<400> SEQUENCE: 17

```
gataagataa g                                                          11
```

<210> SEQ ID NO 18
<211> LENGTH: 11
<212> TYPE: DNA
<213> ORGANISM: Artificial Sequence
<220> FEATURE:
<223> OTHER INFORMATION: Discovered binding site for Hap1
<220> FEATURE:
<221> NAME/KEY: misc_feature
<222> LOCATION: 3, 4, 8
<223> OTHER INFORMATION: n = A,T,C or G

<400> SEQUENCE: 18

```
ggnnatancg s                                                          11
```

<210> SEQ ID NO 19
<211> LENGTH: 13
<212> TYPE: DNA
<213> ORGANISM: Artificial Sequence
<220> FEATURE:
<223> OTHER INFORMATION: Known binding site for Hap4
<220> FEATURE:
<221> NAME/KEY: misc_feature
<222> LOCATION: 3, 4, 10, 12
<223> OTHER INFORMATION: n = A,T,C or G

<400> SEQUENCE: 19

```
ycnnccaatn anm                                                        13
```

<210> SEQ ID NO 20
<211> LENGTH: 12
<212> TYPE: DNA
<213> ORGANISM: Artificial Sequence
<220> FEATURE:
<223> OTHER INFORMATION: Known binding site for Hac1

<400> SEQUENCE: 20

```
kgmcagcgtg tc                                                         12
```

<210> SEQ ID NO 21
<211> LENGTH: 12
<212> TYPE: DNA
<213> ORGANISM: Artificial Sequence

```
<220> FEATURE:
<223> OTHER INFORMATION: Known binding site for Hap1
<220> FEATURE:
<221> NAME/KEY: misc_feature
<222> LOCATION: 4, 5, 6, 9
<223> OTHER INFORMATION: n = A,T,C or G

<400> SEQUENCE: 21
cggnnntanc gg                                                             12

<210> SEQ ID NO 22
<211> LENGTH: 13
<212> TYPE: DNA
<213> ORGANISM: Artificial Sequence
<220> FEATURE:
<223> OTHER INFORMATION: Discovered binding site for Hsf1
<220> FEATURE:
<221> NAME/KEY: misc_feature
<222> LOCATION: 5, 6, 7, 8, 9, 10
<223> OTHER INFORMATION: n = A,T,C or G

<400> SEQUENCE: 22
ttcynnnnnn ttc                                                            13

<210> SEQ ID NO 23
<211> LENGTH: 14
<212> TYPE: DNA
<213> ORGANISM: Artificial Sequence
<220> FEATURE:
<223> OTHER INFORMATION: Known binding site for Hsf1
<220> FEATURE:
<221> NAME/KEY: misc_feature
<222> LOCATION: 9, 10
<223> OTHER INFORMATION: n = A,T,C or G

<400> SEQUENCE: 23
ttctagaann ttct                                                           14

<210> SEQ ID NO 24
<211> LENGTH: 11
<212> TYPE: DNA
<213> ORGANISM: Artificial Sequence
<220> FEATURE:
<223> OTHER INFORMATION: Discovered binding site for Ime1
<220> FEATURE:
<221> NAME/KEY: misc_feature
<222> LOCATION: 8
<223> OTHER INFORMATION: n = A,T,C or G

<400> SEQUENCE: 24
aakgaaankw a                                                              11

<210> SEQ ID NO 25
<211> LENGTH: 10
<212> TYPE: DNA
<213> ORGANISM: Artificial Sequence
<220> FEATURE:
<223> OTHER INFORMATION: Known binding site for Ino2

<400> SEQUENCE: 25
atttcacatc                                                                10

<210> SEQ ID NO 26
<211> LENGTH: 10
<212> TYPE: DNA
<213> ORGANISM: Artificial Sequence
<220> FEATURE:
<223> OTHER INFORMATION: Known binding site for Ino4
```

```
<400> SEQUENCE: 26
catgtgaaat                                                              10

<210> SEQ ID NO 27
<211> LENGTH: 10
<212> TYPE: DNA
<213> ORGANISM: Artificial Sequence
<220> FEATURE:
<223> OTHER INFORMATION: Discovered binding site for Leu3

<400> SEQUENCE: 27
ccggtaccgg                                                              10

<210> SEQ ID NO 28
<211> LENGTH: 14
<212> TYPE: DNA
<213> ORGANISM: Artificial Sequence
<220> FEATURE:
<223> OTHER INFORMATION: Known binding site for Leu3

<400> SEQUENCE: 28
ygccggtacc ggyk                                                         14

<210> SEQ ID NO 29
<211> LENGTH: 10
<212> TYPE: DNA
<213> ORGANISM: Artificial Sequence
<220> FEATURE:
<223> OTHER INFORMATION: Discovered binding site for Mcm1
<220> FEATURE:
<221> NAME/KEY: misc_feature
<222> LOCATION: 3, 7, 8
<223> OTHER INFORMATION: n = A,T,C or G

<400> SEQUENCE: 29 ccnratnngg                                                              10

<210> SEQ ID NO 30
<211> LENGTH: 16
<212> TYPE: DNA
<213> ORGANISM: Artificial Sequence
<220> FEATURE:
<223> OTHER INFORMATION: Known binding site for Mcm1
<220> FEATURE:
<221> NAME/KEY: misc_feature
<222> LOCATION: 10, 11
<223> OTHER INFORMATION: n = A,T,C or G

<400> SEQUENCE: 30
wttccyaawn nggtaa                                                       16

<210> SEQ ID NO 31
<211> LENGTH: 15
<212> TYPE: DNA
<213> ORGANISM: Artificial Sequence
<220> FEATURE:
<223> OTHER INFORMATION: Discovered binding site for Met4

<400> SEQUENCE: 31
rmmawstgks gygsc                                                        15

<210> SEQ ID NO 32
<211> LENGTH: 10
<212> TYPE: DNA
<213> ORGANISM: Artificial Sequence
<220> FEATURE:
<223> OTHER INFORMATION: Discovered binding site for Ndd1
```

```
<220> FEATURE:
<221> NAME/KEY: misc_feature
<222> LOCATION: 3, 7, 8
<223> OTHER INFORMATION: n = A,T,C or G

<400> SEQUENCE: 32 ccnrawnngg                                                                10

<210> SEQ ID NO 33
<211> LENGTH: 10
<212> TYPE: DNA
<213> ORGANISM: Artificial Sequence
<220> FEATURE:
<223> OTHER INFORMATION: Discovered binding site for Pdr1

<400> SEQUENCE: 33 ccgccgrawr                                                                10

<210> SEQ ID NO 34
<211> LENGTH: 11
<212> TYPE: DNA
<213> ORGANISM: Artificial Sequence
<220> FEATURE:
<223> OTHER INFORMATION: Discovered binding site for Pho2

<400> SEQUENCE: 34
sgtgcgsygy g                                                              11

<210> SEQ ID NO 35
<211> LENGTH: 16
<212> TYPE: DNA
<213> ORGANISM: Artificial Sequence
<220> FEATURE:
<223> OTHER INFORMATION: Known binding site for Put3
<220> FEATURE:
<221> NAME/KEY: misc_feature
<222> LOCATION: 4, 5, 6, 7, 8, 9, 10, 11, 12, 13
<223> OTHER INFORMATION: n = A,T,C or G

<400> SEQUENCE: 35
cggnnnnnnn nnnccg                                                         16

<210> SEQ ID NO 36
<211> LENGTH: 14
<212> TYPE: DNA
<213> ORGANISM: Artificial Sequence
<220> FEATURE:
<223> OTHER INFORMATION: Known binding site for Rap1

<400> SEQUENCE: 36
wrmacccata cayy                                                           14

<210> SEQ ID NO 37
<211> LENGTH: 13
<212> TYPE: DNA
<213> ORGANISM: Artificial Sequence
<220> FEATURE:
<223> OTHER INFORMATION: Known binding site for Rcs1

<400> SEQUENCE: 37
aamtgggtgc akt                                                            13

<210> SEQ ID NO 38
<211> LENGTH: 13
<212> TYPE: DNA
<213> ORGANISM: Artificial Sequence
<220> FEATURE:
```

```
<223> OTHER INFORMATION: Discovered binding site for Rfx1

<400> SEQUENCE: 38
ttgccatggc aac                                                          13

<210> SEQ ID NO 39
<211> LENGTH: 12
<212> TYPE: DNA
<213> ORGANISM: Artificial Sequence
<220> FEATURE:
<223> OTHER INFORMATION: Discovered binding site for Rlr1
<220> FEATURE:
<221> NAME/KEY: misc_feature
<222> LOCATION: 7, 8
<223> OTHER INFORMATION: n = A,T,C or G

<400> SEQUENCE: 39
attttcnncw tt                                                           12

<210> SEQ ID NO 40
<211> LENGTH: 10
<212> TYPE: DNA
<213> ORGANISM: Artificial Sequence
<220> FEATURE:
<223> OTHER INFORMATION: Known binding site for Rlm1

<400> SEQUENCE: 40 ctawwwwtag                                                              10

<210> SEQ ID NO 41
<211> LENGTH: 10
<212> TYPE: DNA
<213> ORGANISM: Artificial Sequence
<220> FEATURE:
<223> OTHER INFORMATION: Known binding site for Rph1

<400> SEQUENCE: 41
ccccttaagg                                                              10

<210> SEQ ID NO 42
<211> LENGTH: 10
<212> TYPE: DNA
<213> ORGANISM: Artificial Sequence
<220> FEATURE:
<223> OTHER INFORMATION: Discovered binding site for Sfp1

<400> SEQUENCE: 42 ayccrtacay                                                              10

<210> SEQ ID NO 43
<211> LENGTH: 12
<212> TYPE: DNA
<213> ORGANISM: Artificial Sequence
<220> FEATURE:
<223> OTHER INFORMATION: Discovered binding site for Sig1

<400> SEQUENCE: 43
argmawcram aa                                                           12

<210> SEQ ID NO 44
<211> LENGTH: 13
<212> TYPE: DNA
<213> ORGANISM: Artificial Sequence
<220> FEATURE:
<223> OTHER INFORMATION: Discovered binding site for Sip4
<220> FEATURE:
<221> NAME/KEY: misc_feature
```

```
<222> LOCATION: 4, 6
<223> OTHER INFORMATION: n = A,T,C or G

<400> SEQUENCE: 44
cggnynaatg grr                                                        13

<210> SEQ ID NO 45
<211> LENGTH: 12
<212> TYPE: DNA
<213> ORGANISM: Artificial Sequence
<220> FEATURE:
<223> OTHER INFORMATION: Known binding site for Sip4

<400> SEQUENCE: 45
ycggayrraw gg                                                         12

<210> SEQ ID NO 46
<211> LENGTH: 13
<212> TYPE: DNA
<213> ORGANISM: Artificial Sequence
<220> FEATURE:
<223> OTHER INFORMATION: Known binding site for Skn7

<400> SEQUENCE: 46
atttggcygg scc                                                        13

<210> SEQ ID NO 47
<211> LENGTH: 14
<212> TYPE: DNA
<213> ORGANISM: Artificial Sequence
<220> FEATURE:
<223> OTHER INFORMATION: Known binding site for Smp1

<400> SEQUENCE: 47
actactawww wtag                                                       14

<210> SEQ ID NO 48
<211> LENGTH: 11
<212> TYPE: DNA
<213> ORGANISM: Artificial Sequence
<220> FEATURE:
<223> OTHER INFORMATION: Discovered binding site for Snt2

<400> SEQUENCE: 48
yggcgctayc a                                                          11

<210> SEQ ID NO 49
<211> LENGTH: 11
<212> TYPE: DNA
<213> ORGANISM: Artificial Sequence
<220> FEATURE:
<223> OTHER INFORMATION: Discovered binding site for Spt2

<400> SEQUENCE: 49
ymtgtmtyta w                                                          11

<210> SEQ ID NO 50
<211> LENGTH: 10
<212> TYPE: DNA
<213> ORGANISM: Artificial Sequence
<220> FEATURE:
<223> OTHER INFORMATION: Discovered binding site for Stb5
<220> FEATURE:
<221> NAME/KEY: misc_feature
<222> LOCATION: 4
<223> OTHER INFORMATION: n = A,T,C or G
```

```
<400> SEQUENCE: 50 cggnsttata                                                          10

<210> SEQ ID NO 51
<211> LENGTH: 13
<212> TYPE: DNA
<213> ORGANISM: Artificial Sequence
<220> FEATURE:
<223> OTHER INFORMATION: Known binding site for Stp1
<220> FEATURE:
<221> NAME/KEY: misc_feature
<222> LOCATION: 6, 7, 8
<223> OTHER INFORMATION: n = A,T,C or G

<400> SEQUENCE: 51
rcggcnnnrc ggc                                                      13

<210> SEQ ID NO 52
<211> LENGTH: 11
<212> TYPE: DNA
<213> ORGANISM: Artificial Sequence
<220> FEATURE:
<223> OTHER INFORMATION: Discovered binding site for Sum1

<400> SEQUENCE: 52
gygwcaswaa w                                                        11

<210> SEQ ID NO 53
<211> LENGTH: 13
<212> TYPE: DNA
<213> ORGANISM: Artificial Sequence
<220> FEATURE:
<223> OTHER INFORMATION: Known binding site for Sum1

<400> SEQUENCE: 53
agygwcacaa aak                                                      13

<210> SEQ ID NO 54
<211> LENGTH: 10
<212> TYPE: DNA
<213> ORGANISM: Artificial Sequence
<220> FEATURE:
<223> OTHER INFORMATION: Discovered binding site for Sut1
<220> FEATURE:
<221> NAME/KEY: misc_feature
<222> LOCATION: 7, 8
<223> OTHER INFORMATION: n = A,T,C or G

<400> SEQUENCE: 54 gcsgsgnnsg                                                          10

<210> SEQ ID NO 55
<211> LENGTH: 12
<212> TYPE: DNA
<213> ORGANISM: Artificial Sequence
<220> FEATURE:
<223> OTHER INFORMATION: Discovered binding site for Thi2
<220> FEATURE:
<221> NAME/KEY: misc_feature
<222> LOCATION: 7
<223> OTHER INFORMATION: n = A,T,C or G

<400> SEQUENCE: 55
gmaacyntwa ga                                                       12

<210> SEQ ID NO 56
<211> LENGTH: 10
```

```
<212> TYPE: DNA
<213> ORGANISM: Artificial Sequence
<220> FEATURE:
<223> OTHER INFORMATION: Known binding site for Uga3
<220> FEATURE:
<221> NAME/KEY: misc_feature
<222> LOCATION: 4, 5, 6, 7
<223> OTHER INFORMATION: n = A,T,C or G

<400> SEQUENCE: 56 ccgnnnncgg                                                              10

<210> SEQ ID NO 57
<211> LENGTH: 10
<212> TYPE: DNA
<213> ORGANISM: Artificial Sequence
<220> FEATURE:
<223> OTHER INFORMATION: Discovered binding site for Ume6

<400> SEQUENCE: 57 tagccgccsa                                                              10

<210> SEQ ID NO 58
<211> LENGTH: 9
<212> TYPE: DNA
<213> ORGANISM: Artificial Sequence
<220> FEATURE:
<223> OTHER INFORMATION: Discovered binding site for Yap1

<400> SEQUENCE: 58 ttagtmagc                                                                9

<210> SEQ ID NO 59
<211> LENGTH: 14
<212> TYPE: DNA
<213> ORGANISM: Artificial Sequence
<220> FEATURE:
<223> OTHER INFORMATION: Discovered binding site for Zap1

<400> SEQUENCE: 59
accctmaagg tyrt                                                         14
```